(12) United States Patent
Abe et al.

(10) Patent No.: US 11,062,175 B2
(45) Date of Patent: Jul. 13, 2021

(54) SYSTEM, METHOD, AND PROGRAM FOR ESTIMATING REDUCED ATTENTION STATE, AND STORAGE MEDIUM STORING THE SAME PROGRAM

(71) Applicants: Japan Aerospace Exploration Agency, Chofu (JP); National Center of Neurology and Psychiatry, Kodaira (JP)

(72) Inventors: Takashi Abe, Chofu (JP); Satoshi Furukawa, Chofu (JP); Katsuhiko Ogata, Chofu (JP); Kazuo Mishima, Kodaira (JP); Shingo Kitamura, Kodaira (JP)

(73) Assignees: Japan Aerospace Exploration Agency, Tokyo (JP); National Center of Neurology and Psychiatry, Tokyo (JP)

( * ) Notice: Subject to any disclaimer, the term of this patent is extended or adjusted under 35 U.S.C. 154(b) by 195 days.

(21) Appl. No.: 16/462,433

(22) PCT Filed: Nov. 22, 2017

(86) PCT No.: PCT/JP2017/042081
§ 371 (c)(1),
(2) Date: Dec. 29, 2019

(87) PCT Pub. No.: WO2018/097204
PCT Pub. Date: May 31, 2018

(65) Prior Publication Data
US 2020/0218935 A1    Jul. 9, 2020

(30) Foreign Application Priority Data
Nov. 22, 2016   (JP) .............................. JP2016-227148

(51) Int. Cl.
*G06K 9/62* (2006.01)
*G06K 9/00* (2006.01)

(52) U.S. Cl.
CPC ....... *G06K 9/6221* (2013.01); *G06K 9/00335* (2013.01); *G06K 9/00597* (2013.01); *G06K 9/6278* (2013.01)

(58) Field of Classification Search
None
See application file for complete search history.

(56) References Cited

U.S. PATENT DOCUMENTS 10,307,085 B2 *   6/2019   Sales .................. A61B 5/112
2002/0183644 A1 * 12/2002  Levendowski ...... A61B 5/7264
                                                 600/544

(Continued)

FOREIGN PATENT DOCUMENTS

JP   2008-531142 A    8/2008
JP   2010-224637 A   10/2010
JP   2015-116376 A    6/2015

OTHER PUBLICATIONS

Dinges et al., "Microcomputer analyses of performance on portable, simple visual RT task during sustained operations", Behavior Research Methods, Instruments & Computers, 1985, 17(6), pp. 652-655.

(Continued)

*Primary Examiner* — Fayyaz Alam
(74) *Attorney, Agent, or Firm* — McDonnell Boehnen Hulbert & Berghoff LLP

(57) ABSTRACT

A reduced attention state estimation system includes an eyeball movement and eyelid activity measurement unit that measures an eyeball movement and an eyelid activity of a subject to obtain eyeball movement and eyelid activity data, a section determination unit that determines an eye opening section, an eye closing section, an eye-blinking section and a cluster section based on the eyeball movement and eyelid (Continued)

activity data, an eyeball movement and eyelid activity-related information calculation unit that calculates a sharpness of microsaccade or the like for each eye opening section based on the eyeball movement and eyelid activity data, and an attention assessment unit that determines an attention assessment or the like for an eye opening/cluster section, which is an eye opening section and cluster section, based on the sharpness of microsaccade or the like.

11 Claims, 14 Drawing Sheets

(56) References Cited

U.S. PATENT DOCUMENTS

| | | |
|---|---|---|
| 2008/0150734 A1 | 6/2008 | Johns |
| 2010/0033333 A1* | 2/2010 | Victor ............... A61B 5/1114 340/576 |
| 2011/0205350 A1* | 8/2011 | Terashima .......... G08B 21/06 348/78 |
| 2012/0002843 A1 | 1/2012 | Yoda |
| 2013/0215390 A1* | 8/2013 | Johns ................. A61B 3/113 351/209 |
| 2015/0173665 A1 | 6/2015 | Yamataka et al. |
| 2017/0330042 A1* | 11/2017 | Vaziri ............... G06K 9/00604 |
| 2021/0068653 A1* | 3/2021 | Suzuki .............. G06K 9/00248 |

OTHER PUBLICATIONS

Basner et al., "Adaptive Duration PVT Tracks Effects of Sleep Restriction: An Adaptive-Duration Version of the PVT Accurately Tracks Changes in Psychomotor Vigilance Induces by Sleep Restriction", Sleep, 2012, 35(2), pp. 193-202.

Basner et al., "Validity and sensitivity of a brief psychomotor vigilance test (PVT-B) to total and partial sleep deprivation", Acta Astronautica, 2011, vol. 69, pp. 949-959.

National Highway Traffic Safety Administration Final Report: Research on Vehicle-Based Driver Status Performance Monitoring; Development, Validation, and Refinement of Algorithms for Detection of Driver Drowsiness, 1994, 247 pages.

Basner et al., "Maximizing Sensitivity of the Psychomotor Vigilance Test (PVT) to Sleep Loss", Sleep, 2011, 34(5), pp. 581-591.

Abe, Driving Performance and Sleep Problems: Chapter 8. The Present and Future of Sleepiness Detection Device, 2015, 9(1), pp. 55-61.

* cited by examiner

FIG.2
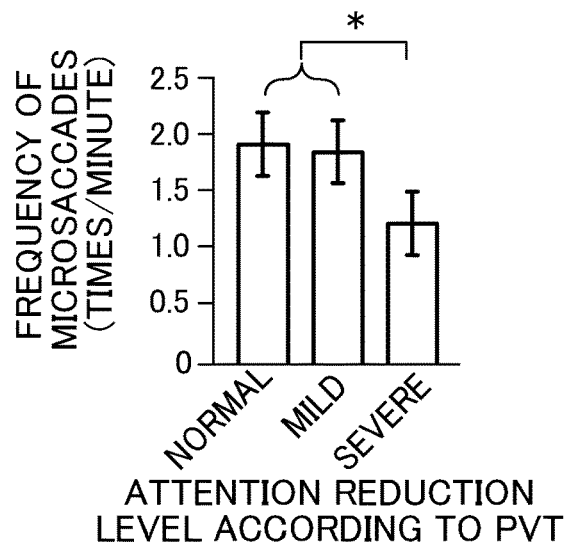
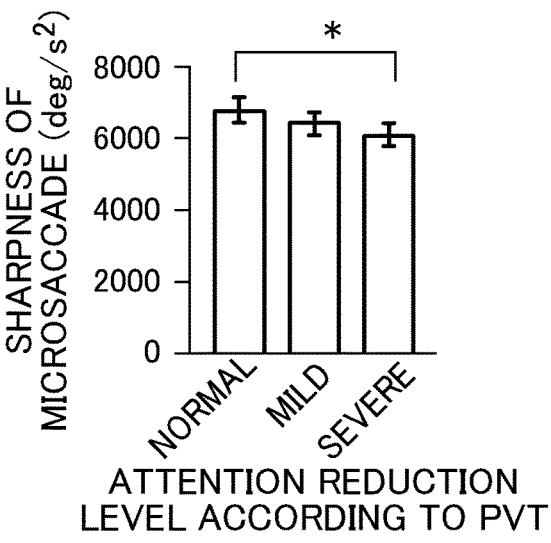
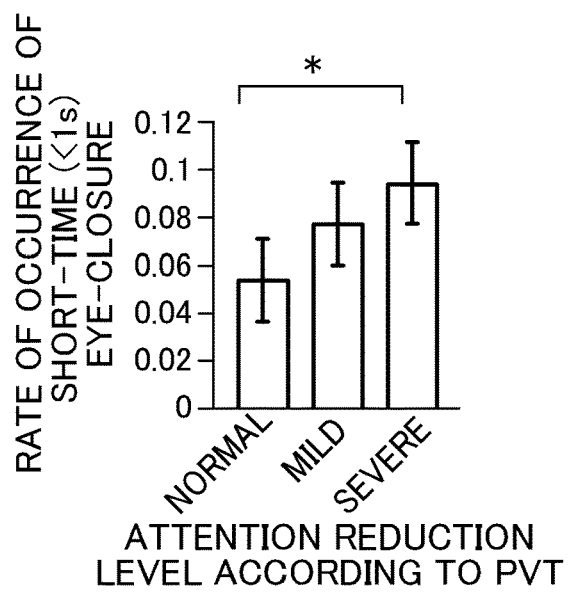
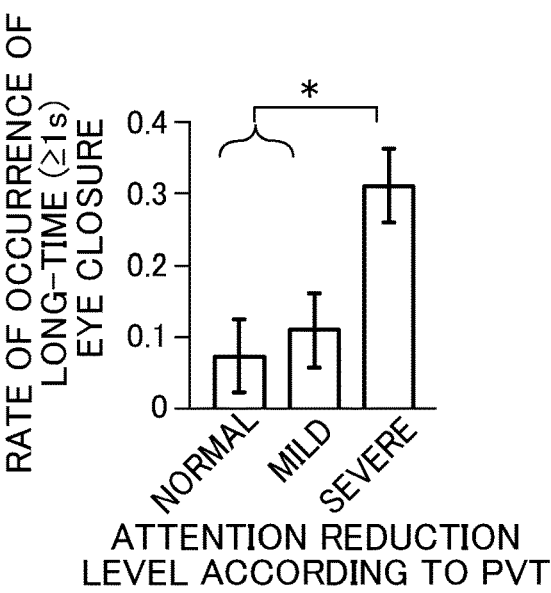
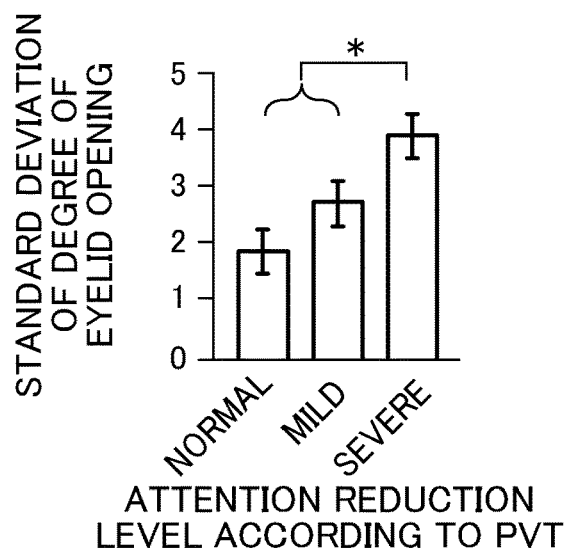

FIG.10
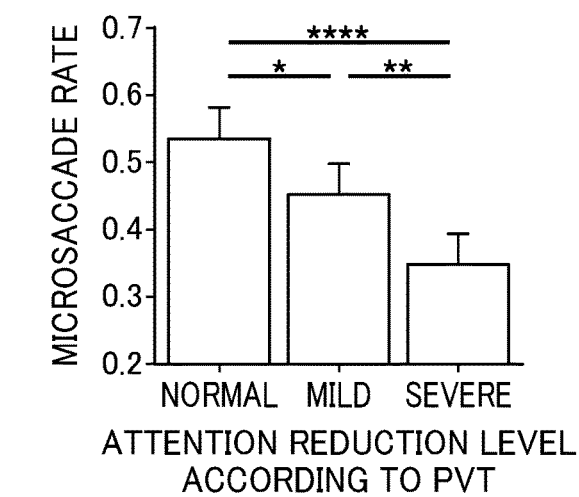
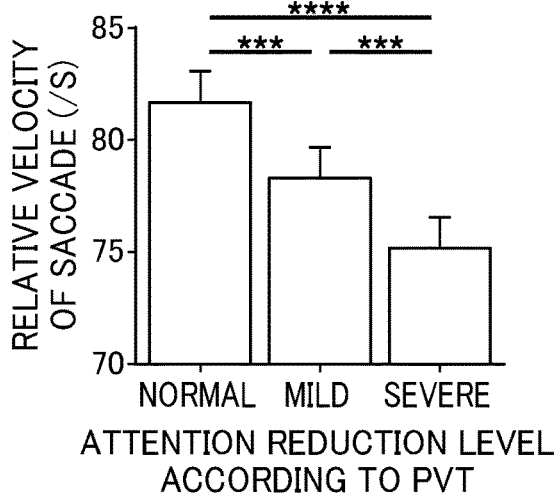
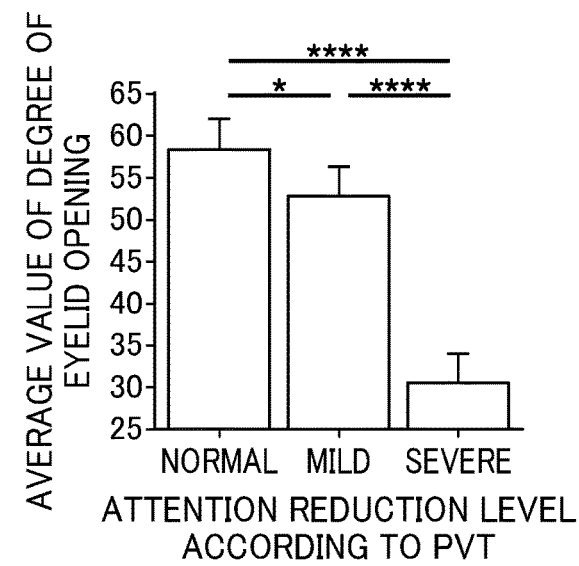
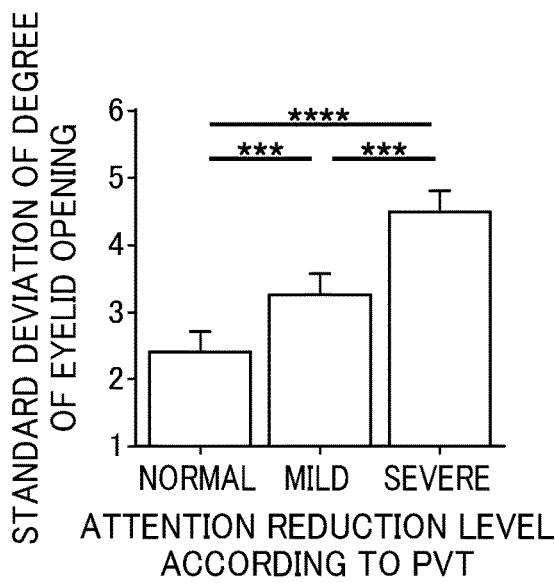
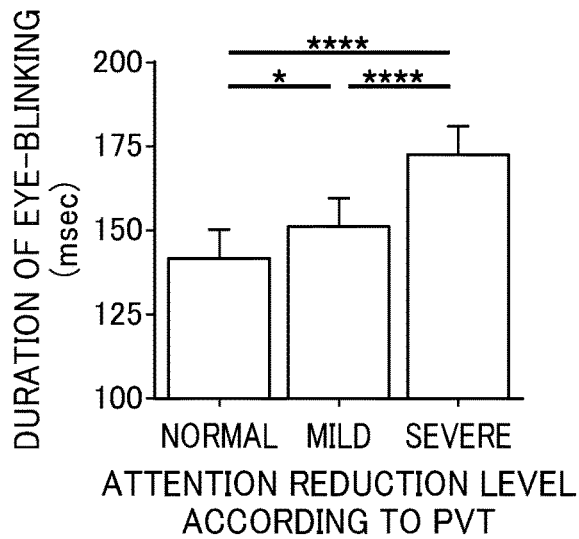
\* : $p<0.05$
\*\* : $p<0.01$
\*\*\* : $p<0.001$
\*\*\*\* : $p<0.0001$

SYSTEM, METHOD, AND PROGRAM FOR ESTIMATING REDUCED ATTENTION STATE, AND STORAGE MEDIUM STORING THE SAME PROGRAM

CROSS-REFERENCE TO RELATED APPLICATIONS

This application is a U.S. National Phase Application under 35 U.S.C. § 371 of International Application No. PCT/JP2017/042081, filed Nov. 22, 2017, which claims priority to Japanese Patent Application No. 2016-227148, filed Nov. 22, 2016, the contents of which are incorporated herein by reference in their entirety.

FIELD OF THE INVENTION

The present invention relates to an apparatus, a method and a program for estimating a reduced attention state, and a storage medium storing the program.

BACKGROUND OF THE INVENTION

Various indices and methods for assessing attention reduction due to sleepiness, fatigue or the like have been proposed.

Psychomotor vigilance test (PVT) is to measure the response (reaction time) of a subject to a stimulus (see Non-patent document 1 below). In the PVT, mild to severe attention reductions may be measured. Strictly controlled experiments have proven that the attention reduction measured in the PVT sensitively reacts to a lack of sleep or a change of biological rhythm, and for this reason the PVT is widely used as a gold standard for measuring attention reduction due to sleepiness or fatigue. Time-saving versions of the PVT have been developed. The adaptive-duration version of the PVT (PVT-A) (see the non-patent document 2 below) and the PVT-B (see the non-patent document 3 below) shortens their test times to about 6.5 and 3 minutes, respectively, while the PVT requires 10 minutes (standard test time).

Methods focusing on the movement of eyes or eyelids or the heartbeat have also been proposed. In particular, a measure referred to as PERCLOS (Percent of Eyelid Closure, meaning the percentage of the duration of the closed eye in a unit time), which uses the eye opening time and the eye closing time, is well-known (see the non-patent document 4 below). The PERCLOS has already been practically used as a doze detection technique. Furthermore, a method of estimating attention reduction based on subtle eye movements (fixational eye movements; microsaccades) has been proposed (see the patent document 1 below). The method described in the patent document 3 below estimates a state where no attention is directed to an object whereas the line of sight is directed to the object. Furthermore, various parameters concerning blinks are known to vary in relation to the sleepiness. An increase or decrease of the number of blinks, an extended time required for a blink, a decrease of the velocity of eyelid closing or eyelid opening, an extended duration of a closed eye in a blink, and the velocity of an eyeball movement are known to relate to the sleepiness.

Furthermore, a method of assessing attention using a plurality of parameters concerning eye or eyelid movements has been proposed (see the patent document 2 below). This method is referred to as Johns Sleepiness Scale (JDS). The JDS assesses sleepiness in eleven levels, from 0 to 10. It is also shown that there is a correlation between the JDS and the response time.

In short, known indices for assessing attention reduction include the duration of the eye opening section, the degree of eyelid opening, the frequency of eye-blinkings, the inverse of the relative velocity of eyelid closure, the inverse of the relative velocity of eyelid opening, the duration of an eye-blinking, the duration of a closed eye in an eye-blinking, the rate of occurrence of eye-blinkings, the frequency of microsaccades because of no attention being directed to an objected while the line of sight is directed to the object, and the relative velocity of a saccade, for example.

CITATION LIST

Patent Literature

[Patent document 1] Japanese Patent Laid-Open No. 2015-116376

[Patent document 2] Japanese Patent Laid-Open No. 2008-531142

[Non-patent document 1] Dinges D F, Powell J W. Microcomputer analyses of performance on a portable, simple visual R T task during sustained operations. Beh Res Meth Instr Comp. 1985; 17: 652-5

[Non-patent document 2] Basner M, Dinges D F. An Adaptive-Duration Version of the PVT Accurately Tracks Changes in Psychomotor Vigilance Induced by Sleep Restriction. Sleep. 2012; 35: 193-202

[Non-patent document 3] Basner M, Mollicone D, Dinges D F. Validity and Sensitivity of a Brief Psychomotor Vigilance Test (PVT-B) to Total and Partial Sleep Deprivation. Acta Astronaut. 2011; 69: 949-59

[Non-patent document 4] Wierwille W W, Ellsworth L A, Wreggit S S, Fairbanks R J, Kim C L. Research on vehicle-based driver status/performance monitoring: development, validation, and refinement of algorithms for detection of driver sleepiness. In: National Highway Traffic Safety Administration Final Report; 1994

SUMMARY OF INVENTION

Problem to be Solved by the Invention

However, the PVT has problems that a subject cannot perform another task during the test and that each test takes a long time (3 to 20 minutes), so that only a limited number of measurements may be made. Therefore, attention cannot be continuously assessed.

The PERCLOS may only detect an extreme attention reduction that causes a doze. The method described in the patent document 3 may assess a relatively mild attention reduction but cannot assess a strong sleepiness before dozing. The method using various parameters conceding a blink also cannot measure different levels of attention reduction. There is a method of measurement based on the brain wave, wearing an electrooculography is not practical for daily life.

The JDS has been shown to have a correlation with the response time. However, what has been determined is only that there is a correlation between the levels of the JDS and the response time (an index of attention), and each level of the JDS is not associated with the PVT about which much knowledge has been accumulated. Therefore, each level of the JDS cannot be described in association with the knowledge of the prior research.

Although various indices for assessing attention reduction have been known, new indices are still required.

In view of such circumstances, an object of the present invention is to provide a new index for assessing attention reduction.

Another object of the present invention is to provide a reduced attention state estimation system and a reduced attention state estimation method that may simply continuously measure various levels of attention reduction and facilitate reference to the knowledge of the PVT already accumulated in many prior researches.

Means for Solving Problem

An aspect of the present invention provides a reduced attention state estimation system, comprising: an eyeball movement and eyelid activity measurement unit that measures an eyeball movement and an eyelid activity of a subject to obtain eyeball movement and eyelid activity data; a section determination unit that determines an eye opening section, an eye closing section, an eye-blinking section and a cluster section based on the eyeball movement and eyelid activity data; an eyeball movement and eyelid activity-related information calculation unit that calculates, based on the eyeball movement and eyelid activity data, at least one of a sharpness of microsaccade for each eye opening section, a standard deviation of a degree of eyelid opening for each eye opening section and/or each eye closing section, a short-time eye-closure occurrence rate, which is a rate of occurrence of an eye closure having a duration shorter than a predetermined time, for each cluster section, and a long-time eye-closure occurrence rate, which is a rate of occurrence of an eye closure having a duration equal to or longer than the predetermined time, for each cluster section; and an attention assessment unit that determines at least one of: an attention assessment for an eye opening/cluster section, which is an eye opening section and cluster section, based on at least one of the sharpness of microsaccade, the standard deviation of the degree of eyelid opening, the short-time eye-closure occurrence rate and the long-time eye-closure occurrence rate; an attention assessment for an eye closing/cluster section, which is an eye closing section and cluster section, based on at least one of the standard deviation of the degree of eyelid opening, the short-time eye-closure occurrence rate and the long-time eye-closure occurrence rate; an attention assessment for an eye-blinking/cluster section, which is an eye-blinking section and cluster section, based on at least one of the short-time eye-closure occurrence rate and the long-time eye-closure occurrence rate; an attention assessment for an eye opening/non-cluster section, which is an eye opening section and non-cluster section, based on at least one of the sharpness of microsaccade and the standard deviation of the degree of eyelid opening; and an attention assessment for an eye closing/non-cluster section, which is an eye closing section and non-cluster section, based on at least the standard deviation of the degree of eyelid opening.

The eyeball movement and eyelid activity-related information calculation unit may further calculate, based on the eyeball movement and eyelid activity data, whether a relevant section is an eye opening section, an eye closing section or an eye-blinking section, whether an eye opening section or an eye-blinking section is included in a cluster section, whether an eye closing section is included in a cluster section, a frequency of microsaccades, a duration of an eye opening section, an average value of the degree of eyelid opening, a frequency of eye-blinkings, an inverse of a relative velocity of an eyelid closure at an eyelid closing time, an inverse of a relative velocity of an eyelid opening at an eyelid opening time, a duration of an eye-blinking, a duration of a closed eye in an eye-blinking, a rate of occurrence of eye-blinkings, and a duration of an eye closing section, and the attention assessment unit may determine at least one of: an attention assessment for the eye opening/cluster section, which is an eye opening section and cluster section, based on at least one of the sharpness of microsaccade, the standard deviation of the degree of eyelid opening, the short-time eye-closure occurrence rate and the long-time eye-closure occurrence rate, and at least one of whether a relevant section is an eye opening section, an eye closing section or an eye-blinking section, whether an eye opening section or an eye-blinking section is included in a cluster section, the frequency of microsaccades, the duration of an eye opening section, the average value of the degree of eyelid opening, the frequency of eye-blinkings, the inverse of a relative velocity of an eye closure, the inverse of a relative velocity of an eye opening, the duration of an eye-blinking, the duration of a closed eye in an eye-blinking and the rate of occurrence of eye-blinkings; an attention assessment for the eye closing/cluster section, which is an eye closing section and cluster section, based on at least one of the standard deviation of the degree of eyelid opening, the short-time eye-closure occurrence rate and the long-time eye-closure occurrence rate, and at least one of whether a relevant section is an eye opening section, an eye closing section or an eye-blinking section, whether an eye closing section is included in a cluster section, the duration of an eye closing section, the average value of the degree of eyelid opening, the frequency of eye-blinkings, the inverse of a relative velocity of an eye closure, the inverse of a relative velocity of an eye opening, the duration of an eye-blinking, the duration of a closed eye in an eye-blinking and the rate of occurrence of eye-blinkings; an attention assessment for an eye-blinking/cluster section, which is an eye-blinking section and cluster section, based on at least one of the short-time eye-closure occurrence rate and the long-time eye-closure occurrence rate, and at least one of whether a relevant section is an eye opening section, an eye closing section or an eye-blinking section, whether an eye opening section or an eye-blinking section is included in a cluster section, the frequency of eye-blinkings, the inverse of a relative velocity of an eyelid closure at an eyelid closing time, the inverse of a relative velocity of an eyelid opening at an eyelid opening time, the duration of an eye-blinking, the duration of a closed eye in an eye-blinking and the rate of occurrence of eye-blinkings; an attention assessment for an eye opening/non-cluster section, which is an eye opening section and non-cluster section, based on the sharpness of microsaccade, the standard deviation of the degree of eyelid opening, and at least one of whether a relevant section is an eye opening section, an eye closing section or an eye-blinking section, whether an eye opening section or an eye-blinking section is included in a cluster section, the frequency of microsaccades, the duration of an eye opening section and the average value of the degree of eyelid opening; an attention assessment for an eye closing/non-cluster section, which is an eye closing section and non-cluster section, based on the standard deviation of the degree of eyelid opening and at least one of whether a relevant section is an eye opening section, an eye closing section or an eye-blinking section, the duration of an eye closing section and the average value of the degree of eyelid opening; and an attention assessment for an eye-blinking/non-cluster section, which is an eye-blinking section and non-cluster section, based on at least one of whether a relevant section is an eye opening section, an eye closing section or an eye-blinking section and whether an eye opening section or an eye-blinking section is included in a cluster section.

The attention assessment may be an estimated probability of occurrence of each attention reduction level determined by a Naive Bayes estimation.

The attention assessment may be an estimated probability of occurrence of each attention reduction level per assessment time calculated based on the estimated probability of occurrence of each attention reduction level calculated for each of the eye opening/cluster section, the eye closing/cluster section, the eye-blinking/cluster section, the eye opening/non-cluster section, the eye closing/non-cluster section and the eye-blinking/non-cluster section.

A first posterior probability in the Naive Bayes estimation may be calculated based on training data derived from personal eyeball movement and eyelid activity data of the subject.

An aspect of the present invention provides a reduced attention state estimation system, comprising: an eyeball movement and eyelid activity measurement unit that measures an eyeball movement and an eyelid activity of a subject to obtain eyeball movement and eyelid activity data; a section determination unit that determines an eye opening section based on the eyeball movement and eyelid activity data; an eyeball movement and eyelid activity-related information calculation unit that calculates a sharpness of microsaccade for each eye opening section based on the eyeball movement and eyelid activity data; and an attention assessment unit that determines an attention assessment for the eye opening section based on at least the sharpness of microsaccade.

An aspect of the present invention provides a reduced attention state estimation system, comprising: an eyeball movement and eyelid activity measurement unit that measures an eyeball movement and an eyelid activity of a subject to obtain eyeball movement and eyelid activity data; a section determination unit that determines an eye opening section and/or an eye closing section based on the eyeball movement and eyelid activity data; an eyeball movement and eyelid activity-related information calculation unit that calculates a standard deviation of a degree of eyelid opening for each eye opening section and/or each eye closing section based on the eyeball movement and eyelid activity data; and an attention assessment unit that determines an attention assessment for the eye opening section and/or the eye closing section based on at least the standard deviation of the degree of eyelid opening.

An aspect of the present invention provides a reduced attention state estimation system, comprising: an eyeball movement and eyelid activity measurement unit that measures an eyeball movement and an eyelid activity of a subject to obtain eyeball movement and eyelid activity data; a section determination unit that determines a cluster section based on the eyeball movement and eyelid activity data; an eyeball movement and eyelid activity-related information calculation unit that calculates a short-time eye-closure occurrence rate, which is a rate of occurrence of an eye closure having a duration shorter than a predetermined time, and/or a long-time eye-closure occurrence rate, which is a rate of occurrence of an eye closure having a duration equal to or longer than the predetermined time, for each cluster section based on the eyeball movement and eyelid activity data; and an attention assessment unit that determines an attention assessment for the cluster section based on at least the short-time eye-closure occurrence rate and/or the long-time eye-closure occurrence rate.

An aspect of the present invention provides a reduced attention state estimation method, comprising: a section determination step of determining an eye opening section, an eye closing section, an eye-blinking section and a cluster section based on eyeball movement and eyelid activity data obtained by measuring an eyeball movement and an eyelid activity of a subject; an eyeball movement and eyelid activity-related information calculation step of calculating, based on the eyeball movement and eyelid activity data, at least one of a sharpness of microsaccade for each eye opening section, a standard deviation of a degree of eyelid opening for each eye opening section and/or each eye closing section, a short-time eye-closure occurrence rate, which is a rate of occurrence of an eye closure having a duration shorter than a predetermined time, for each cluster section, and a long-time eye-closure occurrence rate, which is a rate of occurrence of an eye closure having a duration equal to or longer than the predetermined time, for each cluster section; and an attention assessment calculation step of calculating at least one of: an attention assessment for an eye opening/cluster section, which is an eye opening section and cluster section, based on at least one of the sharpness of microsaccade, the standard deviation of the degree of eyelid opening, the short-time eye-closure occurrence rate and the long-time eye-closure occurrence rate; an attention assessment for an eye closing/cluster section, which is an eye closing section and cluster section, based on at least one of the standard deviation of the degree of eyelid opening, the short-time eye-closure occurrence rate and the long-time eye-closure occurrence rate; an attention assessment for an eye-blinking/cluster section, which is an eye-blinking section and cluster section, based on at least one of the short-time eye-closure occurrence rate and the long-time eye-closure occurrence rate; an attention assessment for an eye opening/non-cluster section, which is an eye opening section and non-cluster section, based on at least one of the sharpness of microsaccade and the standard deviation of the degree of eyelid opening; and an attention assessment for an eye closing/non-cluster section, which is an eye closing section and non-cluster section, based on at least the standard deviation of the degree of eyelid opening.

An aspect of the present invention provides a reduced attention state estimation method, comprising: a section determination step of determining an eye opening section based on eyeball movement and eyelid activity data obtained by measuring an eyeball movement and an eyelid activity of a subject; an eyeball movement and eyelid activity-related information calculation step of calculating a sharpness of microsaccade for each eye opening section based on the eyeball movement and eyelid activity data; and an attention assessment step of determining an attention assessment for the eye opening section based on at least the sharpness of microsaccade.

An aspect of the present invention provides a reduced attention state estimation method, comprising: a section determination step of determining an eye opening section and/or an eye closing section based on eyeball movement and eyelid activity data obtained by measuring an eyeball movement and an eyelid activity of a subject; an eyeball movement and eyelid activity-related information calculation step of calculating a standard deviation of a degree of eyelid opening for each eye opening section and/or each eye closing section based on the eyeball movement and eyelid activity data; and an attention assessment step of determining an attention assessment for the eye opening section and/or the eye closing section based on at least the standard deviation of the degree of eyelid opening.

An aspect of the present invention provides a reduced attention state estimation method, comprising: a section determination step of determining a cluster section based on eyeball movement and eyelid activity data obtained by measuring an eyeball movement and an eyelid activity of a subject; an eyeball movement and eyelid activity-related information calculation step of calculating a short-time eye-closure occurrence rate, which is a rate of occurrence of an eye closure having a duration shorter than a predetermined time, and/or a long-time eye-closure occurrence rate, which is a rate of occurrence of an eye closure having a duration equal to or longer than the predetermined time, for each cluster section based on the eyeball movement and eyelid activity data; and an attention assessment step of determining an attention assessment for the cluster section based on at least the short-time eye-closure occurrence rate and/or the long-time eye-closure occurrence rate.

An aspect of the present invention provides a program that makes a computer perform any of the reduced attention state estimation methods described above.

An aspect of the present invention provides a computer-readable storage medium storing the program described above.

An aspect of the present invention provides a reduced attention state estimation system, comprising: an eyeball movement and eyelid activity measurement unit that measures an eyeball movement and an eyelid activity of a subject to obtain eyeball movement and eyelid activity data; a section determination unit that determines an eye opening section, an eye closing section, an eye-blinking section and a cluster section based on the eyeball movement and eyelid activity data; an eyeball movement and eyelid activity-related information calculation unit that calculates, based on the eyeball movement and eyelid activity data, at least one of a microsaccade rate for each eye opening section, a relative velocity of a saccade for each eye opening section, a standard deviation of a degree of eyelid opening for each eye opening section and/or each eye closing section, an average value of the degree of eyelid opening for each eye opening section and/or each eye closing section, and a duration of an eye-blinking for each cluster section; and an attention assessment unit that determines at least one of: an attention assessment for an eye opening/cluster section, which is an eye closing section and cluster section, based on at least one of the microsaccade rate, the relative velocity of a saccade, the standard deviation of the degree of eyelid opening, the average value of the degree of eyelid opening and the duration of an eye-blinking; an attention assessment for an eye closing/cluster section, which is an eye closing section and cluster section, based on at least one of the standard deviation of the degree of eyelid opening, the average value of the degree of eyelid opening and the duration of an eye-blinking; an attention assessment for an eye-blinking/cluster section, which is an eye-blinking section and cluster section, based on at least the duration of an eye-blinking; an attention assessment for an eye opening/non-cluster section, which is an eye opening section and non-cluster section, based on at least one of the microsaccade rate, the relative velocity of a saccade, the standard deviation of the degree of eyelid opening and the average value of the degree of eyelid opening; and an attention assessment for an eye closing/non-cluster section, which is an eye closing section and non-cluster section, based on at least one of the standard deviation of the degree of eyelid opening and the average value of the degree of eyelid opening, wherein the attention assessment is any of three or more levels of attention reduction.

Effect of the Invention

According to the present invention, which uses new indices, the reduced attention state may be efficiently estimated.

In addition, the present invention with the configurations described above may provide a reduced attention state estimation system and a reduced attention state estimation method that may simply continuously measure various levels of attention reduction and facilitate reference to the knowledge of the PVT already accumulated in many prior researches.

BRIEF DESCRIPTION OF THE DRAWINGS

FIG. 2 shows graphs showing results of comparison between levels of attention reduction regarding new indices of attention according to the present invention.

FIG. 10 shows a result of comparison, between the levels of attention reduction (normal, mild and severe), of the microsaccade rate, the relative velocity of a saccade, the average value of the degree of eyelid opening, the standard deviation of the degree of eyelid opening and the duration of an eye-blinking.

DESCRIPTION OF EMBODIMENTS

Figure 1:
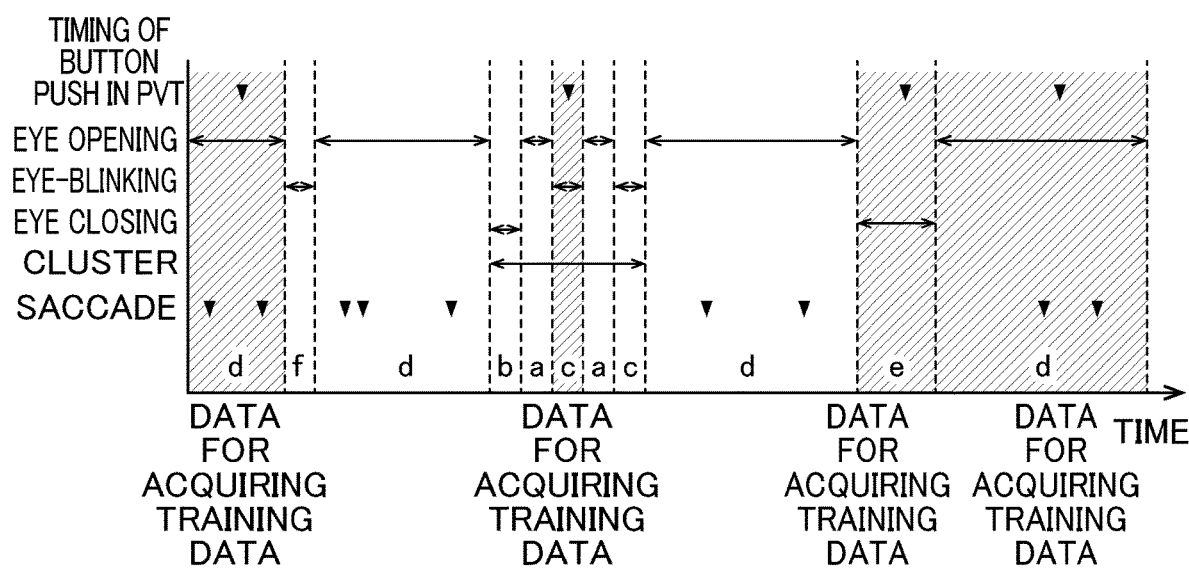
FIG. 1 is a diagram showing an example of an eye opening section, an eye closing section, an eye-blinking section and a cluster section.

In the following, embodiments of the present invention will be described.

First Embodiment

As new indices for assessing attention reduction, the inventors have found frequency of microsaccades due to sleepiness, sharpness of microsaccade, standard deviation of the degree of eyelid opening, rate of occurrence of eye closures whose duration is shorter than a predetermined time, and rate of occurrence of eye closures whose duration is equal to or longer than the predetermined time. An experiment conducted by the inventors to prove the relationship between the new indices and the attention measured in the PVT will be described below.

As subjects, eight adult males (of ages of 20 to 47, 36.6±10.2[SD]) who were healthy and had no sleep disorder were chosen.

To control the hours of sleep and the sleep wake rhythm of the subjects before the experiment, the sleep wake pattern of the subjects was recorded at home with sleep diary and an actigraph from a week before the experiment to the day of the experiment. The subjects were instructed to go to bed between 9 pm and 1 am, get up between 6 am and 9 am and have seven or more hours of sleep.

The subjects were divided into two groups each containing four subjects for the experiment. The subjects were instructed not to take caffeine and to refrain from hard exercise after the subjects got up on the day of the experiment until they came to the laboratory. The subjects came to the laboratory at 8 pm. After the subjects came to the laboratory, the sleep wake pattern and the activity during daytime of the subjects for the week were checked, and only the subjects whose patterns matched those instructed by the experimenters were adopted for the experiment.

On the first night, two of the four subjects in each group had ten hours of sleep from 10 pm. Since 8 am, the subjects continued to stay awake for 38 hours and took the PVT in the manner described below. On the third night, the subjects had 10 hours of recovery sleep from 10 pm and then took the PVT again from 8 am to 12 am, and the experiment was ended. During the waking hours, the subjects took a meal of 200 kcal every two hours. The subjects were free to drink water (mineral water).

The schedule described above was shifted by one hour for the remaining two of the four subjects in each group.

During the waking hours, the subjects took one PVT every two hours. In each PVT, movements of the eyeballs and eyelids of the subjects were measured to obtain various kinds of eyeball movement and eyelid activity data.

The PVT taken by the subjects was in conformity with the non-patent document 3 and a document (Basner, M., & Dinges, D. F. Maximizing sensitivity of the psychomotor vigilance test (PVT) to sleep loss. Sleep 2011, 34: 581-91) describing a method of conducting the PVT in detail. The PVT taken by the subjects requires the subjects to press the button as early as possible to respond a millisecond counter displayed at random time intervals from 2 to 10 seconds on a screen of a personal computer. When the button is pressed, the counter stops, and a feedback on the response time is given for 1 second. The counter that is incremented in milliseconds is shown in a rectangular frame. If any response occurs when no stimulus is given or occurs within less than 100 ms from a stimulus, "FS" (as an abbreviation of False Start) is shown as a feedback for 1 second. If no response occurs for 30000 ms or more from a stimulus, a timeout occurs. If a timeout occurs, "OVERRUN" is shown for 1 second as a feedback. At the same time, an acoustic stimulus is also given to the subject. In this experiment, the subjects took one PVT every two hours, and each PVT took twenty minutes.

The eyeball movement and eyelid activity data on the subject was obtained by measuring movements of the eyeballs and eyelids of the subject with an eye camera (NAC eye mark recorder EMR-9, manufactured by nac Image Technology Inc.) and an electrooculography (Neurofax digital electrooculography system EEG-1200, manufactured by Nihon Kohden Corporation) worn by the subject.

To obtain the eyeball movement data, an eyeball rotation angle of the eyes about each of an X-axis and a Y-axis was recorded with the eye camera. The coordinates of the position of the eyes were sampled at 240.21 Hz, the obtained rotation angles $X_i$ and $Y_i$ of the eyeballs about the X-axis and the Y-axis were passed through a high-cut filter of 60 Hz, and a velocity $V_i$ (°/second) at a time i was determined according to the following formula. In the formula, T denotes a sampling interval (=1/240.21 seconds), and m denotes a differential point count (=1).

$$V_i = \frac{\sqrt{(X_{i+m} - X_{i-m})^2 + (Y_{i+m} - Y_{i-m})^2}}{2mT}$$

Analysis was made of the eyeball movement of the left eye. An eyeball movement that satisfied all the conditions described below was determined as a saccade: (1) the magnitude of a vector (Xi, Yi) of the eyeball rotation angle from a point of change of a velocity waveform associated with a start of an eyeball movement (a point at which the velocity was the same as or slower than a peak velocity of 25°/second and was the same or slower than the velocity at the adjoining preceding point and which was the closest to the point of the peak velocity) to a point of change of the velocity waveform associated with an end of the eyeball movement (a point at which the velocity was the same or slower than a maximum peak velocity of the eyeball movement and was the same as or slower than the velocity at the adjoining following point and which was the closest to the point of the maximum peak velocity) was same as or greater than 0.1°, (2) the magnitude of both the eyeball rotation angles Xi and Yi from the point of change of the velocity waveform associated with the start of the eyeball movement to the point of change of the velocity waveform associated with the end of the eyeball movement was the same as or greater than 0.1°, (3) the duration between the point of change of the velocity waveform associated with the start of the eyeball movement and the point of change of the velocity waveform associated with the end of the eyeball movement was the same as or longer than 10 ms, (4) the maximum peak velocity was the same as or higher than 25°/second and lower than 1000°/second, and (5) the velocity did not become slower than the velocities at the points of change between the point of change of the velocity waveform associated with the start of the eyeball movement and the point of change of the velocity waveform associated with end of the eyeball movement. Of the eyeball movements determined as a saccade, any eyeball movement for which the magnitude of the vector (Xi, Yi) of the eyeball rotation angle was the same as or smaller than 1° was determined as a microsaccade.

Furthermore, the eye camera was used to obtain the degree of eyelid opening, which is one of the eyelid activity data. To obtain the data on the degree of eyelid opening, the eyes were imaged at 30 Hz with the eye camera, and the images were recorded. As with the eyeball movement, analysis was made of the degree of eyelid opening of the left eye. In an image of the left eye, the number of pixels was measured every 100 ms along the longest line vertically connecting the upper eyelid and the lower eyelid. At an arbitrary point in time during the measurement of the distance between the upper eyelid and the lower eyelid, the diameter of the iris was measured in units of number of pixels. The distance between the upper eyelid and the lower eyelid divided by the diameter of the iris was designated as the degree of eyelid opening. For a section in which a blink occurred whose duration from the time when the eye started closing to the time when the eye opened again was less than 500 ms as described later, the degree of eyelid opening was not determined, and the section was designated as an eye-blinking section.

Furthermore, the electrooculography was used to determine the eye potential between electrodes attached above and below the orbit of the left eye, and data on eye-blinkings (blinks), which is one of the eyelid activity data, was derived from the eye potential. A reason why the data on eye-blinkings was also derived from the eye potential was that the sampling frequency for the degree of eyelid opening derived from the images of the eye was low. The eye potential was determined by measuring an electrooculogram at a sampling frequency of 200 Hz and calculating a bipolar derivation for the two electrodes above and below the orbit of the left eye. A low-cut filter of 0.05 Hz and a high-cut filter of 30 Hz were used to cut off low frequency components and high frequency components of the eye potential. A point in time when the amount of change of the eye potential (the variation in amplitude of the eye potential within ±5 measurement points (±25 ms) with respect to a measurement point) became equal to or greater than a threshold (+20 µV/50 ms) was designated as a starting point of an eyelid closing phase, a point in time when the amount of change became equal to or smaller than the threshold (+20 µV/50 ms) was designated as an end point of the eyelid closing phase, a point in time when the amount of change became equal to or smaller than a threshold (−20 µV/50 ms) was designated as a starting point of an eyelid opening phase, and a point in time when the amount of change became equal to or greater than the threshold (−20 µV/50 ms) was designated as an end point of the eyelid opening phase. A change of the eye potential in the period from the starting point of the eyelid closing phase to the end point of the eyelid opening phase that satisfied all the conditions described below was determined to indicate an eye-blinking (blink): (1) the starting point of the eyelid closing phase preceded the end point of the eyelid closing phase, the end point of the eyelid closing phase preceded the starting point of the eyelid opening phase, and the starting point of the eyelid opening phase preceded the end point of the eyelid opening phase, (2) the absolute value of the amount of change in the period from the end point of the eyelid closing phase to the starting point of the eyelid opening phase was not greater than the absolute value of the amount of change at the end point of the eyelid closing phase or the starting point of the eyelid opening phase, (3) the amount of change did not become smaller than the threshold (+20 µV/50 ms) in the period from the starting point of the eyelid closing phase to the end point of the eyelid closing phase, (4) the amount of change did not become greater than the threshold (−20 µV/50 ms) in the period from the starting point of the eyelid opening phase to the end point of the eyelid opening phase, (5) the amplitude of the eyelid closing phase was equal to or greater than a half of the amplitude of the eyelid opening phase, (6) the amplitude of the eyelid opening phase was equal to or greater than a half of the amplitude of the eyelid closing phase, (7) the duration from the starting point of the eyelid closing phase to the end point of the eyelid opening phase was equal to or longer than 50 ms and equal to or shorter than 500 ms, and both the amplitude of the eyelid closing phase and the amplitude of the eyelid opening phase were equal to or greater than 80 µV.

Based on the obtained eyeball movement and eyelid activity data, an eye opening section, an eye closing section, an eye-blinking section, and a cluster section were determined. Specifically, a section in which a blink occurred whose duration from the time when the eye started closing to the time when the eye opened again, which was determined from a series of images of the left eye recorded with the eye camera, was less than 500 ms was designated as the eye-blinking section. Sections in which no blink occurred were classified as the eye closing section or the eye opening section. A state in which the degree of eyelid opening was equal to or higher than 20% was designated as an eye opening state, and a section in which the eye opening state occurred was designated as the eye opening section. A state in which the degree of eyelid opening was lower than 20% was designated as an eye closing state, and a section in which the eye closing state occurred was designated as the eye closing section.

In addition to the state classification as the eye opening state, the eye closing state or the eye-blinking state, states were classified according to whether a cluster of blinks or eye closures were occurring or not. If the duration of an eye opening section between blinks or eye closures is less than 1 second, a section from the point in time when the blink or eye closure preceding the eye opening started to the point in time when the blink or eye closure following the eye opening ended was designated as the cluster section. If successive cluster sections occurred, the successive cluster sections were regarded as one cluster section. The other sections than the cluster sections were designated as non-cluster sections.

FIG. 1 shows an example of the eye opening section, the eye closing section, the eye-blinking section, and the cluster section.

In addition, based on the determined section types and the obtained eyeball movement and eyelid activity data, the following items of information concerning the eyeball movement and eyelid activity were determined.

(1) Duration of Eye Opening Section

The time from the start of the eye opening to the end of the eye opening in the eye opening section is designated as the duration of the eye opening section. The eye opening section is defined as a section that contains successive measurement points in time at which the degree of eyelid opening is equal to or higher than 20%. The first measurement point in time at which the degree of eyelid opening is equal to or higher than 20% is designated as the start of the eye opening, and the measurement point in time immediately preceding the first measurement point in time in the following eye-blinking section or eye closing section (in which the degree of eyelid opening is lower than 20%) is designated as the end of the eye opening.

(2) Frequency of Microsaccades

As described above, the microsaccade is defined as a saccade for which the magnitude of the vector of the eyeball rotation angle is equal to or smaller than 1°. The frequency of microsaccades is the value obtained by dividing the number of microsaccades occurring in an eye opening section by the duration of the eye opening section. It should be noted that, the sections for which the eyeball movement failed to be successfully measured due to noise were excluded, and the frequency of microsaccades was determined only for the sections for which the eyeball movement was able to be measured. Any eye opening section in which at least one saccade occurred was designated as a saccade section (see FIG. 1).

(3) Sharpness of Microsaccade

The sharpness of microsaccade is the value obtained by dividing the maximum rotational angular velocity of the eyeball movement in a microsaccade by the duration of the microsaccade (the duration from the point in time when the maximum acceleration is reached after the microsaccade starts to the point in time when the minimum acceleration is reached before the microsaccade ends).

(4) Average Value of Degree of Eyelid Opening

The average value of the degree of eyelid opening in each eye opening section or each eye closing section is defined as an average value of the degrees of eyelid opening at the measurement points in time in the eye opening section or eye closing section. As described above, the degree of eyelid opening is the rate obtained by dividing the distance between the upper eyelid and the lower eyelid by the diameter of the iris. In this experiment, the degree of eyelid opening was calculated every 0.1 seconds, and the average value thereof was determined.

(5) Standard Deviation of Degree of Eyelid Opening

The standard deviation of the degree of eyelid opening in each eye opening section or each eye closing section is defined as a standard deviation of the degrees of eyelid opening at the measurement points in time in the eye opening section or eye closing section. As described above, the degree of eyelid opening is the rate obtained by dividing the distance between the upper eyelid and the lower eyelid by the diameter of the iris. In this experiment, the degree of eyelid opening was calculated every 0.1 seconds, and the standard deviation thereof was determined.

(6) Frequency of Eye-Blinkings

The frequency of eye-blinkings is the value obtained by dividing the number of eye-blinkings occurring in each cluster section by the duration of the cluster section.

In this experiment, the number of eye-blinkings was determined based on the eye potential as described above.

(7) Inverse of Relative Velocity of Eyelid Closure at an Eyelid Closing Time

In a cluster section in which an eye-blinking section is included, the phase in the blink in which the eyelid closes is referred to as an eyelid closing time (phase), and the inverse of the relative velocity of an eyelid closure at an eyelid closing time is the value obtained by dividing the amplitude of the eyelid closure by the velocity of the eyelid closure. The phase in which the eyelid closes (eyelid closing phase) is defined as a phase from the point in time when the amount of change of the eye potential (the variation in amplitude of the eye potential within ±5 measurement points (±25 ms) with respect to a measurement point) becomes equal to or greater than the threshold (+20 µV/50 ms) (the starting point of the eyelid closing phase) to the point in time when the amount of change of the eye potential becomes equal to or smaller than the threshold (20 µV/50 ms) (the end point of the eyelid closing phase). The maximum amplitude of the eye potential during an eye-blinking minus the amplitude of the eye potential at the starting point of the eyelid closing phase is referred to as an eyelid closing amplitude, and the maximum velocity (µV/50 ms) in the period from the starting point of the eyelid closing phase to the end point of the eyelid closing phase is referred to as an eyelid closing velocity.

(8) Inverse of Relative Velocity of Eyelid Opening at an Eyelid Opening Time

In a cluster section in which an eye-blinking section is included, the phase in the blink in which the eyelid opens is referred to as an eyelid opening time (phase), and the inverse of the relative velocity of an eyelid opening at an eyelid opening time is as the value obtained by dividing the amplitude of the eyelid opening by the velocity of the eyelid opening. The phase in which the eyelid opens (eyelid opening phase) is defined as a phase from the point in time when the amount of change of the eye potential (the variation in amplitude of the eye potential within ±5 measurement points (+25 ms) with respect to a measurement point) becomes equal to or smaller than the threshold (−20 µV/50 ms) (the starting point of the eyelid opening phase) to the point in time when the absolute value of the amount of change of the eye potential becomes equal to or greater than the threshold (−20 µV/50 ms) (the end point of the eyelid opening phase). The maximum amplitude of the eye potential during an eye-blinking minus the amplitude of the eye potential at the end point of the eyelid opening phase is referred to as an eyelid opening amplitude, and the maximum velocity (µV/50 ms) in the period from the starting point of the eyelid opening phase to the end point of the eyelid opening phase is referred to as an eyelid opening velocity.

(9) Duration of Eye-Blinking

In a cluster section in which an eye-blinking section is included, the length of time from the point in time when the amplitude of the eye potential becomes greater than 50% of the eyelid closing amplitude to the point in time when the amplitude of the eye potential becomes smaller than 50% of the eyelid closing amplitude is referred to as a duration of an eye-blinking.

(10) Duration of Closed Eye in Eye-Blinking

In a cluster section in which an eye-blinking section is included, the time for which an eye is kept closed in an eye-blinking is referred to as a duration of a closed eye in the eye-blinking. The closed eye in eye-blinking is defined as a state of an eye in which the amplitude of the eye potential is greater than 90% of the eyelid closing amplitude.

(11) Eye-Blinking Occurrence Rate

In a cluster section in which an eye-blinking section is included, the eye-blinking occurrence rate is the rate obtained by dividing the cumulative time of eye-blinkings by the duration of the cluster section. In this experiment, as with the determination of the eye-blinking section described above, it was determined that an eye-blinking occurred if a blink occurred whose duration from the time when the eye started closing to the time when the eye opened again, which was determined from a series of images of the left eye recorded with the eye camera, was less than 500 ms. An eye closure cannot be determined based on the eye potential and therefore is determined based on the degree of eyelid opening determined from the images of the left eye recorded with the eye camera as described above. However, for the same eyelid activity, depending on the sampling frequency or the way of recording (whether the potential is recorded or the images themselves are recorded), the result of the determination of an eye-blinking based on the eye potential may not perfectly match the result of the determination of a blink based on the degree of eyelid opening. Therefore, an eyelid activity determined as an eye-blinking based on the eye potential may be determined as a short-time eye closure described later based on the degree of eyelid opening. This is the reason why the eye-blinking was determined based on the series of images of the left eye.

(12) Rate of Occurrence of Eye Closures Whose Duration is Shorter Than Predetermined Time (Short-Time Eye Closure Occurrence Rate)

In a cluster section in which an eye-blinking section is included, the proportion of the total duration of the eye closures having a duration shorter than a predetermined time in the duration of the cluster section is referred to as a short-time eye-closure occurrence rate. In this experiment, the predetermined time was 1 second.

(13) Rate of Occurrence of Eye Closures Whose Duration is Equal to or Longer than Predetermined Time (Long-Time Eye Closure Occurrence Rate)

In a cluster section in which an eye-blinking section is included, the proportion of the total duration of the eye closures having a duration equal to or longer than a predetermined time in the duration of the cluster section is referred to as a long-time eye-closure occurrence rate. In this experiment, the predetermined time was 1 second.

(14) Duration of Eye Closing Section

The length of time from the start of the eye closure to the end of the eye closure in an eye closing section is referred to as a duration of the eye closing section. As with the duration of the eye opening section, the eye closing section is defined as a section that contains successive measurement points at which the degree of eyelid opening is lower than 20%. The first measurement point at which the degree of eyelid opening is lower than 20% is designated as the start of the eye closing, and the measurement point immediately preceding the first measurement point in the following eye-blinking section or eye opening section (in which the degree of eyelid opening is equal to or higher than 20%) is designated as the end of the eye closing.

As described above, the response time (RT) to each trial in the PVT indicates the degree of attention reduction. The response time is classified into three levels of attention reduction: $100 \text{ ms} \leq RT < 300 \text{ ms}$, $300 \text{ ms} \leq RT < 500 \text{ ms}$, and $500 \text{ ms} \leq RT$, which are referred to as "normal attention reduction level", "mild" and "severe", respectively.

It should be noted that any trial for which the response time was less than 100 ms ($RT < 100$ ms) or the response to which was FS (False Start) was excluded because such responses were rare.

Table 1 shows a relationship between each item of information concerning the eyeball movement and eyelid activity at the point in time when the response to each trial in the PVT occurs and the attention measured in the PVT. The relationship is determined by comparison of the eyeball movement and eyelid activity at the point in time at which the response to each trial in the PVT occurs between the levels of attention reduction (normal, mild and severe). FIG. 2 shows a result of comparison, between the levels of attention reduction (normal, mild and severe), of the frequency of microsaccades due to sleepiness, the sharpness of microsaccade, the standard deviation of the degree of eyelid opening, the short-time eye-closure occurrence rate and the long-time eye-closure occurrence rate, of the items of information concerning the eyeball movement and eyelid activity, at the point in time when the response to each trial in the PVT occurred. As can be seen from Table 1 and FIG. 2, in addition to the duration of the eye opening section, the degree of eyelid opening, the frequency of eye-blinkings, the inverse of the relative velocity of an eyelid closure at an eyelid closing time, the inverse of the relative velocity of an eyelid opening at an eyelid opening time, the duration of an eye-blinking, the duration of a closed eye in an eye-blinking, and the eye-blinking occurrence rate, which are conventionally known indices of attention level, the frequency of microsaccades due to sleepiness, the sharpness of microsaccade, the standard deviation of the degree of eyelid opening, the short-time eye-closure occurrence rate and the long-time eye-closure occurrence rate may be used as indices of attention.

TABLE 1

| SECTION (EYE OPENING/EYE CLOSING/EYE-BLINKING) | STATE (PRESENCE OR ABSENCE OF CLUSTER) | INDEX OF EYEBALL MOVEMENT OR EYELID ACTIVITY | CORRELATION WITH ATTENTION MEASURED IN PVT | |
|---|---|---|---|---|
| EYE OPENING | PRESENCE OR ABSENCE OF CLUSTER | FREQUENCY OF MICROSACCADES (TIMES/MINUTE) | CORRELATED | (p = 0.01) |

TABLE 1-continued

| SECTION (EYE OPENING/EYE CLOSING/EYE-BLINKING) | STATE (PRESENCE OR ABSENCE OF CLUSTER) | INDEX OF EYEBALL MOVEMENT OR EYELID ACTIVITY | CORRELATION WITH ATTENTION MEASURED IN PVT | |
| --- | --- | --- | --- | --- |
| | | MICROSACCADE SUDDENNESS (deg/s$^2$) | CORRELATED | ($p = 0.03$) |
| | | DURATION OF EYE OPENING SECTION | CORRELATED | ($p = 0.03$) |
| EYE OPENING OR EYE CLOSING | PRESENCE OR OF ABSENCE CLUSTER | DEGREE OF EYELID OPENING | CORRELATED | ($p < 0.0001$) |
| | | STANDARD DEVIATION OF DEGREE OF EYELID OPENING | CORRELATED | ($p = 0.0001$) |
| EYE CLOSING | PRESENCE OR ABSENCE OF CLUSTER | DURATION OF EYE CLOSING SECTION | NOT CORRELATED | (n.s.) |
| EYE OPENING/EYE CLOSING/EYE-BLINKING | PRESENCE OF CLUSTER | FREQUENCY OF EYE-BLINKINGS | CORRELATED | ($p = 0.003$) |
| | | INVERSE OF RELATIVE VELOCITY OF EYE CLOSURE | CORRELATED | ($p = 0.0003$) |
| | | INVERSE OF RELATIVE VELOCITY OF EYE OPENING | CORRELATED | ($p = 0.003$) |
| | | DURATION OF CLOSED EYE IN EYE-BLINKING | CORRELATED | ($p < 0.0001$) |
| | | DURATION OF EYE-BLINKING | CORRELATED | ($p < 0.0001$) |
| | | RATE OF OCCURRENCE OF EYE-BLINKINGS | CORRELATED | ($p < 0.0001$) |
| | | RATE OF OCCURRENCE OF SHORT TIME (<1 s) EYE CLOSURE | CORRELATED | ($p = 0.0031$) |
| | | RATE OF OCCURRENCE OF LONG TIME (≥1 s) EYE CLOSURE | CORRELATED | ($p = 0.0005$) |

Figure 3:
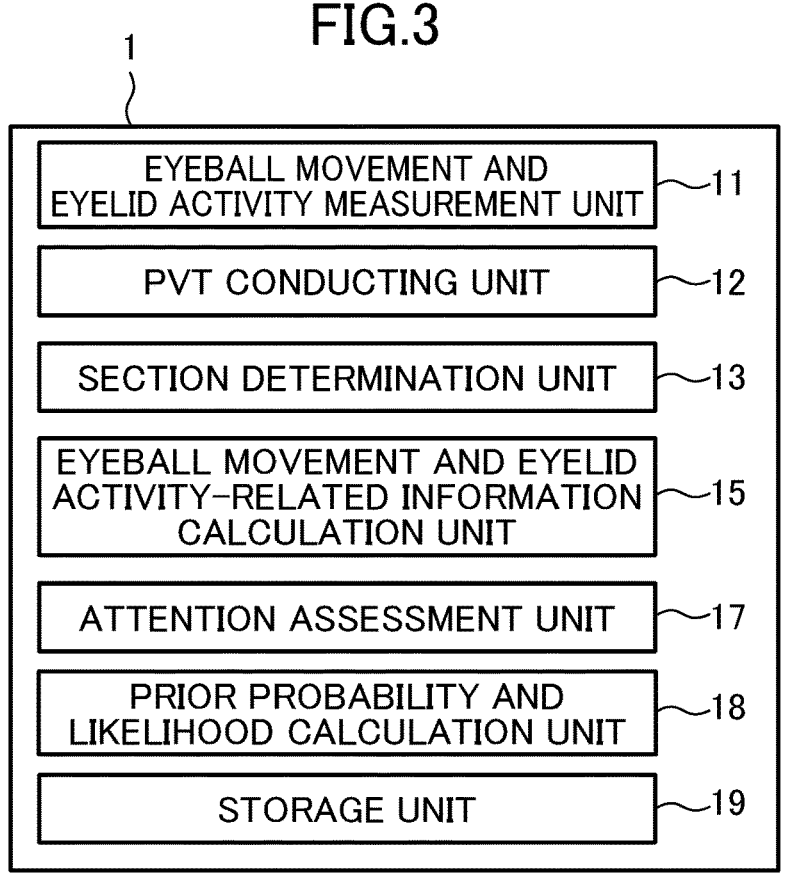
FIG. 3 is a diagram showing a general configuration of a reduced attention state estimation system according to a first embodiment of the present invention.

FIG. 3 is a diagram showing a general configuration of a reduced attention state estimation system according to the first embodiment of the present invention.

As shown in FIG. 3, the reduced attention state estimation system 1 according to this embodiment includes an eyeball movement and eyelid activity measurement unit 11, a PVT conducting unit 12, a section determination unit 13, an eyeball movement and eyelid activity-related information calculation unit 15, an attention assessment unit 17, an prior probability and likelihood calculation unit 18, and a storage unit 19.

The eyeball movement and eyelid activity measurement unit 11 measures a movement of an eyeball or eyelid of a subject with a camera or sensor to obtain various kinds of eyeball movement and eyelid activity data.

The PVT conducting unit 12 conducts the PVT on the subject. The PVT conducting unit 12 further measures the response time of the subject to a trial in the PVT and stores the response time in the storage unit 19.

The section determination unit 13 determines an eye opening section, an eye closing section, an eye-blinking section and a cluster section based on the eyeball movement and eyelid activity data obtained by the eyeball movement and eyelid activity measurement unit 11.

The eyeball movement and eyelid activity-related information calculation unit 15 calculates various kinds of information concerning the eyeball movement and eyelid activity based on the eyeball movement and eyelid activity data obtained by the eyeball movement and eyelid activity measurement unit 11 and the types of the sections determined by the section determination unit 13.

More specifically, the eyeball movement and eyelid activity-related information calculation unit 15 calculates whether a relevant section is the eye opening section, the eye closing section, or the eye-blinking section, whether an eye closing section is included in a cluster section, whether an eye opening section or eye-blinking section is included in a cluster section, the duration of eye opening, the frequency of microsaccades and the sharpness of microsaccade for the eye opening section, the average value of the degree of eyelid opening and the standard deviation of the degree of eyelid opening for the eye opening section and the eye closing section, the duration of eye closure for the eye closing section, and the frequency of eye-blinkings, the inverse of the relative velocity of an eyelid closure at an eyelid closing time, the inverse of the relative velocity of an eyelid opening at an eyelid opening time, the duration of an eye-blinking, the duration of a closed eye in an eye-blinking, the eye-blinking occurrence rate, the short-time eye-closure occurrence rate and the long-time eye-closure occurrence rate for the cluster section.

The attention assessment unit 17 calculates an attention assessment based on the various kinds of information concerning the eyeball movement and eyelid activity calculated by the eyeball movement and eyelid activity-related information calculation unit 15. In this embodiment, an estimated probability of occurrence of each attention reduction level and an estimated probability of occurrence of each attention reduction level per assessment time are calculated according to the Naive Bayes estimation.

The prior probability and likelihood calculation unit 18 calculates the first prior probability in the Naive Bayes estimation performed by the attention assessment unit 17, the likelihood for the information concerning the eyeball movement and eyelid activity, and a probability density function used for calculating the likelihood, and stores them in the storage unit 19.

The storage unit 19 stores various kinds of data.

Figure 4:
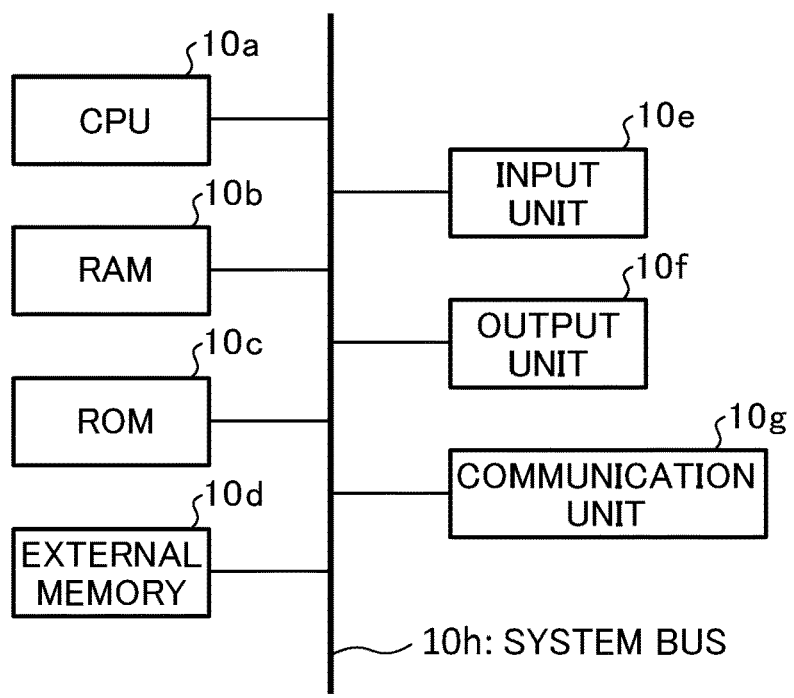
FIG. 4 is a diagram showing an example of a hardware configuration of the reduced attention state estimation system according to the first embodiment of the present invention.

FIG. 4 is a diagram showing an example of a hardware configuration of the reduced attention state estimation system 1 according to an embodiment of the present invention. The reduced attention state estimation system 1 includes a CPU 10a, a RAM 10b, a ROM 10c, an external memory 10d, an input unit 10e, an output unit 10f and a communication unit 10g. The RAM 10b, the ROM 10c, the external memory 10d, the input unit 10e, the output unit 10f and the communication unit 10g are connected to the CPU 10a via a system bus 10h.

The units in the reduced attention state estimation system shown in FIG. 4 is implemented by various programs stored in the ROM 10c or the external memory 10d using the CPU 10a, the RAM 10b, the ROM 10c, the external memory 10d, the input unit 10e, the output unit 10f, the communication unit 10g and the like as resources.

Figure 5:
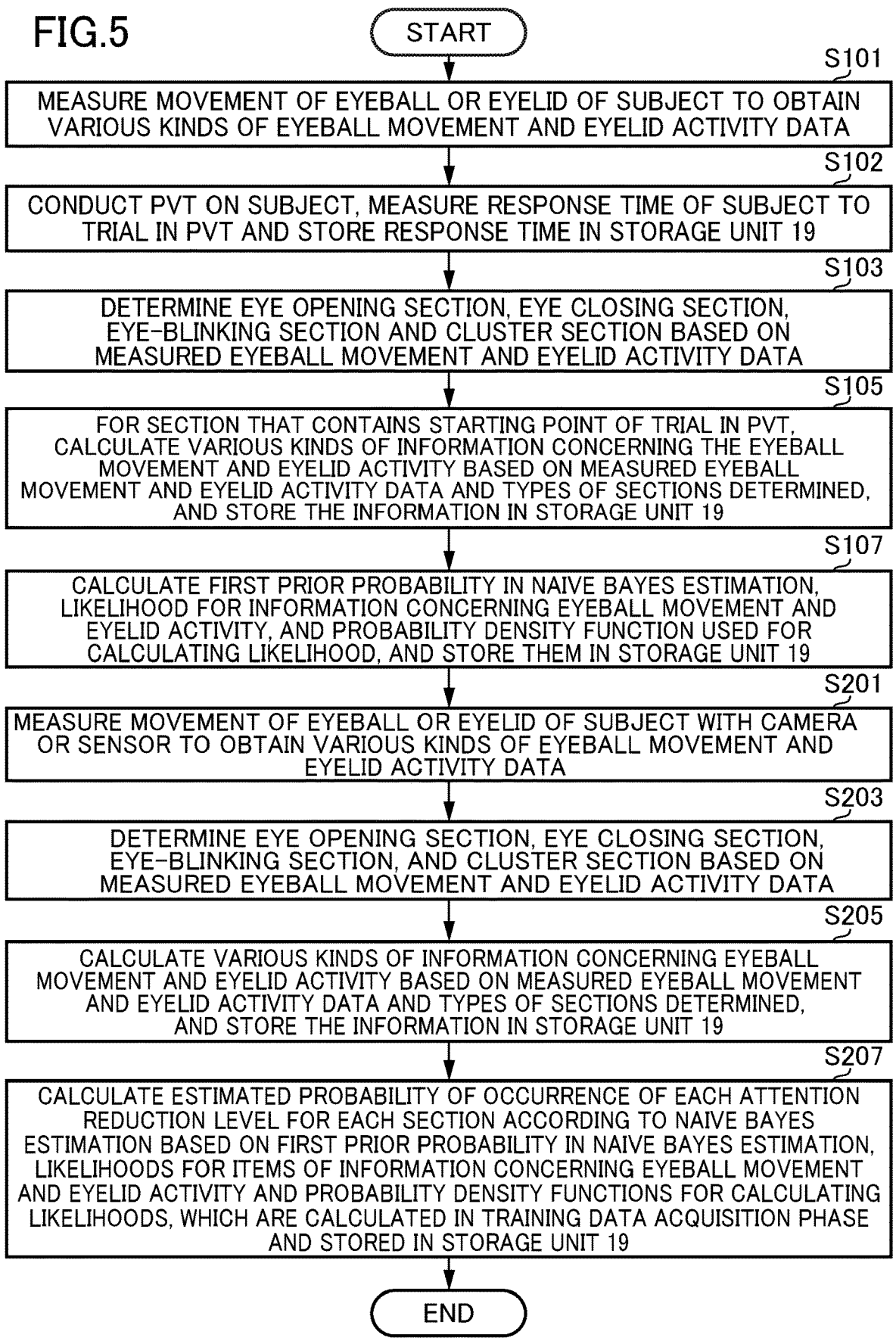
FIG. 5 is a flowchart showing an example of a reduced attention state estimation process performed by the reduced attention state estimation system according to the first embodiment of the present invention.

An example of a reduced attention state estimation process according to an embodiment of the present invention performed by the reduced attention state estimation system having the system configuration described above will be described below with reference to FIGS. 1 and 3 to 5. FIG. 5 is a flowchart showing an example of a reduced attention state estimation process according to an embodiment of the present invention performed by the reduced attention state estimation system.

[I] Training Data Acquisition Phase

In this embodiment, the Naive Bayes estimation is used. Therefore, training data used to determine the prior probability and the likelihood required for the Naive Bayes estimation is first acquired. The Bayes estimation is to determine an posterior probability $P(H_i|D)$ from an prior probability $P(H_i)$, a likelihood $P(D|H)$ according to the Bayes' theorem expressed by the following formula (1) that holds for a cause $H_i$ of data D.

$$P(H_i | D) = \frac{P(H_i) \cdot P(D | H_i)}{\Sigma P(H_j) \cdot P(D | H_j)} \quad \text{formula (1)}$$

The Naive Bayes estimation is a method of determining the probability of a cause $H_i$ by using a determined posterior probability as an prior probability to determine an posterior probability of another piece of data and repeating the determination (Bayes update) on the assumption that the causes $H_i$ are independent of each other. In the following, a procedure performed in the training data acquisition phase will be described.

The eyeball movement and eyelid activity measurement unit 11 measures the movement of an eyeball or eyelid of a subject with a camera or sensor to obtain various kinds of eyeball movement and eyelid activity data (S101).

The PVT conducting unit 12 conducts the PVT on the subject, measures the response time of the subject to a trial in the PVT and stores the response time in the storage unit 19 (S102).

The section determination unit 13 determines an eye opening section, an eye closing section, an eye-blinking section and a cluster section based on the eyeball movement and eyelid activity data obtained by the eyeball movement and eyelid activity measurement unit 11 (S103). The section determination may be performed in the same manner as described above with regard to the experiment, for example.

For a section (see the hatched sections in FIG. 1) that contains the starting point of a trial in the PVT, the eyeball movement and eyelid activity-related information calculation unit 15 calculates various kinds of information concerning the eyeball movement and eyelid activity based on the eyeball movement and eyelid activity data obtained by the eyeball movement and eyelid activity measurement unit 11 and the types of the sections determined by the section determination unit 13, and stores the information in the storage unit 19 (S105). The calculation of the various kinds of information concerning the eyeball movement and eyelid activity may be performed in the same manner as described above with regard to the experiment, for example.

The prior probability and likelihood calculation unit 18 calculates the first prior probability in the Naive Bayes estimation, the likelihood for the information concerning the eyeball movement and eyelid activity, and a probability density function used for calculating the likelihood, and stores them in the storage unit 19 (S107).

More specifically, the prior probability and likelihood calculation unit 18 determines whether the attention reduction level is normal (100 ms≤RT<300 ms), mild (300 ms≤RT<500 ms) or severe (300 ms≤RT<500 ms) for each trial based on the response time to the trial in the PVT stored in the storage unit 19, and stores the result in the storage unit 19. The value obtained by dividing the number of trials for which each of the normal, the mild and the severe attention reduction levels occurs by the total number of trials are designated as the probability of occurrence of each of the attention reduction levels, and used as prior probability of each of the attention reduction levels in the Naive Bayes estimation. $P(H_1)$ denotes the prior probability of the normal attention reduction level, $P(H_2)$ denotes the prior probability of the mild attention reduction level, and $P(H_3)$ denotes the prior probability of the severe attention reduction level.

Furthermore, for the following items of information concerning the eyeball movement and eyelid activity, the likelihood and a probability density function for calculating the likelihood are calculated.

(1) Whether Relevant Section is Eye Closing Section, Eye Opening Section or Eye-Blinking Section The number of occurrences of an eye opening section, the number of occurrences of an eye closing section and the number of occurrences of an eye-blinking section for each attention reduction level are divided by the total number of occurrences of the eye opening sections ($D_{1-1}$), the total number of occurrences of the eye closing sections ($D_{1-2}$) and the total number of occurrences of the eye-blinking sections ($D_{1-3}$), respectively, to determine the likelihoods ($P(D_{1-1}|H_i)$, $P(D_{1-2}|H_i)$, $P(D_{1-3}|H_i)$, $P(D_{1-1}|H_2)$, $P(D_{1-2}|H_2)$, $P(D_{1-3}|H_2)$, $P(D_{1-1}|H_3)$, $P(D_{1-2}|H_3)$ and $P(D_{1-3}|H_3)$) of the respective sections for each attention reduction level.

(2) Whether Eye Closing Section is Included in Cluster Section

The number of eye closing sections ($D_{2-1}$) occurring in a cluster section and the number of occurrences of the other eye closing sections ($D_{2-2}$) for each attention reduction level are divided by the total number of occurrences of eye closing sections to determine the likelihoods ($P(D_{2-1}|H_i)$, $P(D_{2-2}|H_1)$, $P(D_{2-1}|H_2)$, $P(D_{2-2}|H_2)$, $P(D_{2-1}|H_3)$ and $P(D_{2-2}|H_3)$) for each attention reduction level.

(3) Whether Eye Opening or Eye-Blinking Section is Included in Cluster Section

The number of occurrences of cluster sections (that contain an eye-blinking section or an eye opening section) ($D_{3-1}$) and the number of eye opening section ($D_{3-2}$) that are not contained in a cluster section and the number of eye-blinking sections ($D_{3-3}$) that are not contained in a cluster section are calculated for each attention reduction level. These numbers of occurrence are divided by the number of occurrences of the other sections than the eye closing sections to determine the likelihoods ($P(D_{3-1}|H_1)$, $P(D_{3-2}|H_1)$, $P(D_{3-3}|H_1)$, $P(D_{3-1}|H_2)$, $P(D_{3-2}|H_2)$, $P(D_{3-3}|H_1)$, $P(D_{3-1}\ H_3)$, $P(D_{3-2}|H_3)$ and $P(D_{3-3}|H_1)$) of the respective sections for each attention reduction level.

(4) Duration of Eye Opening Section

For this item of information concerning the eyeball movement and eyelid activity, a probability density function of a normal distribution is calculated from an average value ($\mu$) and a standard deviation ($\sigma$) for each attention reduction level according to the following formula (2).

$$f(x, \mu, \sigma) = \frac{1}{\sqrt{2\pi}\,\sigma} e^{-\left(\frac{(x-\mu)^2}{2\sigma^2}\right)} \quad \text{formula (2)}$$

That is, an average value ($\mu_6$) and a standard deviation ($\sigma_6$) of the durations of all the eye opening sections are determined for each attention reduction level, and a probability density function for each attention reduction level is calculated by substituting $\mu_6$ and $\sigma_6$ for $\mu$ and $\sigma$ in the formula (2).

(5) Frequency of Microsaccades

For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_4$) and a standard deviation ($\sigma_4$) of the frequency of microsaccades in each of eye opening sections in which at least one eyeball movement occurs are determined for each attention reduction level, and a probability density function for each attention reduction level is calculated by substituting $\mu_4$ and $\sigma_4$ for $\mu$ and $\sigma$ in the formula (2).

(6) Average Value of Sharpness of Microsaccade

For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_5$) and a standard deviation ($\sigma_5$) of the average value of the sharpness of microsaccade in an eye opening section in which at least one microsaccade occurs are determined for each attention reduction level, and a probability density function for each attention reduction level is calculated by substituting $\mu_5$ and $\sigma_5$ for $\mu$ and $\sigma$ in the (formula 2).

(7) Average Value of Degree of Eyelid Opening

For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_7$) and a standard deviation ($\sigma_7$) of the average value of the degree of eyelid opening in each of all the sections are determined, and a probability density function for each attention reduction level is calculated by substituting $\mu_7$ and $\sigma_7$ for $\mu$ and $\sigma$n the formula (2).

(8) Standard Deviation of Degree of Eyelid Opening

For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_8$) and a standard deviation ($\sigma_8$) of the standard deviation of the degree of eyelid opening in each of the eye opening sections and the eye closing sections are determined, and a probability density function for each attention reduction level is calculated by substituting $\mu_8$ and $\sigma_8$ for and $\sigma$ in the formula (2).

(9) Frequency of Eye-Blinkings

For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_9$) and a standard deviation ($\sigma_9$) of the frequency of eye-blinkings in each of all the cluster sections are determined for each attention reduction level, and a probability density function for each attention reduction level is calculated by substituting $\mu_9$ and $\sigma_9$ for $\mu$ and $\sigma$ in the formula (2).

(10) Average Value of Inverse of Relative Velocity of Eyelid Closure at an Eyelid Closing Time For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_{10}$) and a standard deviation ($\sigma_{10}$) of the average value of the inverse of the relative velocity of an eyelid closure at an eyelid closing time in each of all the cluster sections containing an eye-blinking section are determined for each attention reduction level. A probability density function for each attention reduction level is calculated according to the formula (2) by substituting $\mu_{10}$ and $\sigma_{10}$ for $\mu$ and $\sigma$ in the formula (2).

(11) Average Value of Inverse of Relative Velocity of Eyelid Opening at an Eyelid Opening Time For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_{11}$) and a standard deviation ($\sigma_{11}$) of the average value of the inverse of the relative velocity of an eyelid opening at an eyelid opening time in each of all the cluster sections containing an eye-blinking section are determined for each attention reduction level, and a probability density function for each attention reduction level is calculated by substituting $11l$ and $\sigma_{11}$ for $\mu$ and $\sigma$ in the formula (2).

(12) Duration of Eye-Blinking

For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_{12}$) and a standard deviation ($\sigma_{12}$) of the average value of the duration of an eye-blinking in each of all the cluster sections containing an eye-blinking section are determined for each attention reduction level, and a probability density function for each attention reduction level is calculated by substituting $\mu_{12}$ and $\sigma_{12}$ for $\mu$ and $\sigma$ in the formula (2).

(13) Duration of Closed Eye in Eye-Blinking

For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_{13}$) and a standard deviation ($\sigma_{13}$) of the average value of the duration of a closed eye in an eye-blinking in each of all the cluster sections containing an eye-blinking section are determined for each attention reduction level, and a probability density function for each attention reduction level is calculated by substituting $\mu_{13}$ and $\sigma_{13}$ for $\mu$ and $\sigma$ in the formula (2).

(14) Rate of Occurrence of Eye-Blinkings

For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_{14}$) and a standard deviation ($\sigma_{14}$) of the rate of occurrence of eye-blinkings in each cluster section are determined for each attention reduction level, and a probability density function for each attention reduction level is calculated by substituting $\mu_{14}$ and $\sigma_{14}$ for $\mu$ and $\sigma$ in the formula (2).

(15) Short-Time Eye-Closure Occurrence Rate

For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_{15}$) and a standard deviation ($\sigma_{15}$) of the rate of occurrence of eye closures (with a duration shorter than 1 second) in each cluster section are determined for each attention reduction level, and a probability density function for each attention reduction level is calculated by substituting $\mu_{15}$ and $\sigma_{15}$ for $\mu$ and $\sigma$ in the formula (2).

(16) Long-Time Eye-Closure Occurrence Rate

For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_{16}$) and a standard deviation ($\sigma_{16}$) of the rate of occurrence of eye closures (with a duration equal to or longer than 1 second) in each cluster section are determined for each attention reduction level, and a probability density function for each attention reduction level is calculated by substituting $\mu_{16}$ and $\sigma_{16}$ for $\mu$ and $\sigma$ in the formula (2).

(17) Duration of Eye Closing Section

For this item of information concerning the eyeball movement and eyelid activity, a probability density function of a normal distribution is calculated from the average value ($\mu$) and the standard deviation ($\sigma$) for each attention reduction level according to the above formula (2). That is, an average value ($\mu_{17}$) and a standard deviation ($\sigma_{17}$) of the durations of all the eye closing sections are determined for each attention reduction level, and a probability density function for each attention reduction level is calculated by substituting $\mu_{17}$ and $\sigma_{17}$ for $\mu$ and $\sigma$ in the formula (2).

For the items of information (4) to (17) concerning the eyeball movement and eyelid activity, if a value of an item of information concerning the eyeball movement and eyelid activity for any attention reduction level does not follow the normal distribution, the value of the item of information concerning the eyeball movement and eyelid activity may be categorized according to a threshold to calculate the likelihood. The likelihood of each category for each attention reduction level may be calculated by dividing the number of pieces of data in each category by the number of pieces of data in all the categories.

[II] Attention Assessment Calculation Phase

Based on the prior probability obtained in the training data acquisition phase, the likelihoods for the items of information concerning the eyeball movement and eyelid activity and the probability density functions for calculating the likelihoods, an attention assessment is calculated from eyeball movement and eyelid activity data obtained by measurement of a movement of an eyeball or eyelid of a subject.

The eyeball movement and eyelid activity measurement unit 11 measures a movement of an eyeball or eyelid of a subject with a camera or sensor to obtain various kinds of eyeball movement and eyelid activity data (S201).

As in Step S103 in the training data acquisition phase described above, the section determination unit 13 determines an eye opening section, an eye closing section, an eye-blinking section, and a cluster section based on the eyeball movement and eyelid activity data obtained by the eyeball movement and eyelid activity measurement unit 11 (S203).

As in Step S105 in the training data acquisition phase described above, for each section determined by the section determination unit 13, the eyeball movement and eyelid activity-related information calculation unit 15 calculates various kinds of information concerning the eyeball movement and eyelid activity based on the eyeball movement and eyelid activity data obtained by the eyeball movement and eyelid activity measurement unit 11 and the types of the sections determined by the section determination unit 13 (S205).

The attention assessment unit 17 calculates the estimated probability of occurrence of each attention reduction level for each section according to the Naive Bayes estimation according to the formula (1) based on the first prior probability in the Naive Bayes estimation, the likelihoods for the items of information concerning the eyeball movement and eyelid activity and the probability density functions for calculating the likelihoods, which are calculated in the training data acquisition phase and stored in the storage unit 19 (S207).

Specifically, for each of the sections described below, the probability of occurrence of each attention reduction level is calculated by sequentially calculating the posterior probability for each item of information concerning the eyeball movement and eyelid activity for each attention reduction level by the Bayes update according to the formula (1), which is the Bayes' theorem, as described below. The order of calculation of the posterior probabilities of the items of information concerning the eyeball movement and eyelid activity is arbitrary because of the sequential rationality of the Bayes' theorem. An example will be described below.

(1) Eye Opening/Cluster Section

For an eye opening/cluster section (denoted by "a" in FIG. 1, for example), which is an eye opening section and cluster section, as the information concerning the eyeball movement and eyelid activity, whether the section is an eye opening section, an eye closing section or an eye-blinking section ($P(D_{1\text{-}1})$, $P(D_{1\text{-}2})$ or $P(D_{1\text{-}3})$), whether an eye opening section or eye-blinking section is included in the cluster section ($P(D_{3\text{-}1})$, $P(D_{3\text{-}2})$), the frequency of microsaccades ($D_4$), the sharpness of microsaccade ($D_5$), the duration of the eye opening section ($D_6$), the average value of the degree of eyelid opening ($D_7$), the standard deviation of the degree of eyelid opening ($D_8$), the frequency of eye-blinkings ($D_9$), the inverse of the relative velocity of an eyelid closure at an eyelid closing time ($D_{10}$), the inverse of the relative velocity of an eyelid opening at an eyelid opening time ($D_{11}$), the duration of an eye-blinking ($D_{12}$), the eye-blinking occurrence rate ($D_{14}$), the short-time eye-closure occurrence rate ($D_{15}$) and the long-time eye-closure occurrence rate ($D_{16}$) are used.

(A) The average value of the degree of eyelid opening ($D_7$) for the relevant section is substituted for x in the probability density function (formula (2)) for each category determined in the training data acquisition phase to calculate the likelihood. From the prior probabilities $p(H_1)$, $p(H_2)$ and $p(H_3)$ calculated in the training data acquisition phase and the determined likelihood, the posterior probabilities ($P(H_1|D)$, $P(H_2|D_7)$, $P(H_3|D_T)$) for the average value of the degree of eyelid opening are calculated according to the formula (1).

(B) The standard deviation of the degree of eyelid opening ($D_8$) for the relevant section is substituted for x in the probability density function (formula (2)) for each category determined in the training data acquisition phase to calculate the likelihood. The posterior probabilities determined in (A) described above are used as prior probabilities. From these prior probabilities and the determined likelihood, the posterior probabilities ($P(H_1|D_8)$, $P(H_2|D_8)$, $P(H_3|D_8)$) for the standard deviation of the degree of eyelid opening are calculated according to the formula (1).

(C) The posterior probabilities determined in (B) described above are used as prior probabilities. From these prior probabilities and the likelihoods ($P(D_{D-1}|H)$, $P(D_{D-1}|H_2)$, $P(D_{1-1}|H_3)$) determined in the training data acquisition phase, the posterior probabilities ($P(H_1|D_{1-1})$, $P(H_2|D_{1-1})$, $P(H_3|D_{1-1})$) of whether the section is an eye opening section, whether the section is an eye closing section and whether the section is an eye-blinking section are calculated according to the formula (1).

(D) The posterior probabilities determined in (C) described above are used as prior probabilities. From these prior probabilities and the likelihoods ($P(D_{3-1}|H)$, $P(D_{3-1}|H_2)$, $P(D_{3-1}|H_3)$) determined in the training data acquisition phase, the posterior probabilities ($P(H_i|D_{3-1})$, $P(H_2|D_{3-1})$, $P(H_3|D_{3-1})$) of whether an eye opening section or eye-blinking section is included in the cluster section are calculated according to the formula (1).

(E) The duration of the eye opening section ($D_6$) for the relevant section is substituted for x in the probability density function (formula (2)) for each category determined in the training data acquisition phase to calculate the likelihood. The posterior probabilities determined in (D) described above are used as prior probabilities. From these prior probabilities and the determined likelihood, the posterior probabilities ($P(H_i|D_6)$, $P(H_2|D_6)$, $P(H_3|D_6)$) for the duration of the eye opening section are calculated according to the formula (1).

(F) If an eyeball movement occurs in the relevant section, the frequency of microsaccades ($D_4$) for the relevant section is substituted for x in the probability density function (formula (2)) for each category determined in the training data acquisition phase to calculate the likelihood. The posterior probabilities determined in (E) described above are used as prior probabilities. From these prior probabilities and the determined likelihood, the posterior probabilities ($P(H_1|D_4)$, $P(H_2|D_4)$, $P(H_3|D_4)$) for the frequency of microsaccades are calculated according to the formula (1).

(G) If an eyeball movement occurs in the relevant section, the sharpness of microsaccade ($D_5$) for the relevant section is substituted for x in the probability density function (formula (2)) for each category determined in the training data acquisition phase to calculate the likelihood. The posterior probabilities determined in (F) described above are used as prior probabilities. From these prior probabilities and the determined likelihood, the posterior probabilities ($P(H_1|D_5)$, $P(H_2|D_5)$, $P(H_3|D_5)$) for the sharpness of microsaccade are calculated according to the formula (1).

(H) The frequency of eye-blinkings ($D_9$) for the cluster section containing the relevant section is substituted for x in the probability density function (formula (2)) for each category determined in the training data acquisition phase to calculate the likelihood. The posterior probabilities determined in (G) described above are used as prior probabilities. From these prior probabilities and the determined likelihood, the posterior probabilities ($P(H_1|D_9)$, $P(H_2|D_9)$, $P(H_3|D_9)$) for the frequency of eye-blinkings are calculated according to the formula (1).

(I) The inverse of the relative velocity of an eyelid closure at an eyelid closing time ($D_{10}$) for the cluster section containing the relevant section is substituted for x in the probability density function (formula (2)) for each category determined in the training data acquisition phase to calculate the likelihood. The posterior probabilities determined in (H) described above are used as prior probabilities. From these prior probabilities and the determined likelihood, the posterior probabilities ($P(H_i|D_{10})$, $P(H_2|D_{10})$, $P(H_3|D_{10})$) for the inverse of the relative velocity of an eyelid closure at an eyelid closing time are calculated according to the formula (1).

(J) The inverse of the relative velocity of an eyelid opening at an eyelid opening time ($D_{11}$) for the cluster section containing the relevant section is substituted for x in the probability density function (formula (2)) for each category determined in the training data acquisition phase to calculate the likelihood. The posterior probabilities determined in (I) described above are used as prior probabilities. From these prior probabilities and the determined likelihood, the posterior probabilities ($P(H_1|D_{11})$, $P(H_2|D_{11})$, $P(H_3|D_{11})$) for the inverse of the relative velocity of an eyelid opening at an eyelid opening time are calculated according to the formula (1).

(K) The duration of an eye-blinking ($D_{12}$) for the cluster section containing the relevant section is substituted for x in the probability density function (formula (2)) for each category determined in the training data acquisition phase to calculate the likelihood. The posterior probabilities determined in (J) described above are used as prior probabilities. From these prior probabilities and the likelihood, the posterior probabilities ($P(H_1|D_{12})$, $P(H_2|D_{12})$, $P(H_3|D_{12})$) for the duration of an eye-blinking are calculated according to the formula (1).

(L) The duration of eye closure ($D_{13}$) for the cluster section containing the relevant section is substituted for x in the probability density function (formula (2)) for each category determined in the training data acquisition phase to calculate the likelihood. The posterior probabilities determined in (K) described above are used as prior probabilities. From these prior probabilities and the likelihood, the posterior probabilities ($P(H_1|D_{13})$, $P(H_2|D_{13})$, $P(H_3|D_{13})$) for the duration of eye closure are calculated according to the formula (1).

(M) The rate of occurrence of eye-blinkings ($D_{14}$) for the cluster section containing the relevant section is substituted for x in the probability density function (formula (2)) for each category determined in the training data acquisition phase to calculate the likelihood. The posterior probabilities determined in (L) described above are used as prior probabilities. From these prior probabilities and the likelihood, the posterior probabilities ($P(H_i|D_{14})$, $P(H_2|D_{14})$, $P(H_3|D_{14})$) for the rate of occurrence of eye-blinkings are calculated according to the formula (1).

(N) The short-time eye-closure occurrence rate ($D_{15}$) for the cluster section containing the relevant section is substituted for x in the probability density function (formula (2)) for each category determined in the training data acquisition phase to calculate the likelihood. The posterior probabilities determined in (M) described above are used as prior probabilities. From these prior probabilities and the likelihood, the posterior probabilities ($P(H_i|D_{15})$, $P(H_2|D_{15})$, $P(H_3|D_{15})$) for the short-time eye-closure occurrence rate are calculated according to the formula (1).

(O) The long-time eye-closure occurrence rate ($D_{16}$) for the cluster section containing the relevant section is substituted for x in the probability density function (formula (2)) for each category determined in the training data acquisition phase to calculate the likelihood. The posterior probabilities determined in (N) described above are used as prior probabilities. From these prior probabilities and the likelihood, the posterior probabilities ($P(H_i|D_{16})$, $P(H_2|D_{16})$, $P(H_3|D_{16})$) for the long-time eye-closure occurrence rate are calculated according to the formula (1). The posterior probabilities are the estimated probabilities of occurrence of the attention reduction levels.

(2) Eye Closing/Cluster Section

For an eye closing/cluster section (denoted by "b" in FIG. 1, for example), which is an eye closing section and cluster section, whether the section is an eye opening section, an eye closing section or an eye-blinking section ($P(D_{1-1})$, $P(D_{1-2})$ or $P(D_{1-3})$), whether an eye closing section is included in the cluster section ($P(D_{2-1})$, $P(D_{2-2})$), the average value of the degree of eyelid opening ($D_7$), the standard deviation of the degree of eyelid opening ($D_8$), the frequency of eye-blinkings ($D_9$), the inverse of the relative velocity of an eyelid opening at an eyelid opening time ($D_{11}$), the duration of an eye-blinking ($D_{12}$), the duration of eye closure in an eye-blinking ($D_{13}$), the eye-blinking occurrence rate ($D_{14}$), the short-time eye-closure occurrence rate ($D_{15}$) and the long-time eye-closure occurrence rate ($D_{16}$) are used as the information concerning the eyeball movement and eyelid activity to calculate the estimated probability of occurrence of each attention reduction level, as with the eye opening/cluster section of (1) described above.

(3) Eye-Blinking/Cluster Section

For an eye-blinking/cluster section (denoted by "c" in FIG. 1, for example), which is an eye-blinking section and cluster section, whether the section is an eye opening section, an eye closing section or an eye-blinking section ($P(D_{1-1})$, $P(D_{1-2})$ or $P(D_{1-3})$), whether an eye opening section or eye-blinking section is included in the cluster section ($P(D_{3-1})$, $P(D_{3-2})$), the frequency of eye-blinkings ($D_9$), the inverse of the relative velocity of an eyelid closure at an eyelid closing time ($D_{10}$), the inverse of the relative velocity of an eyelid opening at an eyelid opening time ($D_{11}$), the duration of an eye-blinking ($D_{12}$), the duration of eye closure in an eye-blinking ($D_{13}$), the eye-blinking occurrence rate ($D_{14}$), the short-time eye-closure occurrence rate ($D_{15}$) and the long-time eye-closure occurrence rate ($D_{16}$) are used as the information concerning the eyeball movement and eyelid activity to calculate the estimated probability of occurrence of each attention reduction level, as with the eye opening/cluster section of (1) described above.

(4) Eye Opening/Non-Cluster Section

For eye opening/non-cluster section (denoted by "d" in FIG. 1, for example), which is an eye opening section and non-cluster section, whether the section is an eye opening section, an eye closing section or an eye-blinking section ($P(D_{1-1})$, $P(D_{1-2})$ or $P(D_{1-3})$), whether an eye opening section or eye-blinking section is included in the cluster section ($P(D_{3-1})$, $P(D_{3-2})$), the frequency of microsaccades ($D_4$), the sharpness of microsaccade ($D_5$), the duration of the eye opening section ($D_6$), the average value of the degree of eyelid opening ($D_7$) and the standard deviation of the degree of eyelid opening ($D_8$) are used as the information concerning the eyeball movement and eyelid activity to calculate the estimated probability of occurrence of each attention reduction level, as with the eye opening/cluster section of (1) described above.

(5) Eye Closing/Non-Cluster Section

For an eye closing/non-cluster section (denoted by "e" in FIG. 1, for example), which is an eye closing section and non-cluster section, whether the section is an eye opening section, an eye closing section or an eye-blinking section ($P(D_{1-1})$, $P(D_{1-2})$ or $P(D_{1-3})$), whether an eye closing section is included in the cluster section ($P(D_{2-1})$, $P(D_{2-2})$), the average value of the degree of eyelid opening ($D_7$), the standard deviation of the degree of eyelid opening ($D_8$) and the duration of the eye closing section ($D_{17}$) are used as the information concerning the eyeball movement and eyelid activity to calculate the estimated probability of occurrence of each attention reduction level, as with the eye opening/cluster section of (1) described above.

(6) Eye-Blinking/Non-Cluster Section

For an eye-blinking/non-cluster section (denoted by "f" in FIG. 1, for example), which is an eye-blinking section and non-cluster section, whether the section is an eye opening section, an eye closing section or an eye-blinking section ($P(D_{1-1})$, $P(D_{1-2})$ or $P(D_{1-3})$) and whether an eye opening section is included in the cluster section an eye opening section or eye-blinking section is included in the cluster section ($P(D_{3-1})$, $P(D_{3-2})$) are used as the information concerning the eyeball movement and eyelid activity to calculate the estimated probability of occurrence of each attention reduction level, as with the eye opening/cluster section of (1) described above.

The attention assessment unit 17 may further determine the attention level per assessment time based on the determined estimated probability of occurrence of each attention reduction level. More specifically, the estimated occurrence probability ($P(H)_k$) determined for each of the sections (the eye opening/cluster section, the eye closing/cluster section, the eye-blinking/cluster section, the eye opening/non-cluster section, the eye closing/non-cluster section and the eye-blinking/non-cluster section) appearing in an assessment time is multiplied by the duration ($Duration_k$) of the section, the products are summed over N sections, which are all the sections appearing in the assessment time, and then the sum is divided by the assessment time to determine the estimated probability of occurrence of each attention reduction level per assessment time (formula (3)).

$$p(H_i) = \frac{\Sigma_1^N p(H_i)_k \times Duration_k}{\Sigma_1^N Duration_k} \qquad \text{formula (3)}$$

In the experiment described above, the training data acquisition phase described above was conducted for each subject in the first half of sessions (the first to tenth sessions), and the attention assessment calculation phase described above was conducted based on the personal training data of the subject in the second half of sessions (the eleventh to twenty-second sessions). For the data obtained in the experiment described above, FIG. 6 shows the probability of occurrence of each attention reduction level per 20 minutes determined in the PVT, the estimated probability of occurrence of each attention reduction level per 20 minutes determined in the reduced attention state estimation method according to the embodiment, and a correlation therebetween.

Figure 6:
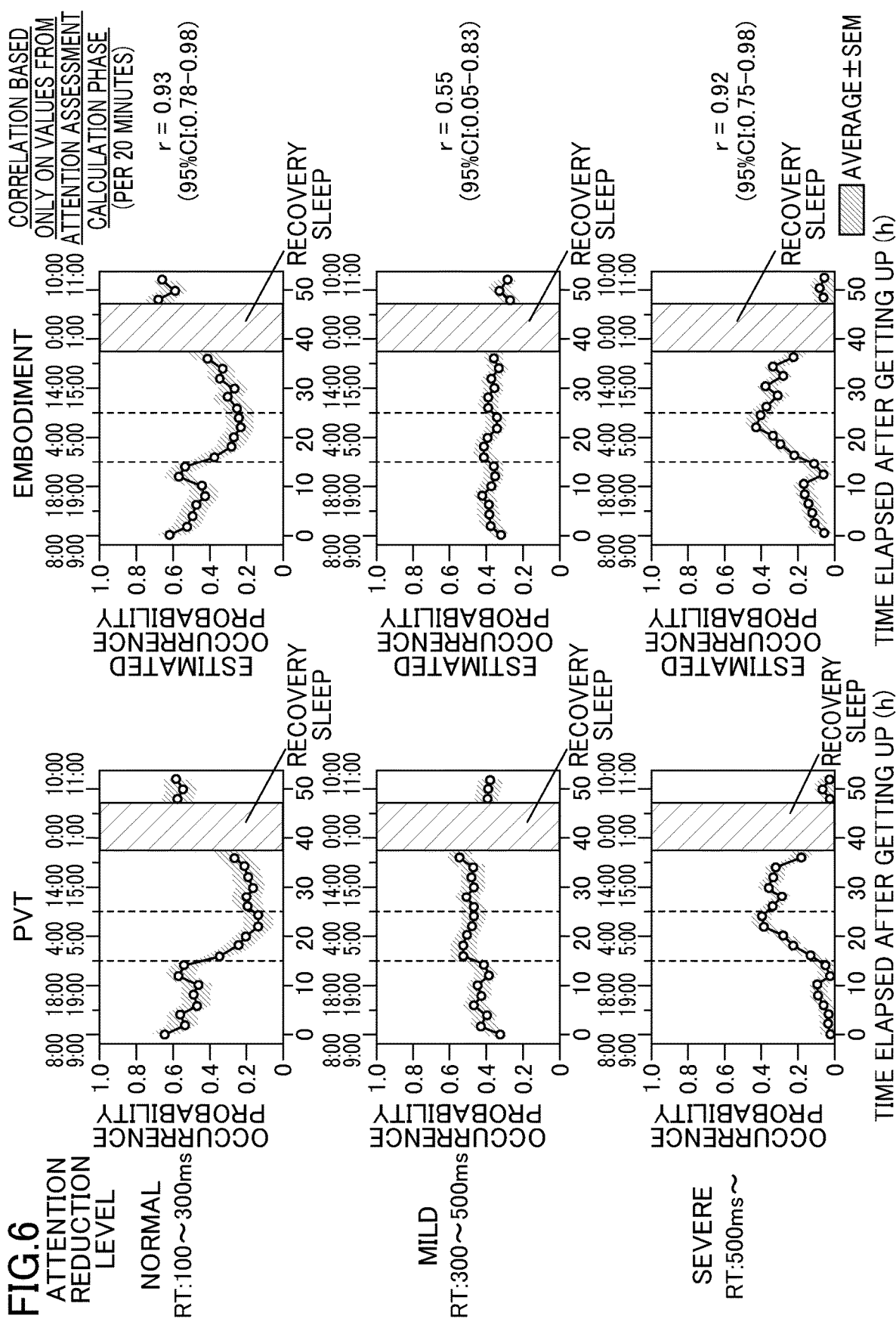
FIG. 6 shows the probability of occurrence of each attention reduction level per 20 minutes determined in the PVT, the estimated probability of occurrence of each attention reduction level per 20 minutes determined in a reduced attention state estimation method according to the first embodiment of the present invention, and a correlation therebetween.

As can be seen from FIG. 6, the variation of the estimated probability of occurrence of each attention reduction level per 20 minutes determined in the reduced attention state estimation method according to this embodiment highly matched the variation of the estimated probability of occurrence of each attention reduction level per 20 minutes determined in the PVT. Furthermore, a correlation (the Pearson's product-moment correlation coefficient) between the occurrence probability determined in the PVT and the estimated occurrence probability determined in the reduced attention state estimation method according to this embodiment was determined using only the values obtained in the attention assessment calculation phase. A Pearson's product-moment correlation coefficient r for each subject was transformed by Fisher's Z transformation to follow the normal distribution, and then a group average was determined. FIG. 6 shows the correlation coefficient (r) inverse Z-transformed. As a result, it was shown that, not only for the normal attention reduction level and the severe attention reduction level but also for the mild attention reduction level, there was a significant correlation between the occurrence probability determined in the PVT and the estimated occurrence probability determined in the reduced attention state estimation method according to this embodiment. This shows that, according to the reduced attention state estimation method according to this embodiment, various levels of attention reduction may be continuously measured without giving any test.

For the data obtained in the experiment described above, FIG. 7 shows the occurrence probability per 20 minutes determined in the PVT, the estimated occurrence probability per 20 minutes determined in the reduced attention state estimation method according to the embodiment, and the PERCLOS values per 20 minutes for a mild or severe attention reduction (RT≥300 ms) and a severe attention reduction (RT≥500 ms).

Figure 7:
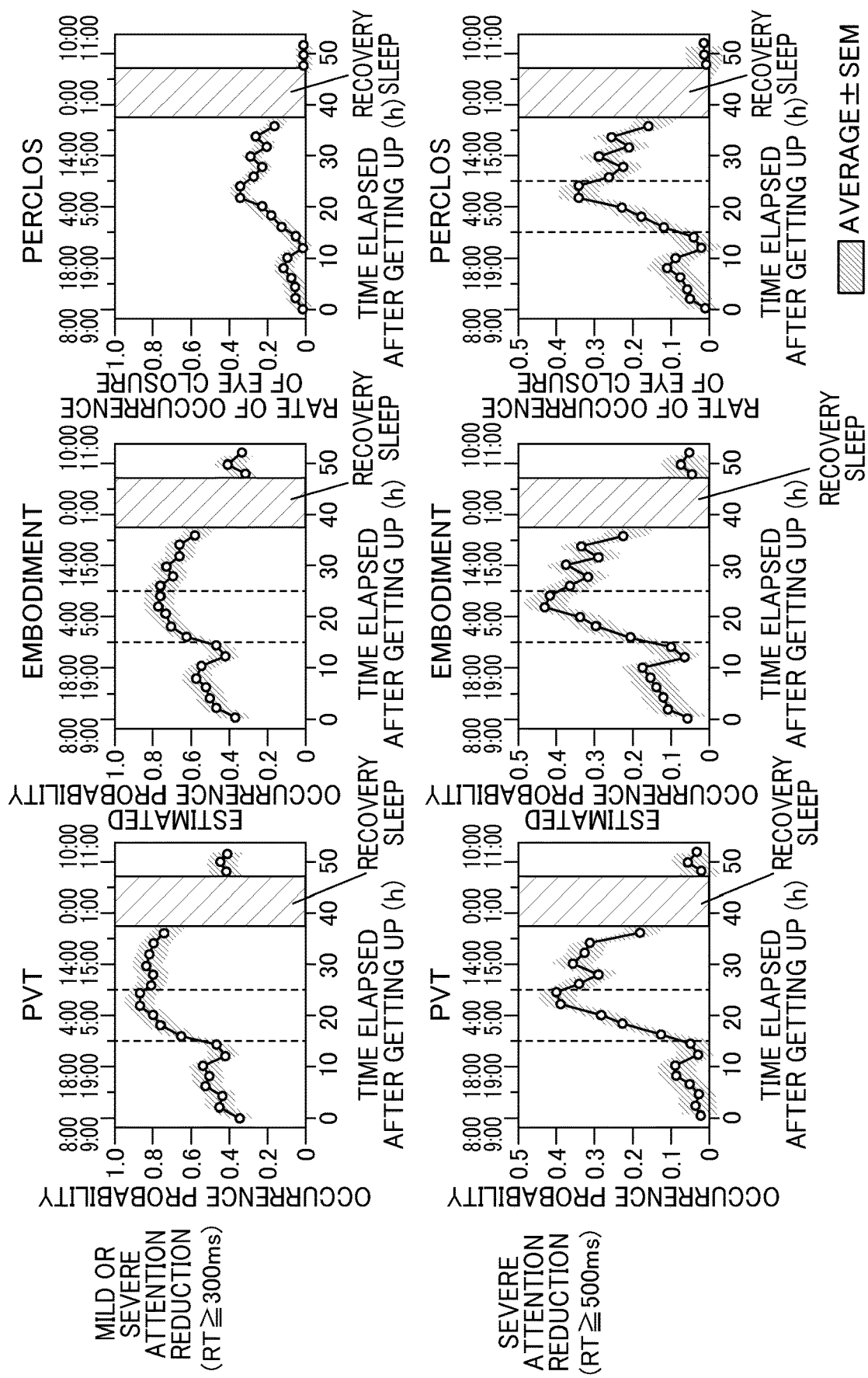
FIG. 7 shows the occurrence probability per 20 minutes determined in the PVT, the estimated occurrence probability per 20 minutes determined in the reduced attention state estimation method according to the first embodiment of the present invention, and the PERCLOS values per 20 minutes for a mild or severe attention reduction and a severe attention reduction.

As can be seen from FIG. 7, the variation of the probability of occurrence of a mild or severe attention reduction in the PVT matches the estimated probability of occurrence of a mild or severe attention reduction determined in the reduced attention state estimation method according to this embodiment, although the PERCLOS value is lower than the probability of occurrence of a mild or severe attention reduction determined in the PVT. FIG. 7 also shows that the probability of occurrence of a severe attention reduction determined in the PVT highly matches the estimated probability of occurrence of a severe attention reduction determined in the reduced attention state estimation method according to this embodiment and the PERCLOS value.

Figure 8:
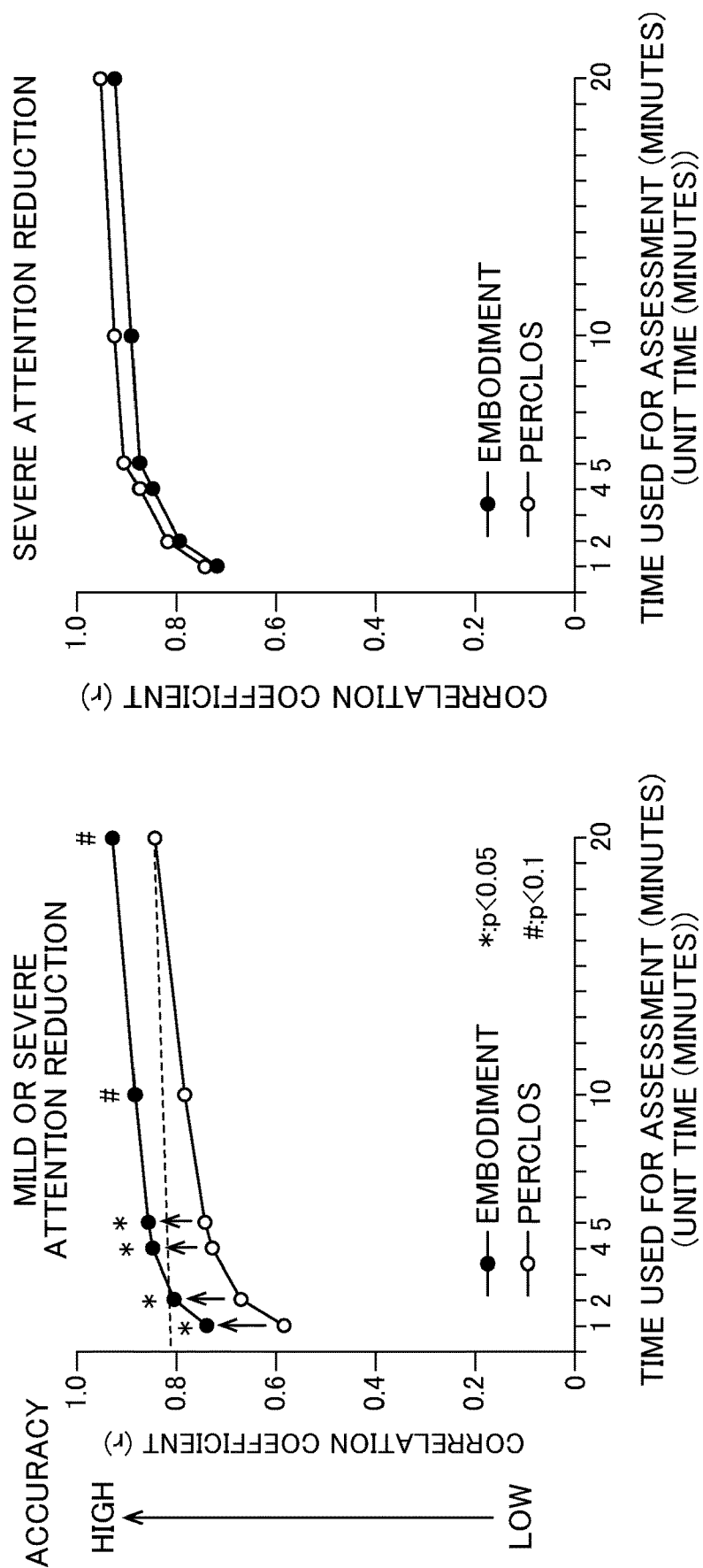
FIG. 8 shows a correlation between the occurrence probability determined in the PVT and the estimated occurrence probability determined in the reduced attention state estimation method according to the first embodiment of the present invention and the PERCLOS value for a mild or severe attention reduction determined per unit assessment time, and a correlation between the occurrence probability determined in the PVT and the estimated occurrence probability determined in the reduced attention state estimation method according to the first embodiment of the present invention and the PERCLOS value for a severe attention reduction determined per unit assessment time.

FIG. 8 shows a correlation between the occurrence probability determined in the PVT, and the estimated occurrence probability determined in the reduced attention state estimation method according to this embodiment and the PERCLOS value for a mild or severe attention reduction determined per unit assessment time, and a correlation between the occurrence probability determined in the PVT, and the estimated occurrence probability determined in the reduced attention state estimation method according to this embodiment and the PERCLOS value for a severe attention reduction determined per unit assessment time. The Pearson's product-moment correlation coefficient r for each subject was transformed by Fisher's Z transformation to follow the normal distribution, and then comparison was made of a group average of the correlation coefficients between the estimated probability of occurrence of each category determined in the reduced attention state estimation method according to this embodiment and the PERCLOS value. FIG. 8 shows the correlation coefficient (r) inverse Z-transformed. Any analysis based on the group average of the correlation coefficient described below is performed in the same manner.

As can be seen from FIG. 8, if the assessment time was equal to or less than 5 minutes, the correlation between the estimated occurrence probability determined in the reduced attention state estimation method according to this embodiment and the probability of occurrence of a mild or severe attention reduction determined in the PVT was significantly higher than the correlation between the PERCLOS value and the probability of occurrence of a mild or severe attention reduction determined in the PVT. If the assessment time was 10 minutes or 20 minutes, the correlations tended to be significant. As for the correlation with the probability of occurrence of a severe attention reduction determined in the PVT, there was no significant difference between the estimated occurrence probability determined in the reduced attention state estimation method according to this embodiment and the PERCLOS value. This shows that, although there was no significant difference in correlation with the severe attention reduction determined in the PVT between the reduced attention state estimation method according to this embodiment and the PERCLOS, the reduced attention state estimation method according to this embodiment exhibited a higher correlation with the mild or severe attention reduction determined in the PVT than the PERCLOS did. This shows that the reduced attention state estimation method according to this embodiment may more accurately measure attention than the conventional method.

Figure 9:
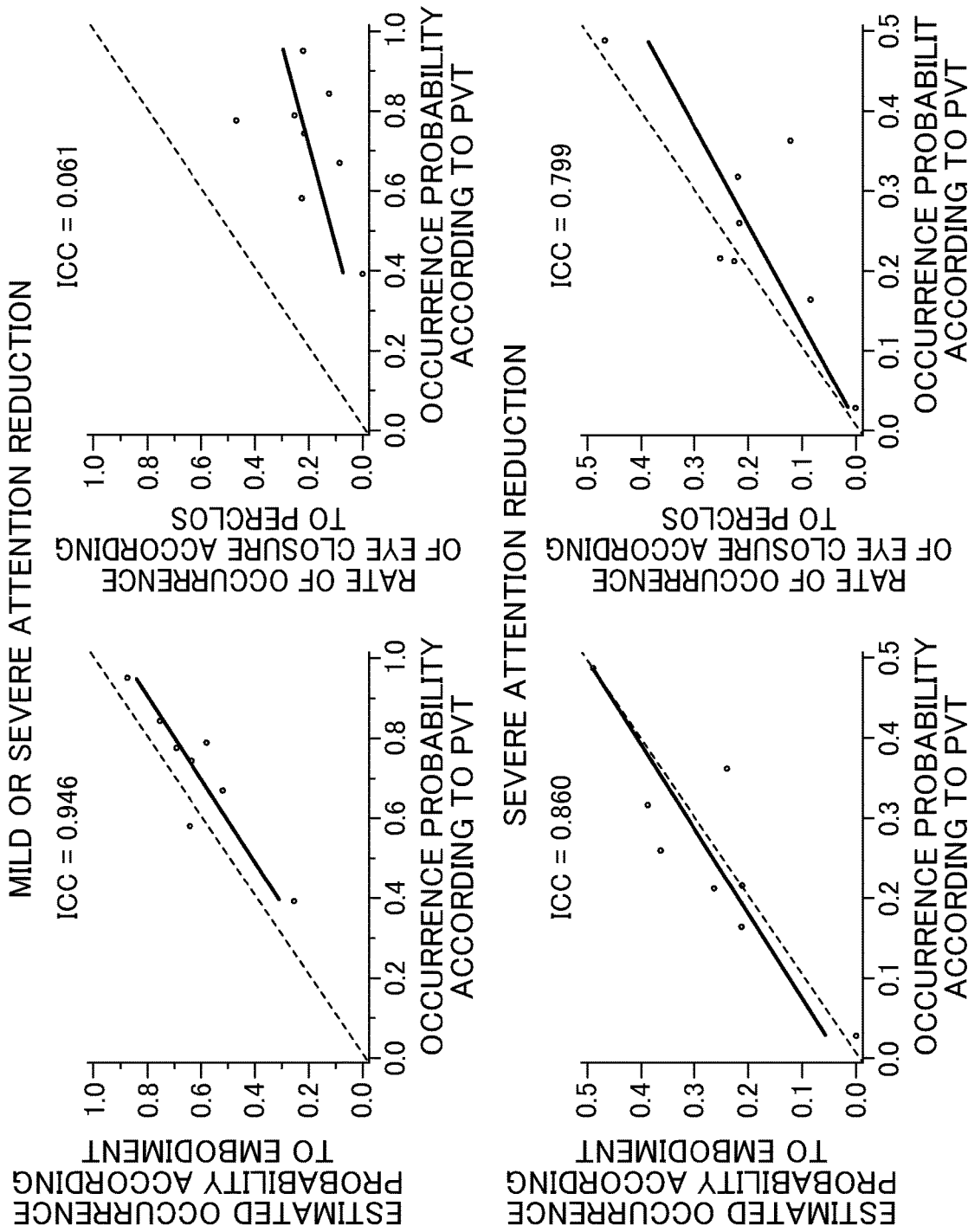
FIG. 9 shows scatter diagrams showing relationships between the PVT and the reduced attention state estimation method according to the first embodiment of the present invention and the PERCLOS and linear regression lines.

The intraclass correlation coefficient (ICC) was used to examine whether the probability of occurrence of a mild or severe attention reduction and the probability of occurrence of a severe attention reduction determined in the PVT perfectly matched (or had a relationship expressed as y=x with) the estimated probability of occurrence of a mild or severe attention reduction and the estimated probability of occurrence of a severe attention reduction determined in the reduced attention state estimation method according to this embodiment, respectively. In the examination, an average value over all the sessions in the attention assessment calculation phase for each subject was used. FIG. 9 shows scatter diagrams showing relationships between the PVT and the reduced attention state estimation method according to this embodiment and the PERCLOS, and linear regression lines for the eight cases.

If the value of the ICC is 0.81 to 1.00, the degree of perfect matching is determined to be "almost perfect". For both the mild or severe attention reduction and the severe attention reduction, the degree of perfect matching (ICC) between the PVT and the reduced attention state estimation method according to this embodiment was 0.81 or higher and thus determined to be "almost perfect". On the other hand, the value of the ICC between the PERCLOS and the PVT was lower than the value of the ICC between the reduced attention state estimation method according to this embodiment and the PVT. The reduced attention state estimation method according to this embodiment is superior in degree of perfect matching for both the probability of occurrence of a mild or severe attention reduction and the probability of occurrence of a severe attention reduction, and the estimated occurrence probability determined in the reduced attention state estimation method according to this embodiment can be used as it is as the estimated occurrence probability of attention reduction measured in the PVT. That is, it can be seen that the reduced attention state estimation method according to this embodiment facilitates reference to the knowledge of the PVT already accumulated in many prior researches.

As can be seen from the above description, the reduced attention state estimation method according to this embodiment can simply continuously measure various levels of attention reduction and facilitates reference to the knowledge of the PVT already accumulated in many prior researches.

Furthermore, since the Naive Bayes estimation is used in the reduced attention state estimation method according to this embodiment, even if some of the information concerning the eyeball movement and eyelid activity is lacking, the estimated occurrence probability may be calculated from only the available information concerning the eyeball movement and eyelid activity. Therefore, the reduced attention state estimation method according to this embodiment may flexibly adapt to situations where some of the eyeball movement and eyelid activity data cannot be obtained or some of the data is lacking, for example. Therefore, in this embodiment, the posterior probability may not be calculated for all the items of information concerning the eyeball movement and eyelid activity listed for each section, but the posterior probability may be calculated for some of the items of information concerning the eyeball movement and eyelid activity.

Although the estimated probability of occurrence of each attention reduction level and the estimated probability of occurrence of each attention reduction level per assessment time are calculated by the Naive Bayes estimation using predetermined information concerning the eyeball movement and eyelid activity in this embodiment, the attention assessment calculation method is not limited to this implementation. For example, the attention assessment may be calculated from one or a combination of the new attention assessment indices including the frequency of microsaccades due to sleepiness, the sharpness of microsaccade, the standard deviation of the degree of eyelid opening, the short-time eye-closure occurrence rate and the long-time eye-closure occurrence rate. The attention assessment may be expressed by any other appropriate measure than the estimated occurrence probability. The attention reduction may not be expressed by discrete levels but may be continuously or otherwise appropriately expressed.

The eye opening section, the eye closing section, the eye-blinking section, the cluster section, and the items of information concerning the eyeball movement and eyelid activity described above are not limited to the respective definitions described above and may be defined in any other ways as far as the essence thereof remains unchanged.

Although, in this embodiment, the likelihood for the information concerning the eyeball movement and eyelid activity and the probability density function for calculating the likelihood obtained in the training data acquisition phase are not updated each time the attention assessment is calculated in the attention assessment calculation phase, the likelihood and the probability density function may be updated each time the attention assessment is calculated.

Second Embodiment

An arrangement and a principle of operation according to a second embodiment of the present invention will be described. What has already been described above with regard to the first embodiment will not be further described.

Although the first embodiment is based on analysis of data on eight adult males as subjects (of ages of 20 to 47, 36.6±10.2[SD]) who are healthy and have no sleep disorder, this embodiment is based on analysis of data on sixteen adult males (of ages of 20 to 49, 36.7±9.3[SD]) including the eight adult males chosen as subjects in the first embodiment. As a new index for assessing attention reduction, the inventors further found a microsaccade rate from the analysis of the sixteen subjects. The inventors found that there was a significant difference between the three levels of attention reduction level, "normal", "mild" and "severe", in microsaccade rate, relative velocity of a saccade, average value of the degree of eyelid opening, standard deviation of the degree of eyelid opening and duration of an eye-blinking.

In view of this, according to this embodiment, five items of information concerning the eyeball movement and eyelid activity including the microsaccade rate, the relative velocity of a saccade, the average value of the degree of eyelid opening, the standard deviation of the degree of eyelid opening and the duration of an eye-blinking are determined from the determined types of the sections such as the eye opening section, the eye closing section, the eye-blinking section and the cluster section and the obtained eyeball movement and eyelid activity data. The average value of the degree of eyelid opening, the standard deviation of the degree of eyelid opening and the duration of an eye-blinking are determined in the same manner as in the first embodiment and therefore will not be further described. The microsaccade rate and the relative velocity of a saccade are determined as described below.

The microsaccade rate is the value obtained by dividing the number of microsaccades occurring in the eye opening section by the total number of saccades occurring in the eye opening section.

The relative velocity of a saccade is the value obtained by dividing the maximum rotational angular velocity of the eyeball movement in a saccade by the rotational angle of the saccade.

FIG. 10 shows a result of comparison, between the levels of attention reduction (normal, mild and severe), of the microsaccade rate, the relative velocity of a saccade, the average value of the degree of eyelid opening, the standard deviation of the degree of eyelid opening and the duration of an eye-blinking at the point in time when a response to each trial in the PVT occurs. As can be seen from FIG. 10, there is a significant difference in microsaccade rate, relative velocity of a saccade, average value of the degree of eyelid opening, standard deviation of the degree of eyelid opening and duration of an eye-blinking between the three levels of attention reduction, "normal", "mild" and "severe". It can also be seen that the microsaccade rate may also be used as an index of attention.

A reduced attention state estimation system according to this embodiment is essentially the same as the reduced attention state estimation system according to the first embodiment but differs from the system according to the first embodiment in that the eyeball movement and eyelid activity-related information calculation unit 15 calculates whether a relevant section is the eye opening section, the eye closing section, or the eye-blinking section, whether an eye closing section is included in a cluster section, whether an eye opening section, an eye closing section or an eye-blinking section is included in a cluster section, the microsaccade rate and the relative velocity of a saccade for the eye opening section, the average value of the degree of eyelid opening and the standard deviation of the degree of eyelid opening for the eye opening section and the eye closing section, and the duration of an eye-blinking for the cluster section.

Next, an example of a reduced attention state estimation process performed by the reduced attention state estimation system according to this embodiment of the present invention will be described. A flowchart showing the example of the reduced attention state estimation process performed by the reduced attention state estimation system according to this embodiment is also the same as the flowchart for the first embodiment, and therefore, the reduced attention state estimation process according to this embodiment will be described with reference to FIG. 5.

[I] Teacher Data Acquisition Phase

In this embodiment, the Naive Bayes estimation is used as in the first embodiment. The procedure performed in the training data acquisition phase in this embodiment is basically the same as the procedure performed in the first embodiment but differs in that, in Step S105, the eyeball movement and eyelid activity-related information calculation unit 15 calculates the microsaccade rate, the relative velocity of a saccade, the average value of the degree of eyelid opening, the standard deviation of the degree of eyelid opening and the duration of an eye-blinking as the information concerning the eyeball movement and eyelid activity and stores these items of information in the storage unit 19. These various kinds of items of information concerning the eyeball movement and eyelid activity may be calculated in the same manner as described above, for example.

In Step S107, the prior probability and likelihood calculation unit 18 calculates the likelihoods for the items of information concerning the eyeball movement and eyelid activity and probability density functions for calculating the likelihood. The average value of the degree of eyelid opening, the standard deviation of the degree of eyelid opening and the duration of an eye-blinking are calculated in the same manner as in the first embodiment, and the microsaccade rate and the relative velocity of a saccade are calculated as described below.

For the microsaccade rate, a probability density function of a normal distribution is calculated from the average value ($\mu$) and the standard deviation ($\sigma$) for each attention reduction level according to the (formula 2). That is, an average value ($\mu_{18}$) and a standard deviation ($\sigma_{18}$) of the microsaccade rate for all the eye opening sections are determined for each attention reduction level, and a probability density function for each attention reduction level is calculated by substituting $\mu_{18}$ and $\sigma_{18}$ for $\mu$ and $\sigma$ in the formula (2).

For the relative velocity of a saccade, a probability density function of a normal distribution is calculated from the average value ($\mu$) and the standard deviation ($\sigma$) for each attention reduction level according to the formula (2). That is, an average value ($\mu_{19}$) and a standard deviation ($\sigma_{19}$) of the relative velocity of a saccade in each section are determined for each attention reduction level, and a probability density function for each attention reduction level is calculated by substituting $\mu_{19}$ and $\sigma_{19}$ for $\mu$ and $\sigma$ in the formula (2).

[II] Attention Assessment Calculation Phase

The procedure performed in the attention assessment calculation phase in this embodiment is basically the same as the procedure performed in the first embodiment but differs in that in Step S205, based on the eyeball movement and eyelid activity data measured by the eyeball movement and eyelid activity measurement unit 11 and the types of the sections determined by the section determination unit 13, the eyeball movement and eyelid activity-related information calculation unit 15 calculates the microsaccade rate, the relative velocity of a saccade, the average value of the degree of eyelid opening, the standard deviation of the degree of eyelid opening and the duration of an eye-blinking as the information concerning the eyeball movement and eyelid activity for each section determined by the section determination unit 13 in the same manner as in Step S105 in the training data acquisition phase described above Furthermore, in Step S207, the attention assessment unit 17 calculates the estimated probability of occurrence of each attention reduction level for each section according to the Naive Bayes estimation according to the (formula 1) based on the first prior probability in the Naive Bayes estimation, the likelihoods for the items of information concerning the eyeball movement and eyelid activity and the probability density functions for calculating the likelihoods, which are calculated in the training data acquisition phase and stored in the storage unit 19. Specifically, for each of the sections described below, the probability of occurrence of each attention reduction level is calculated by sequentially calculating the posterior probability for each item of information concerning the eyeball movement and eyelid activity for each attention reduction level by the Bayes update according to the formula (1), which is the Bayes' theorem, as described below. The order of calculation of the posterior probabilities of the items of information concerning the eyeball movement and eyelid activity is arbitrary because of the sequential rationality of the Bayes' theorem. An example will be described below.

(1) Eye Opening/Cluster Section

For an eye opening/cluster section (denoted by "a" in FIG. 1, for example), which is an eye opening section and cluster section, as the information concerning the eyeball movement and eyelid activity, whether the section is an eye opening section, an eye closing section or an eye-blinking section ($P(D_{1\text{-}1})$, $P(D_{1\text{-}2})$ or $P(D_{1\text{-}3})$), whether an eye opening section is included in the cluster section, an eye closing section or eye-blinking section ($P(D_{20\text{-}1})$, $P(D_{20\text{-}2})$), the microsaccade rate ($D_{18}$), the relative velocity of a saccade ($D_{19}$), the average value of the degree of eyelid opening ($D_7$), the standard deviation of the degree of eyelid opening ($D_8$) and the duration of an eye-blinking ($D_{12}$) are used.

(A) The average value of the degree of eyelid opening ($D_7$) for the relevant section is substituted for x in the probability density function (formula (2)) for each category determined in the training data acquisition phase to calculate the likelihood. From the prior probabilities $p(H_1)$, $p(H_2)$ and $p(H_3)$ calculated in the training data acquisition phase and the determined likelihood, the posterior probabilities ($P(H_1|D_7)$, $P(H_2|D_7)$, $P(H_3|D_7)$) for the average value of the degree of eyelid opening are calculated according to the formula (1).

(B) The standard deviation of the degree of eyelid opening ($D_8$) for the relevant section is substituted for x in the probability density function (formula (2)) for each category determined in the training data acquisition phase to calculate the likelihood. The posterior probabilities determined in (A) described above are used as prior probabilities. From these prior probabilities and the determined likelihood, the posterior probabilities ($P(H_1|D_8)$, $P(H_2|D_8)$, $P(H_3|D_8)$) for the standard deviation of the degree of eyelid opening are calculated according to the formula (1).

(C) The posterior probabilities determined in (B) described above are used as prior probabilities. From these prior probabilities and the likelihoods ($P(D_{1-1}|H_1)$, $P(D_{1-1}|H_2)$, $P(D_{1-1}|H_3)$) determined in the training data acquisition phase, the posterior probabilities ($P(H_1|D_{1-1})$, $P(H_2|D_{1-1})$, $P(H_3|D_{1-1})$) of whether the section is an eye opening section, whether the section is an eye closing section and whether the section is an eye-blinking section are calculated according to the formula (1).

(D) The posterior probabilities determined in (C) described above are used as prior probabilities. From these prior probabilities and the likelihoods ($P(D_{20-1}|H_i)$, $P(D_{20-1}|H_2)$, $P(D_{20-1}|H_3)$) determined in the training data acquisition phase, the posterior probabilities ($P(H_i|D_{20-1})$, $P(H_2|D_{20-1})$, $P(H_3|D_{20-1})$) of whether an eye opening section, an eye closing section, or an eye-blinking section is included in the cluster section are calculated according to the formula (1).

(E) If an eyeball movement occurs in the relevant section, the microsaccade rate ($D_{18}$) for the relevant section is substituted for x in the probability density function (formula (2)) for each category determined in the training data acquisition phase to calculate the likelihood. The posterior probabilities determined in (D) described above are used as prior probabilities. From these prior probabilities and the determined likelihood, the posterior probabilities ($P(H_i|D_{18})$, $P(H_2|D_{18})$, $P(H_3|D_{18})$) for the microsaccade rate are calculated according to the formula (1).

(F) If an eyeball movement occurs in the relevant section, the relative velocity of a saccade ($D_{19}$) for the relevant section is substituted for x in the probability density function (formula (2)) for each category determined in the training data acquisition phase to calculate the likelihood. The posterior probabilities determined in (E) described above are used as prior probabilities. From these prior probabilities and the determined likelihood, the posterior probabilities ($P(H_i|D_{19})$, $P(H_2|D_{19})$, $P(H_3|D_{19})$) for the relative velocity of a saccade are calculated according to the formula (1).

(G) The duration of an eye-blinking ($D_{12}$) for the cluster section containing the relevant section is substituted for x in the probability density function (formula (2)) for each category determined in the training data acquisition phase to calculate the likelihood. The posterior probabilities determined in (J) described above are used as prior probabilities. From these prior probabilities and the likelihood, the posterior probabilities ($P(H_i|D_{12})$, $P(H_2|D_{12})$, $P(H_3|D_{12})$) for the duration of an eye-blinking are calculated according to the formula (1). The posterior probabilities are the estimated probabilities of occurrence of the attention reduction levels.

(2) Eye Closing/Cluster Section

For an eye closing/cluster section (denoted by "b" in FIG. 1, for example), which is an eye closing section and cluster section, whether the section is an eye opening section, an eye closing section or an eye-blinking section ($P(D_{1-1})$, $P(D_{1-2})$ or $P(D_{1-3})$), whether an eye closing section is included in the cluster section ($P(D_{2-1})$, $P(D_{2-2})$), the average value of the degree of eyelid opening ($D_7$), the standard deviation of the degree of eyelid opening ($D_8$) and the duration of an eye-blinking ($D_{12}$) are used as the information concerning the eyeball movement and eyelid activity to calculate the estimated probability of occurrence of each attention reduction level, as with the eye opening/cluster section of (1) described above.

(3) Eye-Blinking/Cluster Section

For an eye-blinking/cluster section (denoted by "c" in FIG. 1, for example), which is an eye-blinking section and cluster section, whether the section is an eye opening section, an eye closing section or an eye-blinking section ($P(D_{1-1})$, $P(D_{1-2})$ or $P(D_{1-3})$), whether an eye opening section is included in the cluster section, an eye closing section or eye-blinking section ($P(D_{20-1})$, $P(D_{20-2})$) and the duration of an eye-blinking ($D_{12}$) are used as the information concerning the eyeball movement and eyelid activity to calculate the estimated probability of occurrence of each attention reduction level, as with the eye opening/cluster section of (1) described above.

(4) Eye Opening/Non-Cluster Section

For eye opening/non-cluster section (denoted by "d" in FIG. 1, for example), which is an eye opening section and non-cluster section, whether the section is an eye opening section, an eye closing section or an eye-blinking section ($P(D_{1-1})$, $P(D_{1-2})$ or $P(D_{1-3})$), whether an eye opening section is included in the cluster section, an eye closing section or eye-blinking section ($P(D_{20-1})$, $P(D_{20-2})$), the microsaccade rate ($D_{18}$), the relative velocity of a saccade ($D_{19}$), the average value of the degree of eyelid opening ($D_7$) and the standard deviation of the degree of eyelid opening ($D_8$) are used as the information concerning the eyeball movement and eyelid activity to calculate the estimated probability of occurrence of each attention reduction level, as with the eye opening/cluster section of (1) described above.

(5) Eye Closing/Non-Cluster Section

For an eye closing/non-cluster section (denoted by "e" in FIG. 1, for example), which is an eye closing section and non-cluster section, whether the section is an eye opening section, an eye closing section or an eye-blinking section ($P(D_{1-1})$, $P(D_{1-2})$ or $P(D_{1-3})$), whether an eye closing section is included in the cluster section ($P(D_{2-1})$, $P(D_{2-2})$), the average value of the degree of eyelid opening ($D_7$) and the standard deviation of the degree of eyelid opening ($D_8$) are used as the information concerning the eyeball movement and eyelid activity to calculate the estimated probability of occurrence of each attention reduction level, as with the eye opening/cluster section of (1) described above.

(6) Eye-Blinking/Non-Cluster Section

For an eye-blinking/non-cluster section (denoted by "f" in FIG. 1, for example), which is an eye-blinking section and non-cluster section, whether the section is an eye opening section, an eye closing section or an eye-blinking section ($P(D_{1-1})$, $P(D_{1-2})$ or $P(D_{1-3})$) and whether an eye opening section is included in the cluster section, an eye closing section or eye-blinking section ($P(D_{20-1})$, $P(D_{20-2})$) are used as the information concerning the eyeball movement and eyelid activity to calculate the estimated probability of occurrence of each attention reduction level, as with the eye opening/cluster section of (1) described above.

As in the first embodiment, the attention assessment unit 17 may further determine the attention level per assessment time based on the determined estimated probability of occurrence of each attention reduction level. In the experiment described above, the training data acquisition phase described above was conducted for each subject in the first half of sessions (the first to tenth sessions), and the attention assessment calculation phase described above was conducted based on the personal training data of each subject in the second half of sessions (the eleventh to twenty-second sessions). For the data obtained in the experiment described above, FIG. 11 shows the probability of occurrence of each attention reduction level per 20 minutes determined in the PVT, the estimated probability of occurrence of each attention reduction level per 20 minutes determined in the reduced attention state estimation method according to the embodiment under the condition that the attention assessment is calculated based on the personal training data of each subject (the estimation method conducted under this condition will be referred to as a "tailor-made type", hereinafter), a correlation coefficient (r) therebetween, and the PERCLOS value per 20 minutes. For the data obtained in the experiment described above, FIG. 11 also shows the probability of occurrence of each attention reduction level per 20 minutes determined in the PVT, the estimated probability of occurrence of each attention reduction level per 20 minutes determined in the reduced attention state estimation method according to the embodiment under the condition that the attention assessment for the data on all the sessions of each subject is made based on the data on all the sessions of the other fifteen subjects as training data (the estimation method conducted under this condition will be referred to as a "ready-made type", hereinafter), a correlation coefficient (r) therebetween, and the PERCLOS value per 20 minutes.

Figure 11:
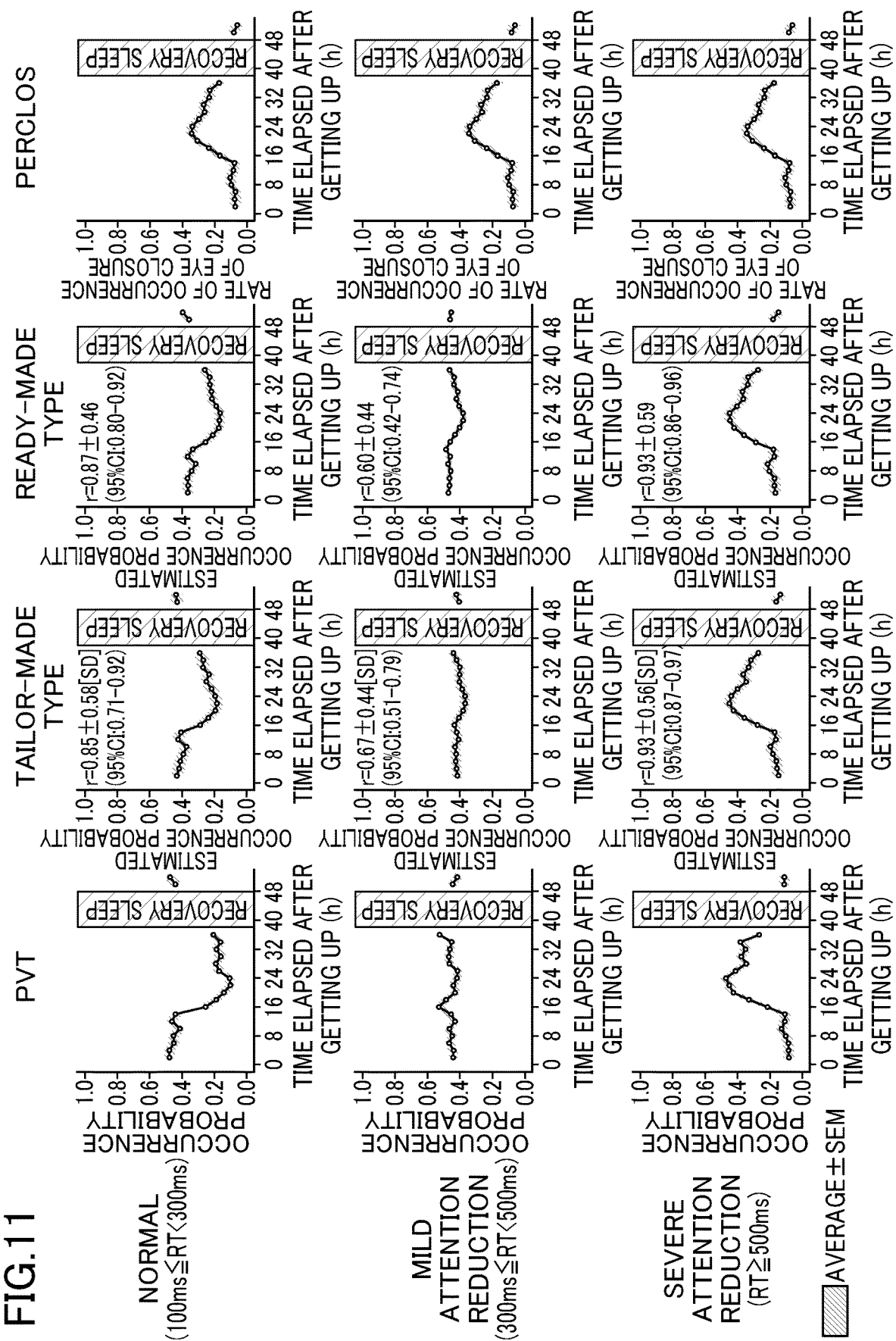
FIG. 11 shows the probability of occurrence of each attention reduction level per 20 minutes determined in the PVT, the estimated probability of occurrence of each attention reduction level per 20 minutes determined in the reduced attention state estimation method according to a second embodiment of the present invention, a correlation coefficient therebetween, and the PERCLOS value per 20 minutes.

As can be seen from FIG. 11, the variation of the estimated probability of occurrence of each attention reduction level per 20 minutes determined in the reduced attention state estimation methods according to this embodiment of both the tailor-made type and the ready-made type well matches the variation of the estimated probability of occurrence of each attention reduction level per 20 minutes determined in the PVT. It is also shown that, not only for the normal attention reduction level and the severe attention reduction level but also for the mild attention reduction level, there is a significant correlation between the occurrence probability determined in the PVT and the estimated occurrence probability determined in the reduced attention state estimation method according to this embodiment. This shows that, according to the reduced attention state estimation method according to this embodiment, various levels of attention reduction may be continuously measured without giving any test.

It is also shown that for the normal attention reduction level and the mild attention reduction level, the PERCLOS value was smaller than the occurrence probability determined in the PVT. On the other hand, it is also shown that for the severe attention reduction level, the occurrence probability determined in the PVT highly matched the estimated occurrence probability determined in the reduced attention state estimation method according to this embodiment and the PERCLOS value.

Figure 12:
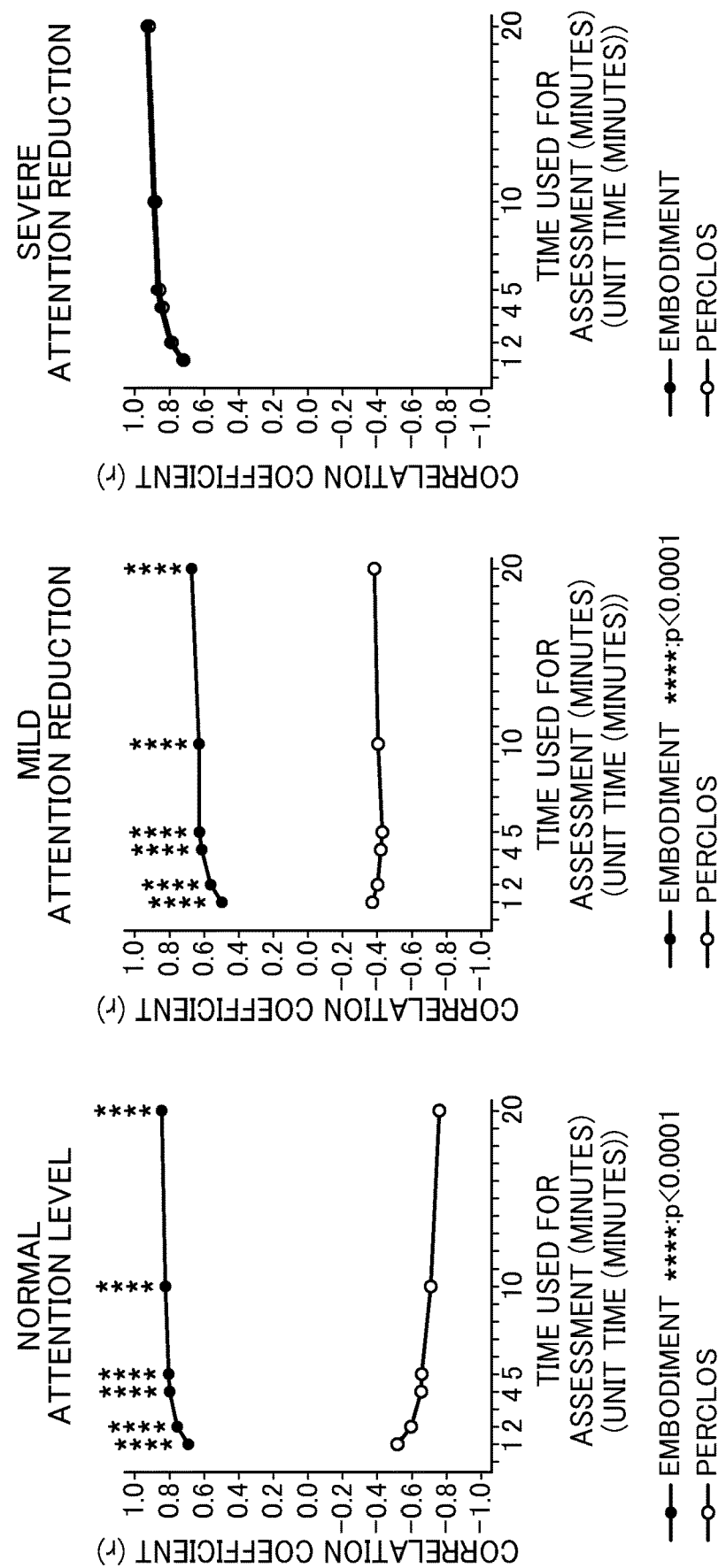
FIG. 12 shows, for each attention reduction level, the correlation coefficient determined per unit assessment time between the occurrence probability determined in the PVT, and the estimated occurrence probability determined in the reduced attention state estimation method of a tailor-made type according to the second embodiment of the present invention and the PERCLOS value.

FIG. 12 shows, for each attention reduction level, the correlation efficient (r) determined per unit assessment time between the occurrence probability determined in the PVT, and the estimated occurrence probability determined in the reduced attention state estimation method of the tailor-made type according to this embodiment and the PERCLOS value.

Figure 13:
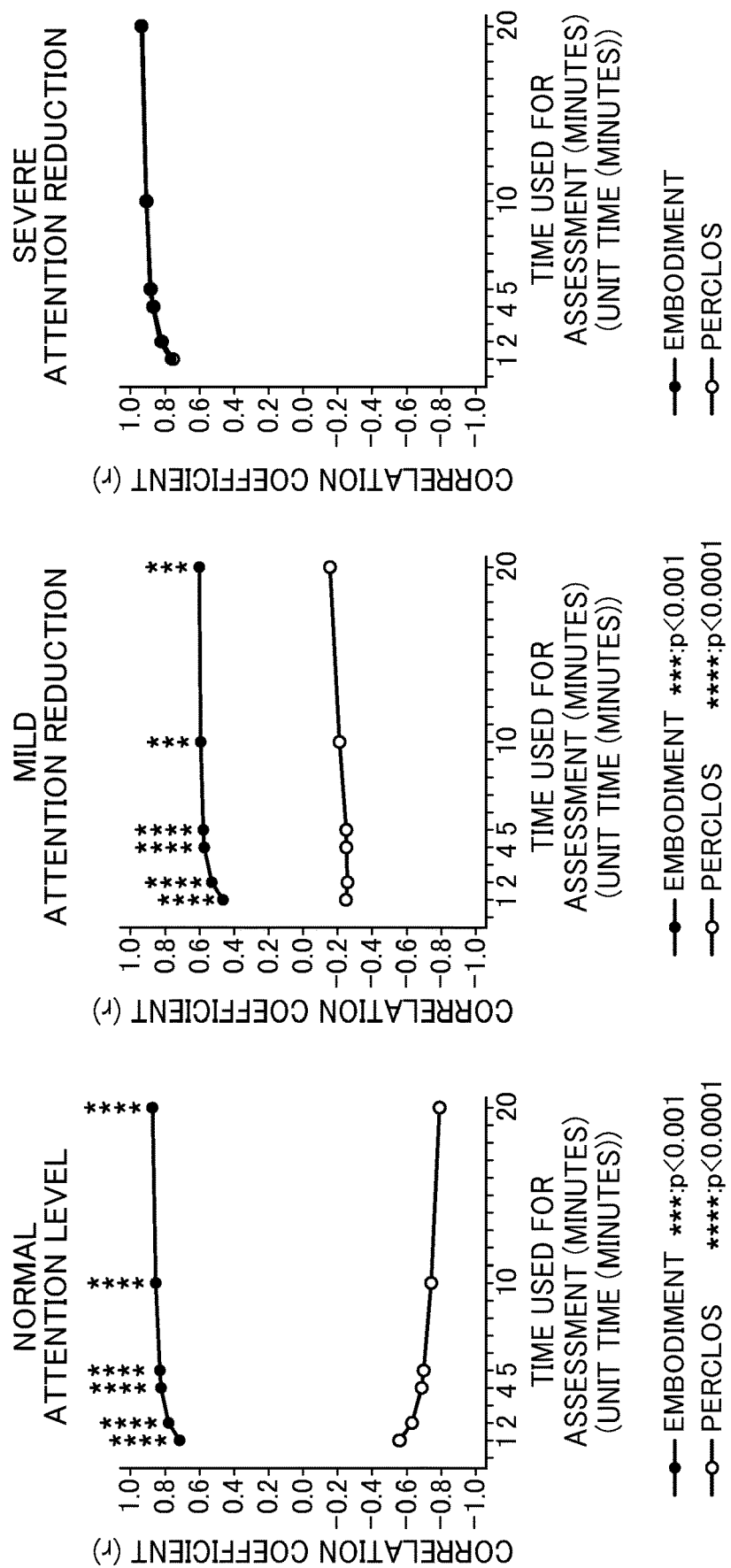
FIG. 13 shows, for each attention reduction level, the correlation coefficient determined per unit assessment time between the occurrence probability determined in the PVT, and the estimated occurrence probability determined in the reduced attention state estimation method of a ready-made type according to the second embodiment of the present invention and the PERCLOS value.

FIG. 13 shows, for each attention reduction level, the correlation efficient (r) determined per unit assessment time between the occurrence probability determined in the PVT, and the estimated occurrence probability determined in the reduced attention state estimation method of the ready-made type according to this embodiment and the PERCLOS value.

As can be seen from FIGS. 12 and 13, for the normal attention reduction level and the mild attention reduction level, the estimated occurrence probability determined in the reduced attention state estimation method of both the tailor-made type and the ready-made type showed a high positive correlation with the occurrence probability determined in the PVT, whereas the PERCLOS value showed a negative correlation with the occurrence probability determined in the PVT. For the severe attention reduction level, the correlation between the estimated occurrence probability determined in the reduced attention state estimation method of both the tailor-made type and the ready-made type according to this embodiment and the occurrence probability determined in the PVT was slightly higher than the correlation between the PERCLOS value and the occurrence probability determined in the PVT. It is also shown that, although there was no significant difference in correlation with the probability of occurrence of the severe attention reduction determined in the PVT between the reduced attention state estimation method according to this embodiment and the PERCLOS, the probability of occurrence of the normal attention reduction level and the mild attention reduction level exhibited a higher correlation between the reduced attention state estimation method according to this embodiment and the PVT than the correlation between the PERCLOS and the PVT. This shows that the reduced attention state estimation method according to this embodiment can more accurately measure attention than the conventional method.

Figure 14:
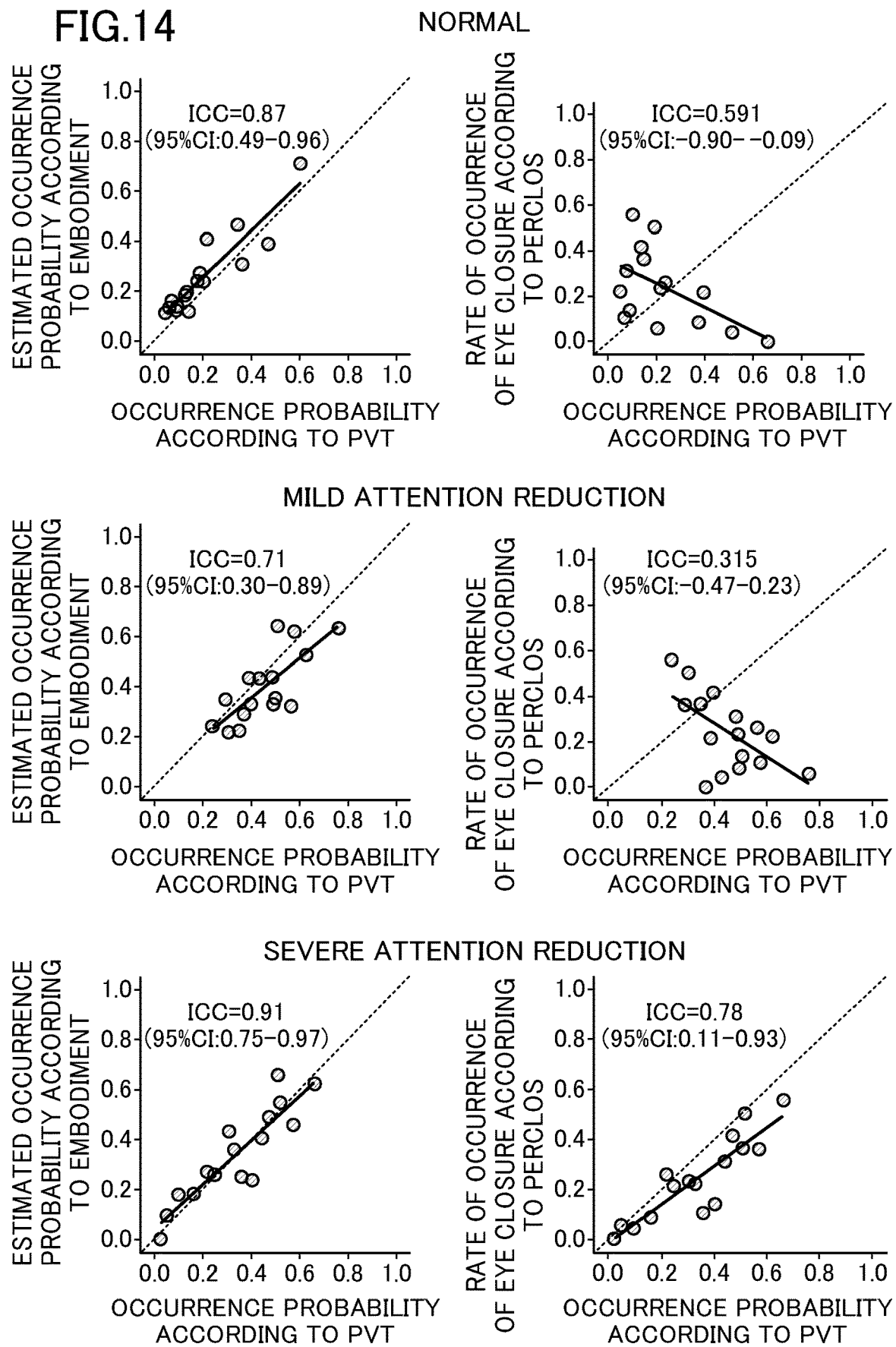
FIG. 14 shows scatter diagrams showing relationships between the PVT, and the reduced attention state estimation method of the tailor-made type according to the second embodiment of the present invention and the PERCLOS and linear regression lines.
Figure 15:
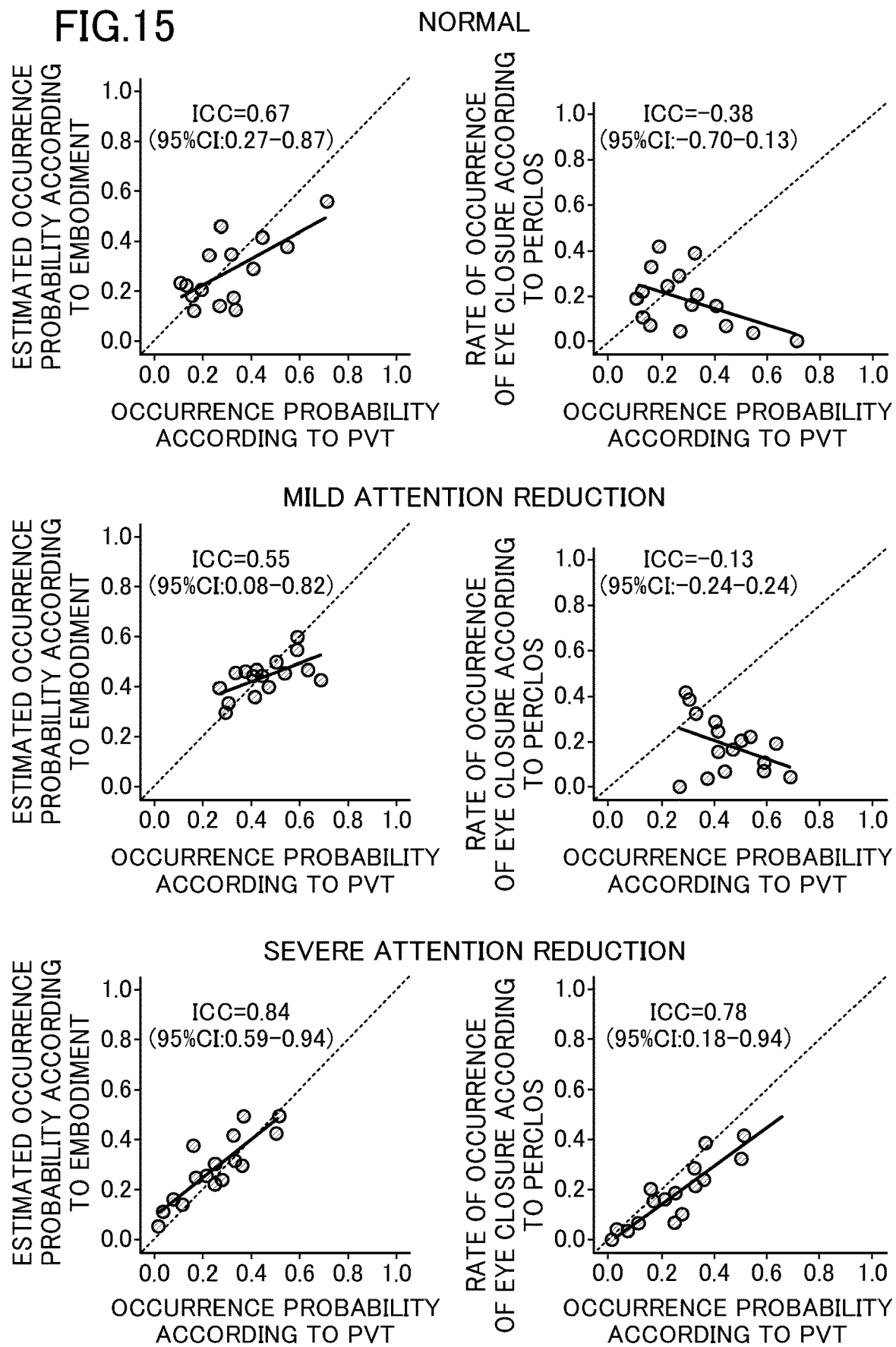
FIG. 15 shows scatter diagrams showing relationships between the PVT, and the reduced attention state estimation method of the ready-made type according to the second embodiment of the present invention and the PERCLOS and linear regression lines.

The intraclass correlation coefficient (ICC) was then used to examine whether the probability of occurrence of each attention reduction level determined in the PVT perfectly matched (or had a relationship expressed as y=x with) the estimated probability of occurrence of each attention reduction level determined in the reduced attention state estimation method according to this embodiment. In the examination, for the tailor-made type, an average value over all the sessions in the attention assessment calculation phase for each subject was used. For the ready-made type, an average value over all the sessions (excluding the first session and the twentieth session conducted immediately after waking from the reference night sleep and the recovery sleep, respectively) of each subject was used. FIG. 14 shows scatter diagrams showing relationships between the PVT, and the reduced attention state estimation method of the tailor-made type according to this embodiment and the PERCLOS and linear regression lines for the sixteen cases. FIG. 15 shows scatter diagrams showing relationships between the PVT, and the reduced attention state estimation method of the ready-made type according to this embodiment and the PERCLOS and linear regression lines for the sixteen cases.

If the ICC is 0.61 to 0.80, the degree of perfect matching is determined to be "substantial". If the ICC is 0.81 to 1.00, the degree of perfect matching is determined to be "almost perfect". If 95% CI is higher than 0, it can be said that the values of two indices significantly positively perfectly match each other. For the method of the tailor-made type according to this embodiment, the ICC was higher than 0.7 for all the attention reduction level, and 95% CI was higher than 0. That is, for the normal attention reduction level and the severe attention reduction level, the degree of perfect matching was determined to be "almost perfect", and for the mild attention reduction level, the degree of perfect matching was determined to be "substantial". Therefore, the estimated occurrence probability determined in the reduced attention state estimation method of the tailor-made type according to this embodiment can be replaced with the occurrence probability determined in the PVT. For the method of the ready-made type according to this embodiment, the ICC was 0.84 for the severe attention reduction level, and the degree of perfect matching was determined to be "almost perfect", whereas the ICC was lower than 0.7 for the normal attention reduction level and the mild attention reduction level. This shows that the occurrence probability determined in the method of the ready-made type according to this embodiment significantly matched the occurrence probability determined in the PVT, although the method of the ready-made type was less accurate than the method of the tailor-made type.

On the other hand, the PERCLOS value showed a negative correlation with the occurrence probability determined in the PVT for the normal attention reduction level and the mild attention reduction level. For the severe attention reduction level, the value of the ICC between the PERCLOS and the PVT was higher than 0.7, and the PERCLOS and the PVT exhibited a high degree of perfect matching. However, the value of the ICC between the PERCLOS and the PVT indicates a degree of perfect matching determined to be "substantial", and the reduced attention state estimation method of both the tailor-made type and the ready-made type according to this embodiment, the ICC for which indicated a degree of perfect matching determined to be "almost perfect", provided a higher degree of perfect matching.

As can be seen from the above description, in degree of perfect matching of the occurrence probability for all the categories of the attention reduction levels, the reduced attention state estimation method of both the tailor-made type and the ready-made type according to this embodiment is superior to the PERCLOS, and the estimated occurrence probability determined in the reduced attention state estimation method according to this embodiment may be used as it is as the estimated probability of occurrence of attention reduction measured in the PVT. That is, it can be seen that the reduced attention state estimation method according to this embodiment facilitates reference to the knowledge of the PVT already accumulated in many prior researches. Since even the estimated occurrence probability determined in the reduced attention state estimation method of the ready-made type may be used as the estimated occurrence probability of attention reduction measured in the PVT, the attention reduction level may be highly advantageously estimated without acquiring personal training data of each subject.

As can be seen from the above description, whether the method is of the tailor-made type or the ready-made type, the reduced attention state estimation method according to this embodiment can simply continuously measure various levels of attention reduction and facilitates reference to the knowledge of the PVT already accumulated in many prior researches.

Furthermore, the reduced attention state estimation method of the tailor-made type according to this embodiment can accurately estimate the occurrence probability with a reduced number of indices.

The sharpness of microsaccade used in the first embodiment is more difficult to measure than the other indices of attention. In this embodiment, however, the sharpness of microsaccade is not used, so that the reduced attention state may be more easily estimated.

Although, in this embodiment, five indices including the microsaccade rate, the relative velocity of a saccade, the average value of the degree of eyelid opening, the standard deviation of the degree of eyelid opening and the duration of an eye-blinking are used as the items of information concerning the eyeball movement and eyelid activity used for estimating the reduced attention state, the indices that may be used are not limited to these five indices. The reduced attention state may be estimated using any number of indices selected from among these five indices or using any number of indices selected from among these five indices and any number of additional indices of attention.

Although the present invention has been described with regard to some embodiments for the illustrative purposes, the present invention is not limited to the embodiments. It will be obvious to those skilled in the art that various alterations or modifications may be made to the embodiments and details without departing from the scope of the present invention.

Concerning the above description, we further disclose the following items.

(1) A reduced attention state estimation system, comprising:

an eyeball movement and eyelid activity measurement unit that measures an eyeball movement and an eyelid activity of a subject to obtain eyeball movement and eyelid activity data;

a section determination unit that determines an eye opening section, an eye closing section, an eye-blinking section and a cluster section based on the eyeball movement and eyelid activity data;

an eyeball movement and eyelid activity-related information calculation unit that calculates, based on the eyeball movement and eyelid activity data, at least one of a microsaccade rate for each eye opening section, a sharpness of microsaccade for each eye opening section, a standard deviation of a degree of eyelid opening for each eye opening section and/or each eye closing section, a short-time eye-closure occurrence rate, which is a rate of occurrence of an eye closure having a duration shorter than a predetermined time, for each cluster section, and a long-time eye-closure occurrence rate, which is a rate of occurrence of an eye closure having a duration equal to or longer than the predetermined time, for each cluster section; and an attention assessment unit that determines at least one of an attention assessment for an eye opening/cluster section, which is an eye opening section and cluster section, based on at least one of the microsaccade rate, the sharpness of microsaccade, the standard deviation of the degree of eyelid opening, the short-time eye-closure occurrence rate and the long-time eye-closure occurrence rate for each eye opening section, an attention assessment for an eye closing/cluster section, which is an eye closing section and cluster section, based on at least one of the standard deviation of the degree of eyelid opening, the short-time eye-closure occurrence rate and the long-time eye-closure occurrence rate, an attention assessment for an eye-blinking/cluster section, which is an eye-blinking section and cluster section, based on at least one of the short-time eye-closure occurrence rate and the long-time eye-closure occurrence rate, an attention assessment for an eye opening/non-cluster section, which is an eye opening section and non-cluster section, based on at least one of the microsaccade rate, the sharpness of microsaccade and the standard deviation of the degree of eyelid opening, and an attention assessment for an eye closing/non-cluster section, which is an eye closing section and non-cluster section, based on at least the standard deviation of the degree of eyelid opening.

(2) The reduced attention state estimation system according to Item (1), wherein the eyeball movement and eyelid activity-related information calculation unit further calculates, based on the eyeball movement and eyelid activity data, one of whether a relevant section is an eye opening section, an eye closing section or an eye-blinking section, whether an eye opening section or an eye-blinking section is included in a cluster section, whether an eye closing section is included in a cluster section, a frequency of microsaccades, a duration of an eye opening section, an average value of the degree of eyelid opening, a frequency of eye-blinkings, an inverse of a relative velocity of an eyelid closure at an eyelid closing time, an inverse of a relative velocity of an eyelid opening at an eyelid opening time, a duration of an eye-blinking, a duration of a closed eye in an eye-blinking, a rate of occurrence of eye-blinkings, and a duration of an eye closing section, the attention assessment unit determines at least one of an attention assessment for the eye opening/cluster section, which is an eye opening section and cluster section, based on at least one of the microsaccade rate, the sharpness of microsaccade, the standard deviation of the degree of eyelid opening, the short-time eye-closure occurrence rate and the long-time eye-closure occurrence rate for the eye opening section, and at least one of whether a relevant section is an eye opening section, an eye closing section or an eye-blinking section, whether an eye opening section or an eye-blinking section is included in a cluster section, the frequency of microsaccades, the duration of an eye opening section, the average value of the degree of eyelid opening, the frequency of eye-blinkings, the inverse of a relative velocity of an eyelid closure at an eyelid closing time, the inverse of a relative velocity of an eyelid opening at an eyelid opening time, the duration of an eye-blinking, the duration of a closed eye in an eye-blinking and the rate of occurrence of eye-blinkings, an attention assessment for the eye closing/cluster section, which is an eye closing section and cluster section, based on at least one of the standard deviation of the degree of eyelid opening, the short-time eye-closure occurrence rate and the long-time eye-closure occurrence rate, and at least one of whether a relevant section is an eye opening section, an eye closing section or an eye-blinking section, whether an eye closing section is included in a cluster section, the duration of an eye closing section, the average value of the degree of eyelid opening, the frequency of eye-blinkings, the inverse of a relative velocity of an eyelid closure at an eyelid closing time, the inverse of a relative velocity of an eyelid opening at an eyelid opening time, the duration of an eye-blinking, the duration of a closed eye in an eye-blinking and the rate of occurrence of eye-blinkings, an attention assessment for an eye-blinking/cluster section, which is an eye-blinking section and cluster section, based on at least one of the short-time eye-closure occurrence rate and the long-time eye-closure occurrence rate, and at least one of whether a relevant section is an eye opening section, an eye closing section or an eye-blinking section, whether an eye opening section or an eye-blinking section is included in a cluster section, the frequency of eye-blinkings, the inverse of a relative velocity of an eyelid closure at an eyelid closing time, the inverse of a relative velocity of an eyelid opening at an eyelid opening time, the duration of an eye-blinking, the duration of a closed eye in an eye-blinking and the rate of occurrence of eye-blinkings, an attention assessment for an eye opening/non-cluster section, which is an eye opening section and non-cluster section, based on at least one of the microsaccade rate, the sharpness of microsaccade and the standard deviation of the degree of eyelid opening for each eye opening section, and at least one of whether a relevant section is an eye opening section, an eye closing section or an eye-blinking section, whether an eye opening section or an eye-blinking section is included in a cluster section, the frequency of microsaccades, the duration of an eye opening section and the average value of the degree of eyelid opening, an attention assessment for an eye closing/non-cluster section, which is an eye closing section and non-cluster section, based on the standard deviation of the degree of eyelid opening and at least one of whether a relevant section is an eye opening section, an eye closing section or an eye-blinking section, the duration of an eye closing section and the average value of the degree of eyelid opening, and an attention assessment for an eye-blinking/non-cluster section, which is an eye-blinking section and non-cluster section, based on at least one of whether a relevant section is an eye opening section, an eye closing section or an eye-blinking section and whether an eye opening section or an eye-blinking section is included in a cluster section.

(3) The reduced attention state estimation system according to Item (1), wherein the eyeball movement and eyelid activity-related information calculation unit further calculates, based on the eyeball movement and eyelid activity data, whether a relevant section is an eye opening section, an eye closing section or an eye-blinking section, whether an eye opening section or an eye-blinking section is included in a cluster section, whether an eye closing section is included in a cluster section, a sharpness of microsaccade, a frequency of microsaccades, a duration of an eye opening section, a frequency of eye-blinkings, an inverse of a relative velocity of an eyelid closure at an eyelid closing time, an inverse of a relative velocity of an eyelid opening at an eyelid opening time, a duration of a closed eye in an eye-blinking, a rate of occurrence of eye-blinkings, and a duration of an eye closing section, the attention assessment unit determines at least one of an attention assessment for the eye opening/cluster section, which is an eye opening section and cluster section, based on at least one of the microsaccade rate, the relative velocity of a saccade, the standard deviation of the degree of eyelid opening, an average value of the degree of eyelid opening, and a duration of an eye-blinking, and at least one of whether a relevant section is an eye opening section, an eye closing section or an eye-blinking section, whether an eye opening section or an eye-blinking section is included in a cluster section, the sharpness of microsaccade, the frequency of microsaccades, the duration of an eye opening section, the frequency of eye-blinkings, the inverse of a relative velocity of an eyelid closure at an eyelid closing time, the inverse of a relative velocity of an eyelid opening at an eyelid opening time, the duration of a closed eye in an eye-blinking and the rate of occurrence of eye-blinkings, an attention assessment for the eye closing/cluster section, which is an eye closing section and cluster section, based on at least one of the standard deviation of the degree of eyelid opening, the average value of the degree of eyelid opening and the duration of an eye-blinking, and at least one of whether a relevant section is an eye opening section, an eye closing section or an eye-blinking section, whether an eye closing section is included in a cluster section, the duration of an eye closing section, the frequency of eye-blinkings, the inverse of a relative velocity of an eyelid closure at an eyelid closing time, the inverse of a relative velocity of an eyelid opening at an eyelid opening time, the duration of a closed eye in an eye-blinking and the rate of occurrence of eye-blinkings, an attention assessment for an eye-blinking/cluster section, which is an eye-blinking section and cluster section, based on at least one of the duration of an eye-blinking, and at least one of whether a relevant section is an eye opening section, an eye closing section or an eye-blinking section, whether an eye opening section or an eye-blinking section is included in a cluster section, the frequency of eye-blinkings, the inverse of a relative velocity of an eyelid closure at an eyelid closing time, the inverse of a relative velocity of an eyelid opening at an eyelid opening time, the duration of a closed eye in an eye-blinking and the rate of occurrence of eye-blinkings, an attention assessment for an eye opening/non-cluster section, which is an eye opening section and non-cluster section, based on at least one of the microsaccade rate, the relative velocity of a saccade, the standard deviation of the degree of eyelid opening and the average value of the degree of eyelid opening, and at least one of whether a relevant section is an eye opening section, an eye closing section or an eye-blinking section, whether an eye opening section or an eye-blinking section is included in a cluster section, the frequency of microsaccades and the duration of an eye opening section, an attention assessment for an eye closing/non-cluster section, which is an eye closing section and non-cluster section, based on at least one of the standard deviation of the degree of eyelid opening and the average value of the degree of eyelid opening, and at least one of whether a relevant section is an eye opening section, an eye closing section or an eye-blinking section and the duration of an eye closing section, and an attention assessment for an eye-blinking/non-cluster section, which is an eye-blinking section and non-cluster section, based on at least one of whether a relevant section is an eye opening section, an eye closing section or an eye-blinking section and whether an eye opening section or an eye-blinking section is included in a cluster section.

(4) A reduced attention state estimation system, comprising:

an eyeball movement and eyelid activity measurement unit that measures an eyeball movement and an eyelid activity of a subject to obtain eyeball movement and eyelid activity data;

a section determination unit that determines an eye opening section, an eye closing section, an eye-blinking section and a cluster section based on the eyeball movement and eyelid activity data;

an eyeball movement and eyelid activity-related information calculation unit that calculates, based on the eyeball movement and eyelid activity data, at least two of a microsaccade rate for each eye opening section, a relative velocity of a saccade for each eye opening section, a standard deviation of a degree of eyelid opening for each eye opening section and/or each eye closing section, an average value of a degree of eyelid opening for each eye opening section and/or each eye closing section and a duration of an eye-blinking for each cluster section; and an attention assessment unit that determines at least one of an attention assessment for an eye opening/cluster section, which is an eye opening section and cluster section, based on at least two of the microsaccade rate, the relative velocity of a saccade, the standard deviation of the degree of eyelid opening, the average value of the degree of eyelid opening and the duration of an eye-blinking, an attention assessment for an eye closing/cluster section, which is an eye closing section and cluster section, based on at least two of the standard deviation of the degree of eyelid opening, the average value of the degree of eyelid opening and the duration of an eye-blinking, an attention assessment for an eye opening/non-cluster section, which is an eye opening section and non-cluster section, based on at least two of the microsaccade rate, the relative velocity of a saccade, the standard deviation of the degree of eyelid opening and the average value of the degree of eyelid opening, and an attention assessment for an eye closing/non-cluster section, which is an eye closing section and non-cluster section, based on at least the standard deviation of the degree of eyelid opening and the average value of the degree of eyelid opening.

(5) A reduced attention state estimation system, comprising:

an eyeball movement and eyelid activity measurement unit that measures an eyeball movement and an eyelid activity of a subject to obtain eyeball movement and eyelid activity data;

a section determination unit that determines an eye opening section, an eye closing section, an eye-blinking section and a cluster section based on the eyeball movement and eyelid activity data;

an eyeball movement and eyelid activity-related information calculation unit that calculates at least one of whether a relevant section is an eye opening section, an eye closing section or an eye-blinking section, whether an eye opening section or an eye-blinking section is included in a cluster section, whether an eye closing section is included in a cluster section, a sharpness of microsaccade, a frequency of microsaccades, a duration of an eye opening section, a frequency of eye-blinkings, an inverse of a relative velocity of an eyelid closure at an eyelid closing time, an inverse of a relative velocity of an eyelid opening at an eyelid opening time, a duration of a closed eye in an eye-blinking, a rate of occurrence of eye-blinkings and a duration of an eye closing section based on a microsaccade rate for each eye opening section, a relative velocity of a saccade for each eye opening section, a standard deviation of a degree of eyelid opening for each eye opening section and/or each eye closing section, an average value of the degree of eyelid opening for each eye opening section and/or each eye closing section, a duration of an eye-blinking for each cluster section, and the eyeball movement and eyelid activity data; and an attention assessment unit that determines at least one of an attention assessment for an eye opening/cluster section, which is an eye opening section and cluster section, based on at least one of the microsaccade rate, the relative velocity of a saccade, the standard deviation of the degree of eyelid opening, the average value of the degree of eyelid opening and the duration of an eye-blinking, and at least one of whether a relevant section is an eye opening section, an eye closing section or an eye-blinking section, whether an eye opening section or an eye-blinking section is included in a cluster section, the sharpness of microsaccade, the frequency of microsaccades, the duration of an eye opening section, the frequency of eye-blinkings, the inverse of a relative velocity of an eyelid closure at an eyelid closing time, the inverse of a relative velocity of an eyelid opening at an eyelid opening time, the duration of a closed eye in an eye-blinking and the rate of occurrence of eye-blinkings, an attention assessment for an eye closing/cluster section, which is an eye closing section and cluster section, based on at least one of the standard deviation of the degree of eyelid opening, the average value of the degree of eyelid opening and the duration of an eye-blinking, and at least one of whether a relevant section is an eye opening section, an eye closing section or an eye-blinking section, whether an eye closing section is included in a cluster section, the duration of an eye closing section, the frequency of eye-blinkings, the inverse of a relative velocity of an eyelid closure at an eyelid closing time, the inverse of a relative velocity of an eyelid opening at an eyelid opening time, the duration of a closed eye in an eye-blinking, and the rate of occurrence of eye-blinkings, an attention assessment for an eye-blinking/cluster section, which is an eye-blinking section and cluster section, based on at least one of the duration of eye-blinkings, whether a relevant section is an eye opening section, an eye closing section or an eye-blinking section, whether an eye opening section or an eye-blinking section is included in a cluster section, the frequency of eye-blinkings, the inverse of a relative velocity of an eyelid closure at an eyelid closing time, the inverse of a relative velocity of an eyelid opening at an eyelid opening time, the duration of a closed eye in an eye-blinking and the rate of occurrence of eye-blinkings, an attention assessment for an eye opening/non-cluster section, which is an eye opening section and non-cluster section, based on at least one of the microsaccade rate, the relative velocity of a saccade, the standard deviation of the degree of eyelid opening and the average value of the degree of eyelid opening, and at least one of whether a relevant section is an eye opening section, an eye closing section or an eye-blinking section, whether an eye opening section or an eye-blinking section is included in a cluster section, the frequency of microsaccades and the duration of an eye opening section, an attention assessment for an eye closing/non-cluster section, which is an eye closing section and non-cluster section, based on at least one of the standard deviation of the degree of eyelid opening and the average value of the degree of eyelid opening, and at least one of whether a relevant section is an eye opening section, an eye closing section or an eye-blinking section and the duration of an eye closing section, and an attention assessment for an eye-blinking/non-cluster section, which is an eye-blinking section and non-cluster section, based on at least one of whether a relevant section is an eye opening section, an eye closing section or an eye-blinking section and whether an eye opening section or an eye-blinking section is included in a cluster section.

(6) The reduced attention state estimation system according to any one of Items (1) to (5), wherein the attention assessment is an estimated probability of occurrence of each attention reduction level determined by a Naive Bayes estimation.

(7) The reduced attention state estimation system according to Item (6), wherein the attention assessment is an estimated probability of occurrence of each attention reduction level per assessment time calculated based on the estimated probability of occurrence of each attention reduction level calculated for each of the eye opening/cluster section, the eye closing/cluster section, the eye-blinking/cluster section, the eye opening/non-cluster section, the eye closing/non-cluster section and the eye-blinking/non-cluster section.

(8) The reduced attention state estimation system according to Item (6) or (7), wherein a first prior probability in the Naive Bayes estimation is calculated based on training data derived from personal eyeball movement and eyelid activity data of the subject of the attention assessment.

(9) The reduced attention state estimation system according to Item (6) or (7), wherein a first prior probability in the Naive Bayes estimation is calculated based on training data derived from eyeball movement and eyelid activity data of a person other than the subject of the attention assessment, or from personal eyeball movement and eyelid activity data of the subject and eyeball movement and eyelid activity data of a person other than the subject.

(10) A reduced attention state estimation system, comprising:

an eyeball movement and eyelid activity measurement unit that measures an eyeball movement and an eyelid activity of a subject to obtain eyeball movement and eyelid activity data;

a section determination unit that determines an eye opening section based on the eyeball movement and eyelid activity data;

an eyeball movement and eyelid activity-related information calculation unit that calculates a microsaccade rate for each eye opening section and/or a sharpness of microsaccade for each eye opening section based on the eyeball movement and eyelid activity data; and an attention assessment unit that determines an attention assessment for the eye opening section based on at least the microsaccade rate and/or the sharpness of microsaccade for the eye opening section.

(11) A reduced attention state estimation system, comprising:

an eyeball movement and eyelid activity measurement unit that measures an eyeball movement and an eyelid activity of a subject to obtain eyeball movement and eyelid activity data;

a section determination unit that determines an eye opening section based on the eyeball movement and eyelid activity data;

an eyeball movement and eyelid activity-related information calculation unit that calculates a microsaccade rate and/or a relative velocity of a saccade for each eye opening section based on the eyeball movement and eyelid activity data; and an attention assessment unit that determines an attention assessment for the eye opening section based on at least the microsaccade rate and/or the relative velocity of a saccade, wherein the attention assessment is any of three or more levels of attention reduction.

(12) A reduced attention state estimation system, comprising:

an eyeball movement and eyelid activity measurement unit that measures an eyeball movement and an eyelid activity of a subject to obtain eyeball movement and eyelid activity data;

a section determination unit that determines an eye opening section and/or an eye closing section based on the eyeball movement and eyelid activity data;

an eyeball movement and eyelid activity-related information calculation unit that calculates a standard deviation of a degree of eyelid opening and/or an average value of the degree of eyelid opening for each eye opening section and/or each eye closing section based on the eyeball movement and eyelid activity data; and an attention assessment unit that determines an attention assessment for the eye opening section and/or the eye closing section based on at least the standard deviation of the degree of eyelid opening and/or the average value of the degree of eyelid opening, wherein the attention assessment is any of three or more levels of attention reduction.

(13) A reduced attention state estimation system, comprising:

an eyeball movement and eyelid activity measurement unit that measures an eyeball movement and an eyelid activity of a subject to obtain eyeball movement and eyelid activity data;

a section determination unit that determines a cluster section based on the eyeball movement and eyelid activity data;

an eyeball movement and eyelid activity-related information calculation unit that calculates a duration of an eye-blinking for each cluster section based on the eyeball movement and eyelid activity data; and an attention assessment unit that determines an attention assessment for the cluster section based on at least the duration of an eye-blinking, wherein the attention assessment is any of three or more levels of attention reduction.

(14) A reduced attention state estimation system, comprising:

an eyeball movement and eyelid activity measurement unit that measures an eyeball movement and an eyelid activity of a subject to obtain eyeball movement and eyelid activity data;

a section determination unit that determines an eye opening section based on the eyeball movement and eyelid activity data;

an eyeball movement and eyelid activity-related information calculation unit that calculates a microsaccade rate and a relative velocity of a saccade for each eye opening section based on the eyeball movement and eyelid activity data; and an attention assessment unit that determines an attention assessment for the eye opening section based on at least the microsaccade rate and the relative velocity of a saccade.

(15) A reduced attention state estimation system, comprising:

an eyeball movement and eyelid activity measurement unit that measures an eyeball movement and an eyelid activity of a subject to obtain eyeball movement and eyelid activity data;

a section determination unit that determines an eye opening section and/or an eye closing section based on the eyeball movement and eyelid activity data;

an eyeball movement and eyelid activity-related information calculation unit that calculates a standard deviation of a degree of eyelid opening and an average value of the degree of eyelid opening for each eye opening section and/or each eye closing section based on the eyeball movement and eyelid activity data; and an attention assessment unit that determines an attention assessment for the eye opening section and/or the eye closing section based on at least the standard deviation of the degree of eyelid opening and the average value of the degree of eyelid opening.

(16) A reduced attention state estimation method, comprising:

a section determination step of determining an eye opening section, an eye closing section, an eye-blinking section and a cluster section based on eyeball movement and eyelid activity data obtained by measuring an eyeball movement and an eyelid activity of a subject;

an eyeball movement and eyelid activity-related information calculation step of calculating, based on the eyeball movement and eyelid activity data, at least one of a microsaccade rate for each eye opening section, a sharpness of microsaccade for each eye opening section, a standard deviation of a degree of eyelid opening for each eye opening section and/or each eye closing section, a short-time eye-closure occurrence rate, which is a rate of occurrence of an eye closure having a duration shorter than a predetermined time, for each cluster section, and a long-time eye-closure occurrence rate, which is a rate of occurrence of an eye closure having a duration equal to or longer than the predetermined time, for each cluster section; and an attention assessment calculation step of calculating at least one of an attention assessment for an eye opening/cluster section, which is an eye opening section and cluster section, based on at least one of the microsaccade rate, the sharpness of microsaccade, the standard deviation of the degree of eyelid opening, the short-time eye-closure occurrence rate and the long-time eye-closure occurrence rate for each eye opening section, an attention assessment for an eye closing/cluster section, which is an eye closing section and cluster section, based on at least one of the standard deviation of the degree of eyelid opening, the short-time eye-closure occurrence rate and the long-time eye-closure occurrence rate, an attention assessment for an eye-blinking/cluster section, which is an eye-blinking section and cluster section, based on at least one of the short-time eye-closure occurrence rate and the long-time eye-closure occurrence rate, an attention assessment for an eye opening/non-cluster section, which is an eye opening section and non-cluster section, based on at least one of the microsaccade rate, the sharpness of microsaccade and the standard deviation of the degree of eyelid opening for each eye opening section, and an attention assessment for an eye closing/non-cluster section, which is an eye closing section and non-cluster section, based on at least the standard deviation of the degree of eyelid opening.

(17) A reduced attention state estimation method, comprising:

a section determination step of determining an eye opening section, an eye closing section, an eye-blinking section and a cluster section based on eyeball movement and eyelid activity data obtained by measuring an eyeball movement and an eyelid activity of a subject;

an eyeball movement and eyelid activity-related information calculation step of calculating, based on the eyeball movement and eyelid activity data, at least one of a microsaccade rate for each eye opening section, a relative velocity of a saccade for each eye opening section, a standard deviation of a degree of eyelid opening for each eye opening section and/or each eye closing section, an average value of the degree of eyelid opening for each eye opening section and/or each eye closing section and a duration of an eye-blinking for each cluster section; and an attention assessment calculation step of calculating at least one of an attention assessment for an eye opening/cluster section, which is an eye opening section and cluster section, based on at least one of the microsaccade rate, the relative velocity of a saccade, the standard deviation of the degree of eyelid opening, the average value of the degree of eyelid opening and the duration of an eye-blinking, an attention assessment for an eye closing/cluster section, which is an eye closing section and cluster section, based on at least one of the standard deviation of the degree of eyelid opening, the average value of the degree of eyelid opening and the duration of an eye-blinking, an attention assessment for an eye-blinking/cluster section, which is an eye-blinking section and cluster section, based on at least the duration of an eye-blinking, an attention assessment for an eye opening/non-cluster section, which is an eye opening section and non-cluster section, based on at least one of the microsaccade rate, the relative velocity of a saccade, the standard deviation of the degree of eyelid opening and the average value of the degree of eyelid opening, and an attention assessment for an eye closing/non-cluster section, which is an eye closing section and non-cluster section, based on at least one of the standard deviation of the degree of eyelid opening and the average value of the degree of eyelid opening, wherein the attention assessment is any of three or more levels of attention reduction.

(18) A reduced attention state estimation method, comprising:

a section determination step of determining an eye opening section, an eye closing section, an eye-blinking section and a cluster section based on eyeball movement and eyelid activity data obtained by measuring an eyeball movement and an eyelid activity of a subject;

an eyeball movement and eyelid activity-related information calculation step of calculating, based on the eyeball movement and eyelid activity data, at least two of a microsaccade rate for each eye opening section, a relative velocity of a saccade for each eye opening section, a standard deviation of a degree of eyelid opening for each eye opening section and/or each eye closing section and a duration of an eye-blinking for each cluster section; and an attention assessment calculation step of calculating at least one of an attention assessment for an eye opening/cluster section, which is an eye opening section and cluster section, based on at least two of the microsaccade rate, the relative velocity of a saccade, the standard deviation of the degree of eyelid opening, the average value of the degree of eyelid opening and the duration of an eye-blinking, an attention assessment for an eye closing/cluster section, which is an eye closing section and cluster section, based on at least two of the standard deviation of the degree of eyelid opening, the average value of the degree of eyelid opening and the duration of an eye-blinking, an attention assessment for an eye opening/non-cluster section, which is an eye opening section and non-cluster section, based on at least two of the microsaccade rate, the relative velocity of a saccade, the standard deviation of the degree of eyelid opening and the average value of the degree of eyelid opening, and an attention assessment for an eye closing/non-cluster section, which is an eye closing section and non-cluster section, based on at least the standard deviation of the degree of eyelid opening and the average value of the degree of eyelid opening.

(19) A reduced attention state estimation method, comprising:

a section determination step of determining an eye opening section, an eye closing section, an eye-blinking section and a cluster section based on eyeball movement and eyelid activity data obtained by measuring an eyeball movement and an eyelid activity of a subject;

an eyeball movement and eyelid activity-related information calculation step of calculating at least one of whether a relevant section is an eye opening section, an eye closing section or an eye-blinking section, whether an eye opening section or an eye-blinking section is included in a cluster section, whether an eye closing section is included in a cluster section, a sharpness of microsaccade, a frequency of microsaccades, a duration of an eye opening section, a frequency of eye-blinkings, an inverse of a relative velocity of an eyelid closure at eyelid closing time, an inverse of a relative velocity of an eyelid opening at an eyelid opening time, a duration of a closed eye in an eye-blinking, a rate of occurrence of eye-blinkings and a duration of an eye closing section based on a microsaccade rate for each eye opening section, a relative velocity of a saccade for each eye opening section, a standard deviation of a degree of eyelid opening for each eye opening section and/or each eye closing section, an average value of the degree of eyelid opening for each eye opening section and/or each eye closing section, a duration of an eye-blinking for each cluster section, and the eyeball movement and eyelid activity data; and an attention assessment step of determining at least one of an attention assessment for an eye opening/cluster section, which is an eye opening section and cluster section, based on at least one of the microsaccade rate, the relative velocity of a saccade, the standard deviation of the degree of eyelid opening, the average value of the degree of eyelid opening and the duration of an eye-blinking, and at least one of whether a relevant section is an eye opening section, an eye closing section or an eye-blinking section, whether an eye opening section or an eye-blinking section is included in a cluster section, the sharpness of microsaccade, the frequency of microsaccades, the duration of an eye opening section, the frequency of eye-blinkings, the inverse of a relative velocity of an eyelid closure at an eyelid closing time, the inverse of a relative velocity of an eyelid opening at an eyelid opening time, the duration of a closed eye in an eye-blinking and the rate of occurrence of eye-blinkings, an attention assessment for an eye closing/cluster section, which is an eye closing section and cluster section, based on at least one of the standard deviation of the degree of eyelid opening, the average value of the degree of eyelid opening and the duration of an eye-blinking, and at least one of whether a relevant section is an eye opening section, an eye closing section or an eye-blinking section, whether an eye closing section is included in a cluster section, the duration of an eye closing section, the frequency of eye-blinkings, the inverse of a relative velocity of an eyelid closure at an eyelid closing time, the inverse of a relative velocity of an eyelid opening at an eyelid opening time, the duration of a closed eye in an eye-blinking, and the rate of occurrence of eye-blinkings, an attention assessment for an eye-blinking/cluster section, which is an eye-blinking section and cluster section, based on at least one of the duration of an eye-blinking, whether a relevant section is an eye opening section, an eye closing section or an eye-blinking section, whether an eye opening section or an eye-blinking section is included in a cluster section, the frequency of eye-blinkings, the inverse of a relative velocity of an eyelid closure at an eyelid closing time, the inverse of a relative velocity of an eyelid opening at an eyelid opening time, the duration of a closed eye in an eye-blinking and the rate of occurrence of eye-blinkings, an attention assessment for an eye opening/non-cluster section, which is an eye opening section and non-cluster section, based on at least one of the microsaccade rate, the relative velocity of a saccade, the standard deviation of the degree of eyelid opening and the average value of the degree of eyelid opening, and at least one of whether a relevant section is an eye opening section, an eye closing section or an eye-blinking section, whether an eye opening section or an eye-blinking section is included in a cluster section, the frequency of microsaccades and the duration of an eye opening section, an attention assessment for an eye closing/non-cluster section, which is an eye closing section and non-cluster section, based on at least the standard deviation of the degree of eyelid opening and the average value of the degree of eyelid opening, and at least one of whether a relevant section is an eye opening section, an eye closing section or an eye-blinking section and the duration of an eye closing section, and an attention assessment for an eye-blinking/non-cluster section, which is an eye-blinking section and non-cluster section, based on at least one of whether a relevant section is an eye opening section, an eye closing section or an eye-blinking section and whether an eye opening section or an eye-blinking section is included in a cluster section.

(20) The reduced attention state estimation method according to any one of Items (16) to (19), wherein the attention assessment is an estimated probability of occurrence of each attention reduction level determined by a Naive Bayes estimation.

(21) A reduced attention state estimation method, comprising:

a section determination step of determining an eye opening section based on eyeball movement and eyelid activity data obtained by measuring an eyeball movement and an eyelid activity of a subject;

an eyeball movement and eyelid activity-related information calculation step of calculating a microsaccade rate for each eye opening section and/or a sharpness of microsaccade for each eye opening section based on the eyeball movement and eyelid activity data; and an attention assessment step of determining an attention assessment for the eye opening section based on at least the microsaccade rate and/or the sharpness of microsaccade for the eye opening section.

(22) A reduced attention state estimation method, comprising:

a section determination step of determining an eye opening section based on eyeball movement and eyelid activity data obtained by measuring an eyeball movement and an eyelid activity of a subject;

an eyeball movement and eyelid activity-related information calculation step of calculating a microsaccade rate and/or a relative velocity of a saccade for each eye opening section based on the eyeball movement and eyelid activity data; and an attention assessment step of determining an attention assessment for the eye opening section based on at least the microsaccade rate and/or the relative velocity of a saccade, wherein the attention assessment is any of three or more levels of attention reduction.

(23) A reduced attention state estimation method, comprising:

a section determination step of determining an eye opening section and/or an eye closing section based on eyeball movement and eyelid activity data obtained by measuring an eyeball movement and an eyelid activity of a subject;

an eyeball movement and eyelid activity-related information calculation step of calculating a standard deviation of a degree of eyelid opening and/or an average value of the degree of eyelid opening for each eye opening section and/or each eye closing section based on the eyeball movement and eyelid activity data; and an attention assessment step of determining an attention assessment for the eye opening section and/or the eye closing section based on at least the standard deviation of the degree of eyelid opening and/or the average value of the degree of eyelid opening, wherein the attention assessment is any of three or more levels of attention reduction.

(24) A reduced attention state estimation method, comprising:

a section determination step of determining a cluster section based on eyeball movement and eyelid activity data obtained by measuring an eyeball movement and an eyelid activity of a subject;

an eyeball movement and eyelid activity-related information calculation step of calculating a duration of an eye-blinking for each cluster section based on the eyeball movement and eyelid activity data; and an attention assessment step of determining an attention assessment for the cluster section based on at least the duration of an eye-blinking, wherein the attention assessment is any of three or more levels of attention reduction.

(25) A reduced attention state estimation method, comprising:

a section determination step of determining an eye opening section based on eyeball movement and eyelid activity data obtained by measuring an eyeball movement and an eyelid activity of a subject;

an eyeball movement and eyelid activity-related information calculation step of calculating a microsaccade rate and a relative velocity of a saccade for each eye opening section based on the eyeball movement and eyelid activity data; and an attention assessment step of determining an attention assessment for the eye opening section based on at least the microsaccade rate and the relative velocity of a saccade.

(26) A reduced attention state estimation method, comprising:

a section determination step of determining an eye opening section and/or an eye closing section based on eyeball movement and eyelid activity data obtained by measuring an eyeball movement and an eyelid activity of a subject;

an eyeball movement and eyelid activity-related information calculation step of calculating a standard deviation of a degree of eyelid opening and an average value of the degree of eyelid opening for each eye opening section and/or each eye closing section based on the eyeball movement and eyelid activity data; and an attention assessment step of determining an attention assessment for the eye opening section and/or the eye closing section based on at least the standard deviation of the degree of eyelid opening and the average value of the degree of eyelid opening.

(27) A program that makes a computer perform the reduced attention state estimation method according to any one of Items (16) to (26).

(28) A computer-readable storage medium storing the program according to Item (27).

EXPLANATIONS OF LETTERS OR NUMERALS

1 reduced attention state estimation system
11 eyeball movement and eyelid activity measurement unit
12 PVT conducting unit
13 section determination unit
15 eyeball movement and eyelid activity-related information calculation unit
17 attention assessment unit
18 prior probability and likelihood calculation unit
19 storage unit

The invention claimed is:

1. A reduced attention state estimation system, comprising:

an eyeball movement and eyelid activity measurement unit that measures an eyeball movement and an eyelid activity of a subject to obtain eyeball movement and eyelid activity data;

a section determination unit that determines an eye opening section, an eye closing section, an eye-blinking section and a cluster section based on the eyeball movement and eyelid activity data;

an eyeball movement and eyelid activity-related information calculation unit that calculates, based on the eyeball movement and eyelid activity data, at least one of a standard deviation of a degree of eyelid opening for each eye opening section and/or each eye closing section, a short-time eye-closure occurrence rate, which is a rate of occurrence of an eye closure having a duration shorter than a predetermined time, for each cluster section, and a long-time eye-closure occurrence rate, which is a rate of occurrence of an eye closure having a duration equal to or longer than the predetermined time, for each cluster section; and an attention assessment unit that determines at least one of an attention assessment for an eye opening/cluster section, which is an eye opening section and cluster section, based on at least one of the standard deviation of the degree of eyelid opening, the short-time eye-closure occurrence rate and the long-time eye-closure occurrence rate, an attention assessment for an eye closing/cluster section, which is an eye closing section and cluster section, based on at least one of the standard deviation of the degree of eyelid opening, the short-time eye-closure occurrence rate and the long-time eye-closure occurrence rate, an attention assessment for an eye-blinking/cluster section, which is an eye-blinking section and cluster section, based on at least one of the short-time eye-closure occurrence rate and the long-time eye-closure occurrence rate, an attention assessment for an eye opening/non-cluster section, which is an eye opening section and non-cluster section, based on the standard deviation of the degree of eyelid opening, and an attention assessment for an eye closing/non-cluster section, which is an eye closing section and non-cluster section, based on at least the standard deviation of the degree of eyelid opening.

2. The reduced attention state estimation system according to claim 1, wherein the eyeball movement and eyelid activity-related information calculation unit further calculates, based on the eyeball movement and eyelid activity data, one of whether a relevant section is an eye opening section, an eye closing section or an eye-blinking section, whether an eye opening section or an eye-blinking section is included in a cluster section, whether an eye closing section is included in a cluster section, a frequency of microsaccades, a duration of an eye opening section, an average value of the degree of eyelid opening, a frequency of eye-blinkings, an inverse of a relative velocity of an eyelid closure at an eyelid closing time, an inverse of a relative velocity of an eyelid opening at an eyelid opening time, a duration of an eye-blinking, a duration of a closed eye in an eye-blinking, a rate of occurrence of eye-blinkings, and a duration of an eye closing section, and the attention assessment unit determines at least one of an attention assessment for the eye opening/cluster section, which is an eye opening section and cluster section, based on at least one of the standard deviation of the degree of eyelid opening, the short-time eye-closure occurrence rate and the long-time eye-closure occurrence rate, and at least one of whether a relevant section is an eye opening section, an eye closing section or an eye-blinking section, whether an eye opening section or an eye-blinking section is included in a cluster section, the frequency of microsaccades, the duration of an eye opening section, the average value of the degree of eyelid opening, the frequency of eye-blinkings, the inverse of a relative velocity of an eyelid closure at an eyelid closing time, the inverse of a relative velocity of an eyelid opening at an eyelid opening time, the duration of an eye-blinking, the duration of a closed eye in an eye-blinking and the rate of occurrence of eye-blinkings, an attention assessment for the eye closing/cluster section, which is an eye closing section and cluster section, based on at least one of the standard deviation of the degree of eyelid opening, the short-time eye-closure occurrence rate and the long-time eye-closure occurrence rate, and at least one of whether a relevant section is an eye opening section, an eye closing section or an eye-blinking section, whether an eye closing section is included in a cluster section, the duration of an eye closing section, the average value of the degree of eyelid opening, the frequency of eye-blinkings, the inverse of a relative velocity of an eyelid closure at an eyelid closing time, the inverse of a relative velocity of an eyelid opening at an eyelid opening time, the duration of an eye-blinking, the duration of a closed eye in an eye-blinking and the rate of occurrence of eye-blinkings, an attention assessment for an eye-blinking/cluster section, which is an eye-blinking section and cluster section, based on at least one of the short-time eye-closure occurrence rate and the long-time eye-closure occurrence rate, and at least one of whether a relevant section is an eye opening section, an eye closing section or an eye-blinking section, whether an eye opening section or an eye-blinking section is included in a cluster section, the frequency of eye-blinkings, the inverse of a relative velocity of an eyelid closure at an eyelid closing time, the inverse of a relative velocity of an eyelid opening at an eyelid opening time, the duration of an eye-blinking, the duration of a closed eye in an eye-blinking and the rate of occurrence of eye-blinkings, an attention assessment for an eye opening/non-cluster section, which is an eye opening section and non-cluster section, based on the standard deviation of the degree of eyelid opening, and at least one of whether a relevant section is an eye opening section, an eye closing section or an eye-blinking section, whether an eye opening section or an eye-blinking section is included in a cluster section, the frequency of microsaccades, the duration of an eye opening section and the average value of the degree of eyelid opening, an attention assessment for an eye closing/non-cluster section, which is an eye closing section and non-cluster section, based on the standard deviation of the degree of eyelid opening and at least one of whether a relevant section is an eye opening section, an eye closing section or an eye-blinking section, the duration of an eye closing section and the average value of the degree of eyelid opening, and an attention assessment for an eye-blinking/non-cluster section, which is an eye-blinking section and non-cluster section, based on at least one of whether a relevant section is an eye opening section, an eye closing section or an eye-blinking section and whether an eye opening section or an eye-blinking section is included in a cluster section.

3. The reduced attention state estimation system according to claim 1, wherein the attention assessment is an estimated probability of occurrence of each attention reduction level determined by a Naive Bayes estimation.

4. The reduced attention state estimation system according to claim 3, wherein the attention assessment is an estimated probability of occurrence of each attention reduction level per assessment time calculated based on the estimated probability of occurrence of each attention reduction level calculated for each of the eye opening/cluster section, the eye closing/cluster section, the eye-blinking/cluster section, the eye opening/non-cluster section, the eye closing/non-cluster section and the eye-blinking/non-cluster section.

5. The reduced attention state estimation system according to claim 3, wherein a first prior probability in the Naive Bayes estimation is calculated based on training data derived from personal eyeball movement and eyelid activity data of the subject.

6. A reduced attention state estimation method, comprising:
- a section determination step of determining an eye opening section, an eye closing section, an eye-blinking section and a cluster section based on eyeball movement and eyelid activity data obtained by measuring an eyeball movement and an eyelid activity of a subject;
- an eyeball movement and eyelid activity-related information calculation step of calculating, based on the eyeball movement and eyelid activity data, at least one of a standard deviation of a degree of eyelid opening for each eye opening section and/or each eye closing section, a short-time eye-closure occurrence rate, which is a rate of occurrence of an eye closure having a duration shorter than a predetermined time, for each cluster section, and a long-time eye-closure occurrence rate, which is a rate of occurrence of an eye closure having a duration equal to or longer than the predetermined time, for each cluster section; and
- an attention assessment calculation step of calculating at least one of
- an attention assessment for an eye opening/cluster section, which is an eye opening section and cluster section, based on at least one of the standard deviation of the degree of eyelid opening, the short-time eye-closure occurrence rate and the long-time eye-closure occurrence rate,
- an attention assessment for an eye closing/cluster section, which is an eye closing section and cluster section, based on at least one of the standard deviation of the degree of eyelid opening, the short-time eye-closure occurrence rate and the long-time eye-closure occurrence rate,
- an attention assessment for an eye-blinking/cluster section, which is an eye-blinking section and cluster section, based on at least one of the short-time eye-closure occurrence rate and the long-time eye-closure occurrence rate,
- an attention assessment for an eye opening/non-cluster section, which is an eye opening section and non-cluster section, based on at least one of the standard deviation of the degree of eyelid opening, and
- an attention assessment for an eye closing/non-cluster section, which is an eye closing section and non-cluster section, based on at least the standard deviation of the degree of eyelid opening.

7. A non-transitory computer-readable storage medium storing a computer program that causes a computer to perform the reduced attention state estimation method according to claim 6.

8. The reduced attention state estimation method according to claim 6, wherein the eyeball movement and eyelid activity-related information calculation step further includes calculating, based on the eyeball movement and eyelid activity data, one of whether a relevant section is an eye opening section, an eye closing section or an eye-blinking section, whether an eye opening section or an eye-blinking section is included in a cluster section, whether an eye closing section is included in a cluster section, a frequency of microsaccades, a duration of an eye opening section, an average value of the degree of eyelid opening, a frequency of eye-blinkings, an inverse of a relative velocity of an eyelid closure at an eyelid closing time, an inverse of a relative velocity of an eyelid opening at an eyelid opening time, a duration of an eye-blinking, a duration of a closed eye in an eye-blinking, a rate of occurrence of eye-blinkings, and a duration of an eye closing section, and
- the attention assessment calculation step is determining at least one of
- an attention assessment for the eye opening/cluster section, which is an eye opening section and cluster section, based on at least one of the standard deviation of the degree of eyelid opening, the short-time eye-closure occurrence rate and the long-time eye-closure occurrence rate, and at least one of whether a relevant section is an eye opening section, an eye closing section or an eye-blinking section, whether an eye opening section or an eye-blinking section is included in a cluster section, the frequency of microsaccades, the duration of an eye opening section, the average value of the degree of eyelid opening, the frequency of eye-blinkings, the inverse of a relative velocity of an eyelid closure at an eyelid closing time, the inverse of a relative velocity of an eyelid opening at an eyelid opening time, the duration of an eye-blinking, the duration of a closed eye in an eye-blinking and the rate of occurrence of eye-blinkings,
- an attention assessment for the eye closing/cluster section, which is an eye closing section and cluster section, based on at least one of the standard deviation of the degree of eyelid opening, the short-time eye-closure occurrence rate and the long-time eye-closure occurrence rate, and at least one of whether a relevant section is an eye opening section, an eye closing section or an eye-blinking section, whether an eye closing section is included in a cluster section, the duration of an eye closing section, the average value of the degree of eyelid opening, the frequency of eye-blinkings, the inverse of a relative velocity of an eyelid closure at an eyelid closing time, the inverse of a relative velocity of an eyelid opening at an eyelid opening time, the duration of an eye-blinking, the duration of a closed eye in an eye-blinking and the rate of occurrence of eye-blinkings,
- an attention assessment for an eye-blinking/cluster section, which is an eye-blinking section and cluster section, based on at least one of the short-time eye-closure occurrence rate and the long-time eye-closure occurrence rate, and at least one of whether a relevant section is an eye opening section, an eye closing section or an eye-blinking section, whether an eye opening section or an eye-blinking section is included in a cluster section, the frequency of eye-blinkings, the inverse of a relative velocity of an eyelid closure at an eyelid closing time, the inverse of a relative velocity of an eyelid opening at an eyelid opening time, the duration of an eye-blinking, the duration of a closed eye in an eye-blinking and the rate of occurrence of eye-blinkings, an attention assessment for an eye opening/non-cluster section, which is an eye opening section and non-cluster section, based on the standard deviation of the degree of eyelid opening, and at least one of whether a relevant section is an eye opening section, an eye closing section or an eye-blinking section, whether an eye opening section or an eye-blinking section is included in a cluster section, the frequency of micro-saccades, the duration of an eye opening section and the average value of the degree of eyelid opening, an attention assessment for an eye closing/non-cluster section, which is an eye closing section and non-cluster section, based on the standard deviation of the degree of eyelid opening and at least one of whether a relevant section is an eye opening section, an eye closing section or an eye-blinking section, the duration of an eye closing section and the average value of the degree of eyelid opening, and an attention assessment for an eye-blinking/non-cluster section, which is an eye-blinking section and non-cluster section, based on at least one of whether a relevant section is an eye opening section, an eye closing section or an eye-blinking section and whether an eye opening section or an eye-blinking section is included in a cluster section.

9. The reduced attention state estimation method according to claim 6, wherein the attention assessment is an estimated probability of occurrence of each attention reduction level determined by a Naive Bayes estimation.

10. The reduced attention state estimation method according to claim 9, wherein the attention assessment is an estimated probability of occurrence of each attention reduction level per assessment time calculated based on the estimated probability of occurrence of each attention reduction level calculated for each of the eye opening/cluster section, the eye closing/cluster section, the eye-blinking/cluster section, the eye opening/non-cluster section, the eye closing/non-cluster section and the eye-blinking/non-cluster section.

11. The reduced attention state estimation system according to claim 9, wherein a first prior probability in the Naive Bayes estimation is calculated based on training data derived from personal eyeball movement and eyelid activity data of the subject.

* * * * *